US011172629B2

(12) United States Patent
Sirizzotti et al.

(10) Patent No.: US 11,172,629 B2
(45) Date of Patent: Nov. 16, 2021

(54) CGMMV RESISTANT CITRULLUS PLANTS

(71) Applicant: NUNHEMS B.V., Nunhem (NL)

(72) Inventors: Alberto Sirizzotti, Sant Agata Bolognese (IT); Daniel Bellon Dona, Paterna (ES); Richard Bernard Berentsen, Paterna (ES); Daniel Jimenez Fernandez, Paterna (ES)

(73) Assignee: NUNHEMS B.V., Nunhem (NL)

( * ) Notice: Subject to any disclaimer, the term of this patent is extended or adjusted under 35 U.S.C. 154(b) by 27 days.

(21) Appl. No.: 16/639,351

(22) PCT Filed: Jul. 20, 2018

(86) PCT No.: PCT/EP2018/069714
§ 371 (c)(1),
(2) Date: Feb. 14, 2020

(87) PCT Pub. No.: WO2019/034364
PCT Pub. Date: Feb. 21, 2019

(65) Prior Publication Data
US 2021/0000047 A1    Jan. 7, 2021

(30) Foreign Application Priority Data

Aug. 17, 2017 (EP) ..................... 17186574

(51) Int. Cl.
*A01H 6/34* (2018.01)
*A01H 5/08* (2018.01)
*C12Q 1/6895* (2018.01)

(52) U.S. Cl.
CPC .............. *A01H 6/342* (2018.05); *A01H 5/08* (2013.01); *C12Q 1/6895* (2013.01); *C12Q 2600/13* (2013.01); *C12Q 2600/156* (2013.01)

(58) Field of Classification Search
CPC combination set(s) only.
See application file for complete search history.

(56) References Cited

U.S. PATENT DOCUMENTS

2013/0298273 A1    11/2013    Chang et al.

FOREIGN PATENT DOCUMENTS

WO    2012062672 A1    5/2012
WO    2015150560 A1    10/2015

OTHER PUBLICATIONS

Cuucap Team: CucCAP: Leveraging applied genomics to improve disease resistance in cucurbit crops Second Annual CucCAP Team Meeting Mar. 27-28, 2017. Provided by Applicant. (Year: 2017).*
"A Seed Production and Commercial Growers Guide", Cucumber Green Mottle Mosaic Virus, ASTA, Apr. 2014, 9 pages.
"CucCAP: Leveraging applied genomics to improve disease resistance in cucurbit crops", Cucurbit Coordinated Agricultural Project, Disease Resistance via Applied Genomics, Second Annual CucCAP Team Meeting, Mar. 27-28, 2017, 73 pages.
Allen, et al., "Transcript-specific, single-nucleotide polymorphism discovery and linkage analysis in hexaploid bread wheat (*Triticum aestivum* L.)", Plant Biotechnology Journal, vol. 9, Issue 9, Jun. 1, 2011, pp. 1086-1099.
Bigdelo, et al., "Evaluation of bitter apple ('*Citrullus colocynthis*' (L.) *Schrad*) as potential rootstock for watermelon", Australian Journal of Crop Science , vol. 11, Issue 6, Jun. 2017, pp. 727-732.
Darzi, et al., "The honeybee *Apis mellifera* contributes to Cucumber green mottle mosaic virus spread via pollination", Plant Pathology, vol. 67, Issue 1, Mar. 10, 2017, pp. 244-251.
Davis, et al., "Cucurbit Grafting", Critical Reviews in Plant Sciences, vol. 27, Issue 1, 2008, pp. 50-74.
European Search Report for EP Patent Application No. 17186574.4, dated Jan. 12, 2018, 4 pages.
Hassell, et al., "Grafting Methods for Watermelon Production", HortScience, vol. 43, Issue 6, Oct. 2008, pp. 1677-1679.
Henikoff, et al., "Amino acid substitution matrices from protein blocks",Proceedings of the National Academy of Sciences USA, vol. 89, Issue 22, Nov. 1992, p. 10915-10919.
Hongyun, et al., "Real time TaqMan RT-PCR assay for the detection of Cucumber green mottle mosaic virus", Journal of Virological Methods, vol. 149, Issue 2, May 2008, pp. 326-329.
International Search Report for PCT Patent Application No. PCT/EP2018/069714, dated Oct. 25, 2018, 5 pages.
J. Horváth, "New artificial host—virus relations between cucurbitaceous plants and viruses I. *Benincasa, Bryonia, Bryonopsis* and *Citrullus* species", Acta Phytopathologica Academiae Scientiarum Hungaricae , vol. 20, Issue 3/4, 1985, pp. 225-251.
Lee, et al., "Occurrence of cucumber green mottle mosaic virus disease of watermelon in Korea", Korean Journal of Plant Pathology, vol. 6, Issue 2, 1990, pp. 250-255.
Levi, et al., "Genetic diversity among watermelon (*Citrullus lanatus* and *Citrullus colocynthis*) accessions", Genetic Resources and Crop Evolution, vol. 48, Dec. 2001, pp. 559-566.
Levi, et al., "Utilizing genetic diversity in the desert watermelon *Citrullus colocynthis* for enhancing watermelon cultivars for resistance to biotic and abiotic stress", Cucurbitaceae 2016, XIth Eucarpia Meeting on Cucurbit Genetics & Breeding, ed. Kozik, et al., Jul. 24-28, 2016, pp. 105-108.
Li, et al., "Cytogenetic relationships among *Citrullus* species in comparison with some genera of the tribe Benincaseae (*Cucurbitaceae*) as inferred from rDNA distribution patterns", BMC Evolutionary Biology, vol. 16, Issue 85, Apr. 18, 2016, 9 pages.
Lin, et al., "Development of transgenic watermelon resistant to Cucumber mosaic virus and Watermelon mosaic virus by using a single chimeric transgene construct", Transgenic Research, vol. 21, Dec. 28, 2011, pp. 983-993.

(Continued)

*Primary Examiner* — Brent T Page
(74) *Attorney, Agent, or Firm* — Arent Fox LLP

(57) ABSTRACT

The present invention relates to cultivated watermelon plants comprising CGMMV resistance due to introgression of QTLs from a CGMMV resistant donor of the species *Citrullus colocynthis*.

15 Claims, 3 Drawing Sheets
Specification includes a Sequence Listing.

(56) References Cited

OTHER PUBLICATIONS

Ling, et al., "First Report of Cucumber green mottle mosaic virus Infecting Greenhouse Cucumber in Canada", The American Phytopathological Society, vol. 98, Issue 5, Apr. 11, 2014, p. 701.

Mandal, et al., "Properties, Diagnosis and Management of Cucumber green mottle mosaic virus", Plant Viruses, vol. 2, Issue 1, 2008, pp. 25-34.

McGregor, et al., "Flowering Patterns of Pollenizer and Triploid Watermelon Cultivars", HortScience, American Society of Horticulture Science, vol. 49, Issue 6, Jun. 2014, pp. 714-721.

N. A. Kazi, "Review Paper—Polyploidy in Vegetables", Journal of Global Biosciences, vol. 4, Issue 3, 2015, pp. 1774-1779.

Park, et al., "Transgenic watermelon rootstock resistant to CGMMV (cucumber green mottle mosaic virus) infection", Genetic Transformation and Hybridization, Plant Cell Reports, vol. 24, Issue 6, Jun. 14, 2005, pp. 350-356.

Qin, et al., "Effects of Dual/Threefold Rootstock Grafting on the Plant Growth, Yield and Quality of Watermelon", Notulae Botanicae Horti Agrobotanici Cluj-Napoca, vol. 42, Issue 4, 2014, pp. 495-500.

Reingold, et al., "Epidemiological study of Cucumber green mottle mosaic virus in greenhouses enables reduction of disease damage in cucurbit production", Annals of Applied Biology, vol. 168, Issue 1, Jul. 6, 2015, pp. 29-40.

Reingold, et al., "First report of Cucumber green mottle mosaic virus (CGMMV) symptoms in watermelon used for the discrimination of non-marketable fruits in Israeli commercial fields", New Disease Reports 28, Nov. 12, 2013, 11 page.

Renny-Byfield, et al., "Doubling down on genomes: Polyploidy and crop plants", American Journal of Botany, vol. 101, Issue 10, Oct. 1, 2014, pp. 1711-1725.

Singh, et al., "Role of Grafting in Cucurbitaceous Crops—A Review", Agricultural Reviews, vol. 35, Issue 1, Mar. 1, 2014, pp. 24-33.

Yetisir, et al., "Effect of different rootstock on plant growth, yield and quality of watermelon", Australian Journal of Experimental Agriculture, vol. 43, Issue 10, Nov. 25, 2003, pp. 1269-1274.

* cited by examiner

CGMMV RESISTANT CITRULLUS PLANTS

CROSS-REFERENCE TO RELATED APPLICATIONS

This application is a National Stage Entry of PCT/EP2018/069714, filed Jul. 20, 2018, which claims priority to European Patent Application No. 17186574.4, filed Aug. 17, 2017, the disclosures of each of which are hereby incorporated by reference in their entireties.

The present invention relates to *Citrullus* plant cells and *Citrullus* plants, *Citrullus colocynthis* plant cells and *Citrullus colocynthis* plants being resistant to CGMMV (Cucumber Green Mottle Mosaic Virus), grafted plants comprising *Citrullus* scions or rootstocks being resistant to CGMMV, as well as methods for the production of said plants and uses of said plant cells and plants. Methods for combating CGMMV induced yield loss and methods for production of CGMMV resistant seeds are also comprised.

CGMMV (Cucumber Green Mottle Mosaic Virus) was first reported in cucumber (*Cucumis sativus*) from Great Britain in 1953 by Ainswoth. Subsequently the virus was reported also from several countries in Asia and Europe e.g., China, Israel, Greece, Japan, India, Korea, Netherlands, Pakistan, Poland, Russia, Saudi Arabia, Spain, Taiwan and Ukraine. CGMMV is one of the few plant viruses which have been reported in Antarctica. (Mandal et al., 2008, Plant Viruses 2(1), 25-34).

CGMMV recently has been described in a melon seed production field in the USA (ASTA education pamphlet, 2014, A Seed Production and Commercial Growers Guide) in 2014, in Australia (Australian Government, 2016, Draft Pest risk analysis for Cucumber green mottle mosaic virus (CGMMV)) in 2013 in commercial watermelon farms and in Canada by cucumber growers in greenhouse grown mini-cucumbers (Ling & Li, 2014, apsjournalsapsnet.org-doi-abs-10.1094-PDIS-09-13-0996-PDN).

CGMMV is a plus-strand RNA virus species under the genus Tobamovirus forming a distinct evolutionary clade separated from the other cucurbit infecting tobamovirus species. The closest relatives of CGMMV are other cucurbit-infecting tobamoviruses, KGMMV, CFMMV and ZGMMV. In the complete genome sequence, CGMMV shares 59.1-60.4% similarity with the other cucurbit-infecting tobamoviruses and only 46.0-49.3% with the rest of the tobamovirus species. (Mandal et al., 2008, Plant Viruses 2(1), 25-34).

The host range of CGMMV is narrow and mainly restricted to Cucurbitaceae and Chenopodiaceae. Some isolates however, infect a few species of Solanaceae. The natural host range of CGMMV includes *Cucumis sativus*, *Cucumis anguria*, *Cucumis melo*, *Citrullus lanatus* and *Lagenaria siceraria*. In Antarctica, CGMMV has been detected in unusual hosts viz., mosses (*Barbilophozia* and *Polytrchum*) and Antarctic hairgrass (*Deschampsia antarctica*). The experimental host range of CGMMV includes the following plant species: *Chenopodium amaranticolor*, *Citrullus lanatus*, *Cucumis sativus*, *Cucumis melo*, *Cucumis melo* var. *utilissima*, *Cucurbita pepo*, *Cucumis moschata*, *Datura stramonium*, *Lagenaria siceraria*, *Luffa acutangula*, *Nicotiana benthamiana*, *Nicotiana debneyii* and *Trichosanthes anguina*. *Momordica charantia* and *Nicotiana tabacum* are symptomless hosts. The majority of the host species produce systemic symptoms and a few (*C. amaranticolor* and *Datura stramonium*) produce local lesion symptoms. (Mandal et al., 2008, Plant Viruses 2(1), 25-34).

The typical disease symptoms caused by CGMMV are systemic greenish mottle mosaic on foliage, however, symptomatology varies based on isolate/strain and the plant species affected. In grafted watermelon plants, CGMMV causes 'blood flesh' disease in Korea (Lee et al. 1990), 'Konnyaku' disease in Japan and similar disease in Greece. (Mandal et al., 2008, Plant Viruses 2(1), 25-34) Watermelon (*Citrullus lanatus* ssp *vulgaris*) infected with CGMMV can produce externally healthy looking fruits which, however, internally show deterioration of the pulp and are thus not eatable and therefore not marketable (Hongyun et al., 2008, J. Virological Methods 149, 326-329).

Systemic movement in infected host plants is one of the key processes of viral pathogenesis. Movement of virus in plant takes place through two major steps, short distance movement from cell to cell through plasmodesmata and long distance movement through vascular tissues. The long distance movement of CGMMV is from photoassimilate source to sink, which supports phloem transport mechanisms. In systemically infected sink leaves, CGMMV is simultaneously detected in the xylem and phloem. CGMMV accumulates in high levels in the differentiating tracheids of young leaves. (Mandal et al., 2008, Plant Viruses 2(1), 25-34).

CGMMV natural spread is largely through contact of infected plant materials. Infection of plants with CGMMV occurs by transmitting through soil and irrigation water contaminated with infected plant debris. The debris of diseased plants possibly contributes as primary source of infection to a limited number of plants and successively the virus spreads through plant-to-plant contact. In watermelon CGMMV is an important virus transmitted by seeds and graft material (rootstock or scion). Seed transmission of CGMMV has been also described in bottle gourd and cucumber. Transmission of CGMMV by insects has been investigated but no specific virus-insect vector relationships could be established. In India, however, transmission of CGMMV by cucumber leaf beetle, *Raphidopalpa faeveicollis* has been demonstrated. Recently honey bees (*Apis mellifera*) have been demonstrated to transfer CGMMV during pollination (Darzi et al., 2017, Plant Pathology, 1365-3059, doi: 10.1111/ppa.12702). Cutting knives used by growers for harvesting fruits from diseased plants can potentially contribute additional means of field-spread of CGMMV during fruiting stage of crop. (Mandal et al., 2008, Plant Viruses 2(1), 25-34).

CGMMV causes severe diseases in Cucurbits worldwide. In watermelon leaf mottling and mosaic have been described in greenhouse grown plants. Necrotic spots on the peduncle of plants have been described to occur simultaneously with CGMMV infection. Symptoms in watermelon fruits include exocarp deterioration and rotting or yellowing of the fleshy mesocarp which are commonly only determinable after harvest. (Reingold et al., 2013, New Disease Reports 28).

CGMMV is responsible for severe economic losses worldwide in particular in Cucurbitaceae and Solanaceae. In watermelon fields in Israel CGMMV disease caused total yield losses in some areas. (Reingold et al., 2016, Annals of Applied Biology 168, 29-40).

Park et al. (2005, Plant Cell Rep 24, 350) disclose transgenic *Citrullus lanatus* subspecies gongdae (wild watermelon) plants which have been made resistant to CGMMV by introduction of a cDNA encoding a CGMMV coat protein. *Citrullus lanatus* subspecies gongdae is not used as breeding material for commercial watermelon but it is used sometimes as rootstock in graftings of commercial watermelon. It is suggested that the CGMMV resistant transgenic Gongdae watermelon can be used as rootstock for producing non-transgenic commercial watermelon by grafting scions of a commercial watermelon to the transgenic Gongdae rootstock.

Lin et al. (2012, Transgenic Res 21, 983-993) disclose transgenic watermelon plants (hybrid cultivar Feeling) having been transformed with a single gene silencing construct targeting coat proteins of three different viruses, Cucumber mosaic virus (CMV), Cucumber green mottle mosaic virus (CGMMV) and Watermelon mosaic virus (WMV). Transformed plants resistant to all three viruses were identified in the first generation of transgenic lines (Ro). Resistance to CGMMV however was lost in the RI lines obtained by self-pollination of Ro lines, although resistance to the other two viruses was maintained. *Citrullus colocynthis* plants have been described in the art to be susceptible to CGMMV (Horvath, 1985, Acta Phytopathologica Academiae Scientiarum Hungaricae 20(3-4), 225-251).

Control of CGMMV is difficult as all commercial cultivars are susceptible. Using CGMMV resistant cultivars would be the best option for the management of the virus. However, development of resistance to CGMMV in different cucurbits through classical breeding has limitations because sources of host resistance are known only in melon and wild *Cucumis* spp. (Mandal et al., 2008, Plant Viruses 2(1), 25-34).

The problem to be solved by the present invention is the provision of sources for CGMMV resistance and the provision of commercial *Citrullus* plants being resistant to CGMMV. In one aspect the CGMMV resistant *Citrullus* plants are watermelon plants of the species *Citrullus lanatus* ssp *vulgaris*. A first aspect of the invention concerns a non-genetically engineered *Citrullus* plant cell or a non-genetically engineered *Citrullus* plant or plant part being resistant to CGMMV. Preferably the *Citrullus* plant cell or the *Citrullus* plant is a non-genetically engineered *Citrullus* crop plant cell or a non-genetically engineered crop plant being resistant to CGMMV.

No *Citrullus* source conferring resistance to CGMMV has been described. During screening of a large set of germplasm of various *Citrullus* accessions, a *Citrullus colocynthis* accession resistant to CGMMV was surprisingly detected. It produced small round fruits (about 4 cm wide and 4 cm long) with white flesh or pulp and a low brix (brix of about 2.0). A resistant plant (which showed no symptoms, score 4 in the test described herein) was selected from a heterozygous and/or heterogeneous seed sample (obtained from the US National Plant Germplasm collection, ars-grin.gov) and the resistance was selected and stabilized in selfing progenies, self-fertilized for several generations. A representative sample of seeds of the selected and stabilized *C. colocynthis* plant containing the CGMMV resistance was deposited by Nunhems B.V. under accession number NCIMB 42624, under the Budapest Treaty.

To date this is the first material with CGMMV resistance described in the genera *Citrullus*. *Citrullus colocynthis* can be crossed with other *Citrullus* species like e.g. *Citrullus lanatus*. Therefore, respective CGMMV resistant plants now for the first time make it possible to transfer the CGMMV resistance-conferring chromosomal fragment or fragments (comprising a CGMMV resistance locus) from the resistant "donor" plant to other *Citrullus* plants (also referred to as the "recipient" plants). Thus, the CGMMV resistant *Citrullus colocynthis* plants disclosed herein for the first time enable the production of *Citrullus* crop plants, such as cultivated watermelon (*C. lanatus* ssp *vulgaris*), resistant to CGMMV. This will be of great advantage for the farmer because the significant yield reductions caused by CGMMV in susceptible crop plants can now be reduced or avoided by cultivating CGMMV resistant *Citrullus* crop species.

It is well established that CGMMV is, besides other possibilities, also transmitted by contaminated seeds. Another advantage of the present invention therefore is for seed producers who will be able to avoid discarding seeds produced from fields where CGMMV infected plants appeared. In cucumber some CGMMV resistant varieties still carry the virus and enable significant virus multiplication in the plant, for example variety Bonbon of Rijk Zwaan (i.e. they are symptomless carriers and can thus spread the virus to other plants). The present resistance seems to prevent virus multiplication in the plant or at least reduce virus levels to very low levels, as seen in the Examples (see e.g. Table 2, showing that 15 dpi, 35 dpi and 60 dpi after mechanical leaf inoculation with CGMMV, the leaves contain no or extremely low levels of virus RNA, while the positive control contains significant amounts of virus RNA). The virus level is in one embodiment of the invention so low, that it does not cause CGMMV infection of nearby susceptible watermelon varieties and/or does not result in transmission of the virus to the seed produced in the fruits of such plants. This is also shown in the Examples.

Furthermore, the expenditure of work by seed producers and farmers can be reduced because for growing the CGMMV resistant *Citrullus* plants a number of precautionary measures, like e.g. disinfection of tools for field treatment and plant trimming become superfluous. In particular, as CGMMV is able to survive long time in soil, the provision of CGMMV resistant *Citrullus* plants will make it possible to regrow further generations of *Citrullus* plants (including e.g. grafted plants comprising a scion and/or rootstock of a CGMMV resistant plant according to the invention) in the same area or field, even when CGMMV was detected in the respective area before.

"Genetically engineered", as used herein means the direct modification of an organism's genome using biotechnology by altering the genetic make-up of an organism by techniques that introduce nucleic acids prepared outside the organism either directly into a host or introduce nucleic acids prepared outside the organism into a cell which cell is then fused, crossed or hybridized with the final host. Genetic engineering involves recombinant nucleic acid (DNA or RNA) techniques followed by the incorporation of recombinant nucleic acids either indirectly like by means of a vector system or directly like by means of particle bombardment, micro-injection, macro-injection and micro-encapsulation techniques. "Non-genetically engineered" as used herein means modification of an organism's genome and/or altering the genetic make-up of an organism using techniques that do not include introduction of nucleic acids prepared outside the organism into the organism.

"CGMMV" is used herein as abbreviation for Cucumber Green Mottle Mosaic Virus.

"Resistant to CGMMV" as used herein means that plants or plant parts of a line or variety when inoculated with CGMMV do not show visual CGMMV symptoms on leaves (scale 4) (and preferably also no symptoms inside the fruits); or in one aspect plants show mild symptoms (very mild mosaic and few clearing spots) on leaves (scale 3) (and preferably the fruits of those plants do not show any symptoms inside and are still marketable), while the susceptible control line or variety (e.g. Sugar Baby or other CGMMV susceptible varieties) shows severe symptoms on leaves (Scale 1) and symptoms inside the fruits when tested under the same conditions. Preferably a plant line or variety is considered to be resistant if at least 93%, 94%, 95%, 96%, 97%, 98%, 99% or 100% of the plants of a line conform to the above mentioned scale (preferably at least 10, 15, 20, 25, 30 or more plants of a line are tested alongside the appropriate control lines). Symptoms inside the fruits are symptoms which make the mature fruit not suitable for human consumption, e.g. deterioration of the pulp and/or water soaking of the pulp. A suitable test for assessing the visual CGMMV symptoms is for example the mechanical leaf inoculation method described in the Examples in General Methods Items 1-3 and below.

"Visually CGMMV symptoms" on leaves are classified herein according to the following:

Scale 1: Severe symptoms: leaf deformation, blistering and clear mosaic

Scale 2: Medium symptoms: mild leaf deformation but clear mosaic

Scale 3: Mild symptoms: very mild mosaic and few clearing spots

Scale 4: No symptoms on leaves

In one aspect, "resistant to CGMMV" encompasses that the plants and plant parts showing no symptoms on the leaves (scale 4) and preferably also not inside the fruits, optionally showing mild symptoms on the leaves (scale 3) and preferably no symptoms inside the fruits, contain a significantly lower average virus level (or virus titer) in the leaves (and optionally also in the fruits) at 15 dpi, 30 dpi, 35 dpi, 60 dpi and/or 90 dpi (or later) than the susceptible control line or variety. "Significantly lower" refers herein to an average virus level, detectable by e.g. RT-qPCR, which is at least 100 fold lower, preferably at least 1000 fold lower, more preferably at least 5000 fold, or at least 10000 fold, or at least 50000 fold, or at least 100000 fold lower than in the susceptible control tissue. In one aspect the CGMMV virus level, detectable by RT-qPCR, is in the leaves and preferably also in the fruits of the resistant plant below an average concentration of $1.5 \times 10^{-4}$ ng/µl or below $1.3 \times 10^{-4}$ ng/µl at 15 dpi, 30 dpi, 35 dpi, 60 dpi and/or 90 dpi; in one aspect the average virus level is even lower, e.g. below $5 \times 10^{-5}$ ng/µl, or below $4 \times 10^{-5}$ ng/µl, or below $3 \times 10^{-5}$ ng/µl, or below $2 \times 10^{-5}$ ng/µl. Especially in one aspect the average virus titer is below $5 \times 10^{-5}$ ng/µl at 15 dpi and/or below $3 \times 10^{-5}$ ng/µl at 35 dpi and/or below $2 \times 10^{-5}$ ng/µl at 60 dpi or later, or even undetectable using RT-qPCR (or TaqMan assay) while the susceptible control shows severe symptoms and contains a significantly higher virus level (e.g. at least 100 fold higher, preferably at least 1000 fold higher) under the same conditions and at the same time point. In one aspect the average virus titer decreases over time in the resistant tissue, i.e. the titer is lower at 35 dpi than at 15 dpi and is lower at 60 dpi than at 35 dpi.

In one aspect also the virus transmission from a CGMMV resistant plant of the invention to other watermelon plants, e.g. susceptible watermelon plants, is less than 1%, preferably less than 0.5%, more preferably 0%. Virus transmission can for example be tested as described in the examples, by using leaves of CGMMV resistant plants that had been inoculated with CGMMV as inoculum to inoculate other plants and to determine the percentage of other plants that are infected. In a further aspect the seeds produced in fruits of the CGMMV resistant plants of the invention are free of CGMMV virus. Again, this can be tested as described in the Examples.

"*Citrullus*" or "*Citrullus* plant" as used herein means a plant of the Cucurbitaceae family belonging to the genus *Citrullus*.

The genus *Citrullus* comprises four or five species: *Citrullus lanatus* (including subspecies *lanatus*, *vulgaris* and *mucosospermus*), *Citrullus colocynthis* and the wild species *Citrullus ecirrhosus* and *Citrullus rehmii* (Levi et al., 2001, Genetic Resources and Crop Evolution 48, 559-566). *Citrullus naudinianus*, a fifth *Citrullus* species is so different from the other *Citrullus* species in gross morphology that some artisans place it into the genus *Acanthosicyos* (*A. naudinianus*). In connection with the present invention *Citrullus naudinianus* shall be understood to represent a *Citrullus* species. *Citrullus lanatus* subspecies *vulgaris* is commonly designated in the art as cultivated watermelon, representing the most widely cultivated watermelon crop plant. Thus, reference herein to 'cultivated watermelon' refers to *Citrullus lanatus* ssp. *vulgaris* crop plants, e.g. lines or varieties. Each of the five *Citrullus* species has a diploid (2n) chromosome number of 22. The five mentioned different *Citrullus* species are crossable with each other and thus, CGMMV resistance can be transferred between these species, e.g. by breeding processes. (Kun-Peng Li et al., 2016, BMC Evolutionary Biology 16, 85).

"*Citrullus* plant cell" means a plant cell which originates from, is obtainable by, obtained, derived or derivable from a *Citrullus* plant or any part thereof. The cell can be eligible to be regenerated into a whole plant (regenerable plant cell) or it can be a cell not eligible to be regenerated into a whole plant (non-regenerable plant cell). Likewise, a "*Citrullus lanatus* ssp *vulgaris* plant cell" means a plant cell which originates from, is obtainable by, obtained, derived or derivable from a *Citrullus lanatus* ssp. *vulgaris* plant or any part thereof. The cell can be eligible to be regenerated into a whole plant (regenerable plant cell) or it can be a cell not eligible to be regenerated into a whole plant (non-regenerable plant cell).

In connection with the present invention the term "crop plant" has the common meaning and is to be understood to be any specific plant or variety which is intended to be grown or cultivated in a scale for profit or subsistence and which after growing is harvested for food, clothing, livestock, fodder, biofuel, medicine, or other uses by humans. In particular the term "crop plant" has the meaning herein to be any specific plant which is intended to be grown or cultivated in groups on a scale for profit and which after growing is harvested for providing food. By the term intended to be grown used in the current definition it shall be made explicitly clear that also any breeding material eligible for producing any specific plant which is intended to be grown or cultivated in groups on a scale for profit and which after growing is harvested for providing food is comprised by the term "crop plant" as used herein.

"*Citrullus* crop plants" herein comprise plants of the species *Citrullus lanatus* (including subspecies *vulgaris*, *mucosospermus* or *lanatus*), *Citrullus colocynthis* and *Citrullus naudinianus*.

Crop plants comprise the term cultivated plants. In respect to watermelon plants the term "cultivated plant" is commonly used in the art and to be understood herein to represent plants of *Citrullus lanatus* subspecies *vulgaris* (Kun-Peng Li et al., 2016, BMC Evolutionary Biology 16, 85).

The term "food" has the common meaning herein and is to be understood to be any nourishing substance that is eaten, drunk, or otherwise taken into the human body.

The *Citrullus* crop plant species *Citrullus lanatus*, *Citrullus colocynthis* or *Citrullus naudinianus* are crossable with each other, enabling the transfer or introgression of CGMMV resistance from one of those species into another one of those species. The CGMMV resistance of the *Citrullus colocynthis* plant provided by the invention, e.g.

plants obtained, derived, derivable from or obtainable by or originating from seeds deposited under accession number NCIMB 42624 can therefore be introgressed into other *Citrullus colocynthis* plants (e.g. susceptible to CGMMV), into *Citrullus lanatus* species (e.g. into cultivated watermelon) or into *Citrullus naudinianus* species.

A preferred embodiment of the invention therefore concerns a non-genetically engineered *Citrullus* plant cell or plant according to the invention, wherein the plant cell or the plant according to the invention is selected from the group of species consisting of *Citrullus lanatus, Citrullus colocynthis* or *Citrullus naudinianus*. In a more preferred embodiment of the invention the non-genetically engineered *Citrullus* plant cell or plant according to the invention is a *Citrullus lanatus* plant cell or a *Citrullus lanatus* plant, most preferably a *Citrullus lanatus* subspecies *vulgaris* plant cell or a *Citrullus lanatus* subspecies *vulgaris* plant.

Seeds of a CGMMV resistant *Citrullus colocynthis* plant from which *Citrullus colocynthis* plant cells, and one or more CGMMV resistance QTLs, can be obtained have been deposited under accession Number NCIMB 42624 or progeny thereof, especially selfings thereof. From these deposited seeds, CGMMV resistant *Citrullus colocynthis* plants, from which *Citrullus colocynthis* plant cells can be obtained, can be grown. Likewise one or more *C. colocynthis* QTLs (Quantitative Trait Loci) conferring CGMMV resistance are obtainable from these seeds or progeny thereof, whereby the progeny retain one or more or all of the QTLs.

The inventors have found five QTLs in *C. colocynthis* which confer CGMMV resistance and which can be transferred individually or in different combinations from the *C. colocynthis* donor (e.g. NCIMB 42624 or progeny thereof or optionally another CGMMV resistant *C. colocynthis* plant which comprises the QTL or QTLs) to other plants, e.g. into cultivated watermelon. The five QTLs are described in details herein. Fine mapping will be done to narrow down the chromosome region where the QTLs are found. This enables shorter introgression fragments to be used, thereby eliminating linkage drag (introgression of undesired traits linked to the QTL) from the donor.

In one specific embodiment the invention therefore concerns *Citrullus colocynthis* seeds deposited under accession number NCIMB 42624 or plants grown from seeds deposited under accession number NCIMB 42624 or progeny (descendants) of such plants, especially selfing progeny, e.g. which comprise a CGMMV resistance score of 4 (no symptoms). *Citrullus colocynthis* plant cells or *Citrullus colocynthis* plants obtained, derived, derivable from or obtainable by or originating from seeds deposited under accession number NCIMB 42624 or *Citrullus colocynthis* plant cells obtained, derived, derivable from or obtainable by or originating from plants grown from seeds deposited under accession number NCIMB 42624 are accordingly one specific embodiment of the invention.

In another specific embodiment the invention concerns *Citrullus* plants, especially cultivated watermelon plants, comprising one or more CGMMV resistance QTLs (as described herein) originating from/derivable from/as found in/obtained from/derived from *Citrullus colocynthis* seeds deposited under accession number NCIMB 42624 or plants grown from seeds deposited under accession number NCIMB 42624 or progeny (descendants) of such plants.

In yet another specific embodiment the invention concerns *Citrullus* plants, especially cultivated watermelon plants, comprising one or more CGMMV resistance QTLs (as described herein) originating from/derivable from/as found in/obtained from/derived from a CGMMV resistant *Citrullus colocynthis* plant or seed, which plant or seed comprises the same QTL or QTLs as present in seeds deposited under accession number NCIMB 42624 or plants grown from seeds deposited under accession number NCIMB 42624 or progeny (descendants) of such plants. Such a *Citrullus colocynthis* plant comprises CGMMV resistance score of 4 and comprises one or more or all of the SNP markers linked to the QTL or QTLs. So for example, the *C. colocynthis* plant may comprise QTL7.1 and therefore also one or more or all of the SNP markers linked to QTL7.1, as described further below and e.g. in Table 1 and Table 6. So, for example, in one aspect the *Citrullus colocynthis* plant comprises QTL7.1 and/or QTL9.1, preferably it comprises the resistant donor nucleotide for SNP13, SNP14 and/or SNP15 linked to QTL7.1 and/or the resistant donor nucleotide for SNP22, SNP23 and/or SNP24 linked to QTL9.1. In another aspect the *Citrullus colocynthis* plant comprising QTL1.1, QTL4.1, QTL5.2, QTL7.1 and/or QTL9.1 preferably comprises the resistant donor nucleotide for SNP4, SNP5 and/or SNP 6 linked to QTL1.1, and/or the resistant donor nucleotide for SNP7, SNP8 and/or SNP9 linked to QTL4.1, and/or the resistant donor nucleotide for SNP10, SNP11 and/or SNP12 linked to QTL5.1, and/or the resistant donor nucleotide for SNP13, SNP14 and/or SNP15 linked to QTL7.1 and/or the resistant donor nucleotide for SNP22, SNP23 and/or SNP24 linked to QTL9.1.

Preferably the invention concerns non-genetically engineered *Citrullus* plant cells or plants according to the invention comprising an introgressed resistance to CGMMV, preferably non-genetically engineered *Citrullus* plant cells or plants according to the invention comprise resistance to CGMMV introgressed into their genome.

In a more preferred embodiment the invention concerns non-genetically engineered *Citrullus* plant cells or plants according to the invention, wherein the introgressed resistance to CGMMV is obtained, derived, derivable from or obtainable by or originates from a *Citrullus* plant or a *Citrullus* plant cell, more preferably resistance to CGMMV is obtained, derived, derivable from or obtainable by or originates from a *Citrullus colocynthis* plant cell or a *Citrullus colocynthis* plant, especially from a *Citrullus colocynthis* plant of which a representative sample of seeds has been deposited under accession number NCIMB 42624, or a CGMMV resistant descendant thereof (e.g. obtained by selfing). SNP marker analysis or sequencing of the chromosome region comprising the QTL or QTLs can be used to determine if the CGMMV resistance is 'as in' or as obtainable from the deposited seeds.

Even more preferably the non-genetically engineered *Citrullus* plant cell or plant according to the invention is a *Citrullus lanatus* subspecies *vulgaris* plant cell or is a *Citrullus lanatus* subspecies *vulgaris* plant comprising introgressed into its genome resistance to CGMMV, wherein the introgressed resistance to CGMMV is 'as present in', obtained, derived, derivable from or obtainable by or originates from a *Citrullus colocynthis* plant cell or a *Citrullus colocynthis* plant, respectively, especially from a *Citrullus colocynthis* plant or cell of which a representative sample of seeds has been deposited under accession number NCIMB 42624, or a CGMMV resistant descendant thereof (e.g. obtained by selfing). In one aspect, the *Citrullus colocynthis* donor from which CGMMV resistance can be obtained is a donor accession which produces no symptoms (scale 4) when inoculated mechanically with CGMMV as described in the Examples and/or wherein the virus titer at various time points after inoculation is significantly reduced compared to the susceptible control, e.g. the titer is less than $5 \times 10^{-5}$ ng/μl using a RT-qPCR (TaqMan) assay and/or comprises one or more or all of QTL1.1, QTL4.1, QTL5.2, QTL7.1 and/or QTL9.1 and thus one or more of the resistant donor nucleotides of the SNP markers linked to the respective QTLs. In one aspect the donor is NCIMB 42624 or a progenitor or progeny of this plant.

In an even more preferred embodiment the invention concerns non-genetically engineered *Citrullus* plant cells or plants according to the invention, wherein the introgressed resistance to CGMMV is 'as present in', obtained from, or derived from, or obtained, derived, derivable from or obtainable by or originates from a seed or a cell of a seed deposited under accession number NCIMB 42624, or a CGMMV resistant descendant thereof (e.g. obtained by selfing), or is obtained, derived, derivable from or obtainable by or originates from a plant grown from said deposited seed or descendant thereof or is obtained, derived, derivable from or obtainable by or originates from a plant cell obtained from or obtainable by the plant grown from said deposited seed or descendant thereof. Thus, in one aspect the plant cell or plant comprises one or more CGMMV resistance conferring introgression fragments from a CGMMV resistant donor plant, e.g. from a *Citrullus colocynthis* plant of which a representative sample of seeds has been deposited under accession number NCIMB 42624, or a CGMMV resistant descendant thereof (e.g. obtained by selfing).

In an even further more preferred embodiment the non-genetically engineered *Citrullus* plant cell or plant according to the invention is a *Citrullus lanatus* subspecies *vulgaris* plant cell or a *Citrullus lanatus* subspecies *vulgaris* plant comprising introgressed resistance to CGMMV, wherein the introgressed resistance to CGMMV is obtained, derived, derivable from or obtainable by or originates from a seed or a cell of a seed deposited under accession number NCIMB 42624, or a CGMMV resistant descendant thereof (e.g. obtained by selfing), or is obtained, derived, derivable from or obtainable by or originates from a plant grown from said deposited seed or grown from a CGMMV resistant descendant of the deposited seed (e.g. obtained by selfing), or is obtained from or obtainable by or originates from a plant cell obtained from or obtainable by the plant grown from said deposited seed or grown from a CGMMV resistant descendant of the deposited seed (e.g. obtained by selfing). Thus, in one aspect the plant cell or plant is a cultivated watermelon plant cell or plant which comprises in its genome one or more resistance conferring introgression fragments (wherein said fragment or fragments comprise a CGMMV resistance locus, especially one or more QTLs) from a CGMMV resistant donor plant, e.g. from a *Citrullus colocynthis* plant of which a representative sample of seeds has been deposited under accession number NCIMB 42624, or a CGMMV resistant descendant thereof (e.g. obtained by selfing). The presence of one or more resistance-conferring introgression fragments in the recipient plant or plant cell can be detected by methods known to the skilled person e.g. whole genome sequencing, molecular marker analysis, QTL mapping of the resistance locus, and/or other methods, such as phenotypic analysis, allelism tests, etc. Likewise, the presence of one or more resistance conferring introgression fragments in the recipient plant or plant cell can be detected by the markers physically linked to the QTLs identified in the *C. colocynthis* donor herein.

The wild, desert plant species *C. colocynthis* is diploid and has 2n=22 chromosomes, corresponding to those of the cultivated watermelon, whereby introgression from a fragment of a *C. colocynthis* chromosome to the corresponding *C. lanatus* ssp *vulgaris* chromosome is feasible. In *C. colocynthis* accession number NCIMB 42624 five QTLs were found which confer resistance to CGMMV, e.g. when introgressed into to cultivated watermelon susceptible to CGMMV. The location of these QTLs in the genome was determined and SNP markers linked to the QTL were found. The *C. colocynthis* donor was homozygous for all of the SNP nucleotides, as can be seen from the SNP genotype of the diploid donor. The five QTLs are named QTL1.1, present on chromosome 1, QTL4.1 present on chromosome 4, QTL5.2 present on chromosome 5, QTL7.1 present on chromosome 7 and QTL9.1 present on chromosome 9 of the sequenced cultivated watermelon genome. The region where each of the QTLs is found is delimited by the SNP (Single Nucleotide Polymorphism) markers listed in the Table 1 below. When the sequences are used in a BLAST analysis against the "Watermelon (Charleston Gray) Genome" found on the world wide web at cucurbitgenomics.org, the nucleotide position of the single polymorphism in the watermelon genome is found. The SNP marker most closely linked to the QTLs is indicated in the Table. As the regions delimited by the SNP markers are quite large obviously not the entire region delimiting each QTL needs to be introgressed into cultivated watermelon, but only the sub-region comprising the QTL and conferring CGMMV resistance can be introgressed into other *Citrullus* plants, especially into cultivated watermelon.

TABLE 1

| Cultivated watermelon chromosome (Chr) | Nucleotide position of the SNP in the watermelon genome (base number); | SNP marker linked to QTL (most closely linked marker is indicated) | Nucleotide sequence with SNP indicated as [X/Y]; X is nucleotide of CGMMV resistant donor; Y is nucleotide of the susceptible recurrent parent | SNP genotype of CGMMV resistant donor |
|---|---|---|---|---|
| Chr1 (QTL1.1) | 6,555,391 | SNP1 refers to nucleotide 51 in SEQ ID NO: 1 | AAGTACAGTTGCAAATATAATAATCAGG TTTAAAATATTTGCAAATATAG[C/T]AAA ATTTAGATTCTGCTTTTAAAGTCTAACAG TGATAGACCATATCAGTG (SEQ ID NO: 1) | CC |
| Chr1 (QTL1.1) | 16,631,610 | SNP2 refers to nucleotide 51 in SEQ ID NO: 2 | GGAAAAAGAAATTACATGGAATGCATC GTTATTGTTTCATTTATATCCCC[G/A]TAT AGATCAATGTAAACTTGAAGTTCGGAAA ATAATTCATTTGCAAAATA (SEQ ID NO: 2) | GG |

TABLE 1 -continued

| Cultivated watermelon chromosome (Chr) | Nucleotide position of the SNP in the watermelon genome (base number); | SNP marker linked to QTL (most closely linked marker is indicated) | Nucleotide sequence with SNP indicated as [X/Y]; X is nucleotide of CGMMV resistant donor; Y is nucleotide of the susceptible recurrent parent | SNP genotype of CGMMV resistant donor |
|---|---|---|---|---|
| Chr1 (QTL1.1) | 26,238,488 | SNP3 refers to nucleotide 51 in SEQ ID NO: 3 | TTGTTAGTGCAACAAATGTGTAGACATG CATAAAACACTTGTTAGTGCAA[C/]GA ATGTGTTAGACATATATGACAATAATAA AAAAATTTGAATATGAAAAT (SEQ ID NO: 3) | CC |
| Chr1 (QTL1.1) | 34,609,471 | SNP4 refers to nucleotide 51 in SEQ ID NO: 4 | GGCGGAACGCCGACCGGAAGGTTTAGC AACGGCAAAATCCCCACCGATTT[C/T]GT AGGTGGGGCTCCTAATAATTCATTTTAT CTCTCCTCTAATAACATTTT (SEQ ID NO: 4) | CC |
| Chr1 (QTL1.1) | 35,238,267 | SNP5 refers to nucleotide 51 in SEQ ID NO: 5 (most closely linked) | CTCTACATTAGAGAGGACTTTGAAGTTG TTGACAGGAAAACATGGCTGCA[G/A]GC AAGTTACTTTTAGCCCCAAGTTTTTAGTG GTTGATGTCTCTTTTAAAT (SEQ ID NO: 5) | GG |
| Chr1 (QTL1.1) | 35,766,439 | SNP6 refers to nucleotide 51 in SEQ ID NO: 6 | TCTATTTTGCGTTCCACTCTTCGCATTCT CTCTTCTACAAGAAAATAGCC[T/C]CTAT TCTATCTTCATTTAGGGGCTTTCTTTCTT ATAACTTTCATCTAGGG (SEQ ID NO: 6) | TT |
| Chr4 (QTL4.1) | 4,230,711 | SNP7 refers to nucleotide 51 in SEQ ID NO: 7 | AATTTTGAACCTGATATAAACTCAACAT CATTGATTAGATCGCAAACTTC[T/A]GTT TGTTCTCAAGCTTCTTTCATTGAATCCAA ATATTGAGTAAAATACAC (SEQ ID NO: 7) | TT |
| Chr4 (QTL4.1) | 24,321,690 | SNP8 refers to nucleotide 51 in SEQ ID NO: 8 (most closely linked) | TTGGCGTGGGCTTGTACCATATAGTGTTT GCCTTCAAGTGATTGCAATTT[C/A]TAGT TCAATCTTGAGTTTGGTATTCAATACTG AAAGCCTCATTGCCATT (SEQ ID NO: 8) | CC |
| Chr4 (QTL4.1) | 25,526,846 | SNP9 refers to nucleotide 51 in SEQ ID NO: 9 | TTTATTTGTCAATTTCATCAGCAAAATTG TCTTGAAAATTGATGCTTAGC[A/G]TACC TTTTCTTTCTAGAAATGCTTCAAAACCTC CGGGTTCAATGGCGCAG (SEQ ID NO: 9) | AA |
| Chr5 (QTL5.2) | 30,786,503 | SNP10 refers to nucleotide 51 in SEQ ID NO: 10 | AGATCAGATGCATTTACGTCCGGCTTCA CTTCATTTTGAGTAGAGTTCAC[T/C]GTT ATTTTGTTGATGGATTCGCCCGAGATAA CACCAGACTTTTCTGGAGA (SEQ ID NO: 10) | TT |
| Chr5 (QTL5.2) | 32,788,817 | SNP11 refers to nucleotide 51 in SEQ ID NO: 11 (most closely linked) | GAAGGGGCAATTGAACCCCTTGTCCAAA TGTTCCGTACTGAAAAGCTTGA[A/G]GCT AAATTATCGGCATTAAGCGCATTGCAAA GCCTCTCAGGCTTGAAGGA (SEQ ID NO: 11) | AA |
| Chr5 (QTL5.2) | 36,842,501 | SNP12 refers to nucleotide 51 in SEQ ID NO: 12 | TAATGTGCCGAACTCCAAATATTAAGGC ACAAGGTTATGGTGTGGTGG[T/C]GCT GAATGTACCACATTCTACGCCATGCTAT TCCTAACTTAAACCAGCCT (SEQ ID NO: 12) | TT |
| Chr7 (QTL7.1) | 4,784,519 | SNP13 refers to nucleotide 51 in SEQ ID NO: 13 | GAGTTTTTCAAGTGATGATTTGAGTTGG GAGATCTGAGAGCCTTGGACAT[A/G]AG TGTTTCTCCTGTACATTTTTTGTTGTTGG TTCACTAGATTGTTGTTCT (SEQ ID NO: 13) | AA |
| Chr7 (QTL7.1) | 7,848,633 | SNP14 refers to nucleotide 51 in SEQ ID NO: 14 (most closely linked) | TTTCGAGAAGACTTATCTCATACAATAG TATATGAGCTGAACTACTAGAG+A/G+AA CATCAATCACAAACTTTCATCTGTTAAA TCTTAGAAGAACTGGTTTGG (SEQ ID NO: 14) | AA |

TABLE 1 -continued

| Cultivated watermelon chromosome (Chr) | Nucleotide position of the SNP in the watermelon genome (base number); | SNP marker linked to QTL (most closely linked marker is indicated) | Nucleotide sequence with SNP indicated as [X/Y]; X is nucleotide of CGMMV resistant donor; Y is nucleotide of the susceptible recurrent parent | SNP genotype of CGMMV resistant donor |
|---|---|---|---|---|
| Chr7 (QTL7.1) | 8,334,624 | SNP15 refers to nucleotide 51 in SEQ ID NO: 15 | TGACCACCCAAATATTTTCCAAATTTGC AGATTTTTTCAAAAAATGAAAG[G/A]TA GCGCAACTGCGCTCTAAAAGAGCATAGC TACACTTTGGGAATTTTTTC (SEQ ID NO: 15) | GG |
| Chr7 (QTL7.1) | 11,166,694 | SNP16 refers to nucleotide 51 in SEQ ID NO: 16 | ACTTTGTTTTTCTTCAATTCTCTCTAAAT TTATCATTCTAGATCACCTAT[G/T]ATCT TTAATGCCCTGGAACTGTAAAAATAAAT TGTAATTTAAAGGAGTCA (SEQ ID NO: 16) | GG |
| Chr7 (QTL7.1) | 18,775,728 | SNP17 refers to nucleotide 51 in SEQ ID NO: 17 | GGTGGTGCTGGTGATGTTGTTGATGTTA AGATTAAAGGCTCTTCTACTGG[T/C]TGG CTTCAAATGTCAAGGAATTGGGGTCAAA ATTGGCAGGTTGGTACCTT (SEQ ID NO: 17) | TT |
| Chr7 (QTL7.1) | 21,389,410 | SNP18 refers to nucleotide 51 in SEQ ID NO: 18 | ATAAAATTAAATGAAAACGCCTTAGAAA CATCAGAGAATTCATTTCTCCA[A/G]AAG GAAGAAGAATTCTGCAATAGAATCCTAG AGTTGGAGAACAGACTGGA (SEQ ID NO: 18) | AA |
| Chr9 (QTL9.1) | 31,394,464 | SNP19 refers to nucleotide 51 in SEQ ID NO: 19 | CGTCGGAGTTGGGCCTTAAGGCGAATGT TAGTGTTGGTTGACAGATGGTT[C/T]TCA TTGGAGTTGATCATCCAAGGTGGTCGTT GGAGCATGAAGTTGTTCGG (SEQ ID NO: 19) | CC |
| Chr9 (QTL9.1) | 32,499,549 | SNP20 refers to nucleotide 51 in SEQ ID NO: 20 | AAAGATGGAGAGGATCTTTGTAGGTTGC ACGACCAACGCTTCCATTGGGA[G/C]GC ATGTCTCTCTGGTTCATGGTAAGCTGAA TGACATTGTTGGAAGGGTAT (SEQ ID NO: 20) | GG |
| Chr9 (QTL9.1) | 34,607,108 | SNP21 refers to nucleotide 51 in SEQ ID NO: 21 | GCCTCAACTTCGTTTCTTTTTTCTCTTTCT ITTATAGTTCCTCTACTATT[G/]CTCCTT CTGTATCTCCTGCTGAGTTCTTTTGCTCT AACAACCAATTTTCT (SEQ ID NO: 21) | GG |
| Chr9 (QTL9.1) | 35,343,850 | SNP22 refers to nucleotide 51 in SEQ ID NO: 22 (most closely linked) | TTATCAAGAGATCCATATAAGTATGTTG TCTACATCCATAAGATGCATGT[C/T]CAG ATTTTCATTCACAGTCAGACTAATTAAA TATCTTAATGTAATTGCAT (SEQ ID NO: 22) | CC |
| Chr9 (QTL9.1) | 36,923,004 | SNP23 refers to nucleotide 51 in SEQ ID NO: 23 | AATAAATAGTACAAATATCAATTTATAC CCTAAACGATTTAAACCCCAAA[C/T]TA ATAGTTGTATCAATTAAAACCATAAATT TTCATTAGTGTATCAATTTA (SEQ ID NO: 23) | CC |
| Chr9 (QTL9.1) | 38,321,162 | SNP24 refers to nucleotide 51 in SEQ ID NO: 24 | AAGGTAGGGTTTGGCCTTCAGGATAGTG ACGACATTGATGCGTTGTTTGT[G/T]AAA TCTGTGGAGGAGGTTCCGTATAATATCT CTGTGATTCAGATCAGTAA (SEQ ID NO: 24) | GG |

The SNP genotype of the diploid CGMMV resistant donor (e.g. NCIMB42624) is provided in the right column. The resistant donor nucleotide of each SNP is, thus, the nucleotide mentioned in that column, so e.g. the SNP donor nucleotide for SNP1 refers to nucleotide 'C' (Cytosine) at nucleotide 51 in SEQ ID NO: 1, etc.

QTL7.1 and QTL9.1 are dominant and therefore confer resistance when the locus is in heterozygous or homozygous form. These two QTLs are the most important in conferring CGMMV resistance, as not only CGMMV symptoms are reduced to a scale of 3 (mild symptoms) or 4 (no symptoms), but also the virus titer (level) is significantly reduced to extremely low levels (e.g. less than $5\times10^{-5}$ ng/µl at one or more time-points after inoculation) or even not detectable levels. The other three QTLs, QTL1.1, QTL4.1 and QTL5.2 are recessive loci and (without limiting the scope of the invention) appear to play a role in affecting virus titer in the plants.

In one aspect *Citrullus* plants are provided, preferably cultivated watermelon plants, wherein the plant or plant cell comprises one or two or three or four or five QTLs (introgression fragments from a *C. colocynthis* donor, e.g. from NCIMB 42624 or other CGMMV resistant *C. colocynthis* donors having e.g. a score of 4 and comprising the QTL) selected from the group consisting of QTL1.1, QTL4.1, QTL5.2, QTL7.1 and QTL9.1.

In another aspect *Citrullus* plants are provided, preferably cultivated watermelon plants, wherein the plant or plant cell comprises one or two or three or four QTLs (introgression fragments from a *C. colocynthis* donor, e.g. from NCIMB 42624 or other CGMMV resistant *C. colocynthis* donors having e.g. a score of 4 and comprising the QTL) selected from the group consisting of QTL1.1, QTL4.1, QTL7.1 and QTL9.1.

In yet another aspect *Citrullus* plants are provided, preferably cultivated watermelon plants, wherein the plant or plant cell comprises at least one or two QTLs (introgression fragments from a *C. colocynthis* donor, e.g. from NCIMB 42624 or other CGMMV resistant *C. colocynthis* donors having e.g. a score of 4 and comprising the QTL) selected from the group consisting of QTL7.1 and/or QTL9.1. In one aspect optionally one or more of the recessive QTLs, selected from QTL1.1, QTL4.1 and QTL5.2 may be combined with QTL7.1 and/or QTL9.1.

In one aspect the plant or plant cell is cultivated watermelon and comprises at least QTL7.1 and/or QTL9.1, optionally both in homozygous form.

The presence of the QTLs can for example be determined by the presence of the donor SNP nucleotide of one or more or all of the SNP markers linked to the QTL, or sequencing the chromosome regions to detect the nucleotide sequence of the introgression fragment and e.g. compare it to the nucleotide sequence of the donor.

A watermelon plant, plant part or plant cell which is said to "comprise a QTL" or "comprise an introgression fragment comprising a QTL" from a *C. colocynthis* donor if the chromosome sequence comprising the QTL has been introgressed onto the corresponding chromosome of cultivated watermelon to generate a recombinant chromosome. This is detectable by e.g. sequencing the chromosome region and/or by the introgression fragment comprising one or more or all of the donor SNP markers linked to the QTL. In addition, the CGMMV resistance should be transferred with the introgression fragment, i.e. confer the CGMMV resistance phenotype to a watermelon line, whereby the watermelon line lacking the introgression fragment is susceptible to CGMMV.

In respect to the origin of the introgressed CGMMV resistance it is not decisive if resistance to CGMMV is directly introgressed from a *Citrullus*, preferably *Citrullus colocynthis* plant cell or plant into the genome of a plant cell or plant according to the invention, preferably into a *Citrullus lanatus* subspecies *vulgaris* plant cell or into a *Citrullus lanatus* subspecies *vulgaris* plant. All what is decisive is that the introgressed resistance to CGMMV is obtained, derived, derivable from or obtainable by or originates from a *Citrullus*, preferably *Citrullus colocynthis* plant cell or plant, e.g. the donor deposited or another donor which has a resistance score of 4 (no symptoms). Resistance to CGMMV can e.g. first be introgressed from *Citrullus*, preferably *Citrullus colocynthis* into another species or subspecies like e.g. *Citrullus lanatus* (including subspecies *lanatus* and *mucosospermus*), *Citrullus ecirrhosus*, *Citrullus rehmii*, *Citrullus naudinianus* or another, non-CGMMV resistant *Citrullus colocynthis* plant cell or plant, before it is introgressed into a plant cell or plant according to the invention. It is also not decisive, if CGMMV resistance is introgressed into various different species or plants, before it is introgressed into a plant or crop plant cell according to the invention (e.g. a *Citrullus lanatus* subspecies *vulgaris* plant cell or plant). All what is decisive is that the CGMMV resistance introgressed into a plant cell or plant according to the invention (e.g. *Citrullus lanatus* subspecies *vulgaris* plant cell or plant) is originally obtained, derived, derivable from or obtainable by a *Citrullus*, preferably *Citrullus colocynthis* plant cell or plant. Thus, the origin of the chromosomal fragment introgressed into a crop plant or crop plant cell according to the invention (e.g. *Citrullus lanatus* subspecies *vulgaris* plant cell or plant) is what matters, but not the steps and/or the number of steps used in the introgression process or any other breeding process.

The term "introgression" used herein has the meaning common in the art and is to be understood to be the movement or introduction of chromosomal fragment or fragments from one plant (donor) into the gene pool of another plant of the same or a different species (recipient plant, sometimes called recurrent plant or recurrent parent). "Introgressed resistance to CGMMV" or "introgression fragment", accordingly means that chromosomal fragment or fragments conferring resistance to CGMMV, i.e. comprising a CGMMV resistance locus (QTL), were introduced from one CGMMV resistant plant cell or plant into another plant cell not resistant to CGMMV or into another plant not resistant to CGMMV. Introgression of CGMMV resistance into a plant may be implemented by crossing or traditional breeding techniques, including backcrossing, i.e. the introgressed CGMMV resistance can be the result of breeding methods. Introgression of CGMMV resistance into a recipient plant is a technical process directed by man. In particular introgression herein refers to a man-made breeding process or method. One or more or all of the molecular markers, e.g. SNP markers, provided herein can be used in that process. The resulting plant, i.e. the cultivated line or variety comprising one or more introgression fragments from a donor is also man-made and does not exist in nature.

The introgression fragment from *C. colocynthis* comprising the QTL can be large, e.g. even half of a chromosome, but is preferably smaller, such as about 20 Mb (Megabases), 18 Mb, 15 Mb or less, such as about 10 Mb or less, about 9 Mb or less, about 8 Mb or less, about 7 Mb or less, about 6 Mb or less, about 5 Mb or less, about 4 Mb or less, about 3.5 or 3 Mb or less, about 2 Mb or less, about 1 Mb (equals 1,000,000 base or less), or about 0.9 Mb (equals 900,000 base pairs) or less, such as 0.8 Mb, 0.7 Mb, 0.6 Mb, 0.5 Mb or less. In one aspect the introgression fragment comprises the elsewhere herein (see e.g. Table 1 and 6) indicated physical region comprising one or more of the SNP markers, or a sub-region thereof, which retains the respective QTL.

"CGMMV resistance locus" or "CGMMV resistance QTL" means the region on the chromosome, where a gene, and an allele of the gene, conferring CGMMV resistance is located. Therefore, when referring to an introgressed resistance to CGMMV, it is understood that the CGMMV resistance locus is introgressed, i.e. is present on the introgression fragment. The CGMMV resistance locus/loci is/are herein also referred to as QTLs (Quantitative Trait Locus/loci).

The term "breeding" encompasses herein crossing, backcrossing, selfing, selection, double haploid production, embryo rescue, protoplast fusion, marker assisted selection, mutation breeding, embryo rescue, etc. as known to the breeder (i.e. methods other than genetic modification/transformation/transgenic methods), by which, for example, a recombinant chromosome 1, 4, 5, 7 or 9 can be obtained, identified, produced and/or transferred. A recombinant chromosome is a recipient chromosome comprising and introgression fragment from a donor. So a "recombinant chromosome 1 or 4 or 5 or 7 or 9" herein means that the chromosome comprises an introgression fragment which comprises QTL1.1 (chromosome 1), QTL4.1 (chromosome 4), QTL5.2 (chromosome 5), QTL7.1 (chromosome 7) or QTL9.1 (chromosome 9) from a CGMMV resistant donor.

"Marker assisted selection" or "MAS" is a process of using the presence of molecular markers (such as SNP markers), which are genetically and physically linked to a particular locus or to a particular chromosome region, to select plants for the presence of the specific locus or region. For example, a molecular marker (such as the SNP markers of Table 1 and Table 6) genetically and physically linked to QTL1.1, QTL4.1, QTL5.2, QTL7.1 or QTL9.1, can be used to detect and/or select watermelon plants, or plant parts, comprising the QTL. The closer the linkage of the molecular marker to the locus, the less likely it is that the marker is dissociated from the locus through meiotic recombination. Likewise, the closer two markers are linked to each other the less likely it is that the two markers will be separated from one another (and the more likely they will co-segregate as a unit). The term "genotyping" refers to methods by which the genotype of a plant or plant cell or plant part is determined, especially for one or more nucleotides such as one or more SNP markers. The genotype of a SNP marker consist of two nucleotides in a diploid plant or plant cell, of three nucleotides in a triploid and of four nucleotides in a tetraploid plant or cell.

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one or two loci or genes (or phenotypic characteristics due to these specific loci or genes), but which can otherwise differ from one another enormously as regards the other loci or genes.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

"F1 hybrid" plant (or F1 hybrid seed) is the generation obtained from crossing two inbred parent lines. Thus, F1 hybrid seeds are seeds from which F1 hybrid plants grow. F1 hybrids are more vigorous and higher yielding, due to heterosis. Inbred lines are essentially homozygous at most loci in the genome. A "plant line" or "breeding line" refers to a plant and its progeny. As used herein, the term "inbred line" refers to a plant line which has been repeatedly selfed and is nearly homozygous. Thus, an "inbred line" or "parent line" refers to a plant which has undergone several generations (e.g. at least 5, 6, 7 or more) of inbreeding, resulting in a plant line with a high uniformity.

On the phenotypic level *Citrullus* crop plant cells or *Citrullus* crop plants into which CGMMV resistance has been introgressed, can be discriminated from corresponding *Citrullus* plant cells or corresponding *Citrullus* plants in that they show resistance to CGMMV infection, i.e. the plants comprising the introgression fragment or fragments are resistant to CGMMV, as described herein. On the genetic level *Citrullus* crop plant cells or *Citrullus* crop plants into which CGMMV resistance has been introgressed can be discriminated from corresponding *Citrullus* plant cells or corresponding *Citrullus* plants in that their genome comprises one or more CGMMV resistance conferring chromosomal fragment which originate from another plant. The term "corresponding" in connection with plant cells or plants compared to each other means that the plant cells or plants compared to each other have a similar or the same phenotypic appearance or genotype, apart from that the plant cell or plant into which CGMMV resistance has been introgressed is resistant to CGMMV and/or comprises one or more chromosomal fragments in its genome that confers resistance to CGMMV. The chromosomal fragments (introgression fragments) comprise the resistance locus, or QTL, described herein. Plants disclosed herein have e.g. a *Citrullus lanatus* ssp *vulgaris* genome but introgressed into their genome one or more chromosomal fragments from *Citrullus colocynthis*, e.g. from NCIMB 42624, whereby the introgressed chromosomal fragment or fragments confer resistance to CGMMV. The introgressed fragment(s) is/are from the donor, while the remaining genome is from the recipient.

"Chromosomal fragment" or "introgression fragment" or "introgressed fragment" means herein any fragment composed of a consecutive DNA sequence in a genome which when present or absent in the genome confers a function and/or determines the phenotype of a plant. With respect to the present invention the chromosomal fragment introgressed into a plant cell or plant according to the invention and thus being present in the genome of a plant cell or plant according to the invention confers the phenotype of CGMMV resistance (optionally the phenotype may only be expressed when the fragment is in homozygous form). Thus, in one aspect a plant lacking the chromosomal fragment(s), e.g. a cultivated watermelon plant lacking *C. colocynthis* fragments in its genome, will be CGMMV susceptible, while a plant comprising one or more of the chromosomal fragments will be CGMMV resistant.

A chromosomal fragment may be described or defined by specific molecular markers (RFLP, AFLP, RADP, SNP etc.), by the physical region of the chromosome, by genes or specific alleles thereof being present or absent, by specific sequences of cDNAs or genomic DNAs, sequences of proteins encoded by DNAs present or absent and the like. In one aspect the chromosomal fragments are herein described or defined by Single Nucleotide Polymorphism markers (SNP markers) linked to the CGMMV resistance-conferring QTL, whereby the single nucleotide of the *C. colcynthis* donor has a different nucleotide than the single nucleotide of the recipient at the SNP marker position. The chromosomal fragment which comprises the QTL can thus be defined by the physical region and/or by SNP markers and sequences comprising the SNP markers in-between which the introgressed fragment is located and/or by SNP marker nucleotides (donor SNP nucleotides) present on the introgressed fragment (and absent in the susceptible recipient lacking the introgressed fragment).

A "SNP (=Single Nucleotide Polymorphism)" in context with the present invention is to be understood as a variation in a single nucleotide that occurs at a specific position in the genome. A SNP is the variation of the single nucleotide at the given position in a genome between two plants. If a donor plant (e.g. a *C. colocynthis* plant) having a CGMMV resistance locus shows in its corresponding sequence at a specific single position a nucleotide which is different from the corresponding nucleotide at the same position of a recipient plant (e.g. cultivated watermelon susceptible to CGMMV), the position defines a SNP between the donor and the recipient. If the donor plant has one of the four possible nucleotides (A, C, T or G) at a specific position, a SNP occurs, when the recipient plant has either of the remaining three possible nucleotides at the same corresponding sequence position. In a cultivated watermelon plant comprising an introgression fragment from a donor, it can therefore easily be determined if the single nucleotide of the SNP is from the donor (donor SNP nucleotide) or from the cultivated watermelon (recipient SNP nucleotide or susceptible SNP nucleotide). The cultivated watermelon chromosomes are e.g. those found on cucurbitgenomics.org and carrying out a BLAST analysis against the 'Watermelon (Charleston Gray) Genome' using any of the sequences comprising a donor SNP (i.e. any of SEQ ID NO: 1 to SEQ ID NO: 24), will show the chromosomal location of the SNP in the cultivated watermelon genome.

Thus, in a further embodiment non-genetically engineered *Citrullus* plant cells or plants according to the invention comprising introgressed resistance to CGMMV comprise a chromosomal fragment from another plant cell or plant integrated into their genome, wherein said chromosomal fragment confers CGMMV resistance. Accordingly, the genome of plant cells according to the invention and plants according to the invention comprising introgressed resistance to CGMMV differs at a specific CGMMV resistance locus or genomic region comprising the CGMMV resistance locus from corresponding non-CGMMV resistant plant cells or corresponding non-CGMMV resistant plants.

Whether a CGMMV resistant plant cell or plant differs at a specific CGMMV resistance locus or region comprising the locus from corresponding non-CGMMV resistant plant cells or plants, can be determined by the skilled person using one or more techniques known in the art, such as phenotypic assays, whole genome sequencing, molecular marker analysis, trait mapping, chromosome painting, allelism tests and the like, or combinations of techniques. Likewise the SNP markers linked to the QTLs described in Table 1 and Table 6 can be used, as will be described.

*Citrullus* plants being resistant to CGMMV can be produced by various methods commonly known to a person skilled in the art. Possible e.g. is the use of seeds deposited under accession number NCIMB 42624 or resistant progeny thereof. A particular advantage of these deposited seeds is that the plants grown from the seeds are resistant to CGMMV and that the plants are homozygous for the QTLs and SNP markers. Thus, the chromosomal fragment conferring resistance to CGMMV can be introduced or introgressed into other *Citrullus* plants by using e.g. the pollen of CGMMV resistant *Citrullus* plants for fertilizing other *Citrullus* plants, like other *Citrullus* crop plants, in particular *Citrullus lanatus* plants, especially *Citrullus lanatus* subspecies *vulgaris* (cultivated watermelon) plants. The CGMMV resistance conferring chromosomal fragment on chromosome 7 (QTL7.1) and chromosome 9 (QTL9.1) are dominant, at least in plants having a diploid degree of ploidy. Therefore, after crossing a CGMMV resistant *Citrullus* plant e.g. a plant grown from seeds deposited under accession number NCIMB 42624 (or a resistant progeny thereof) with another *Citrullus* plant, CGMMV resistance is obtained already in the F1 generation. Plants can then be backcrossed to the susceptible parent (recipient) in order to reduce the donor genome, while retaining the CGMMV resistant introgression fragments of the donor genome. Other CGMMV resistant *Citrullus colocynthis* accessions may also be identified by testing the CGMVV resistance of such accessions, preferably in comparison to plants grown from seeds deposited under accession number NCIMB 42624 (or resistant progeny thereof) and a susceptible control, e.g. variety Sugar Baby. For example mechanical leaf inoculation and/or SNP marker analysis (genotyping) and/or RT-qPCR as described in the Examples can be used to identify *Citrullus colocynthis* accessions which have the same level of resistance and/or the same or very similar level of virus RNA as the plants grown from seeds deposited under accession number NCIMB 42624 (or resistant progeny thereof). Also, CGMMV resistant *Citrullus colocynthis* accessions may also be identified by analyzing the SNP marker genotype for one or more of the SNP markers of Table 1 and Table 6. A *Citrullus colocynthis* accessions comprising the same nucleotide as the *C. colocynthis* donor NCIMB 42624 (i.e. the donor nucleotide) for one or more or all of SNP13, SNP14, SNP15, SNP16, SNP17 and/or SNP18 will therefore most likely comprise QTL7.1 in its genome. Likewise a *Citrullus colocynthis* accessions comprising the same nucleotide as the *C. colocynthis* donor NCIMB 42624 for one or more or all of SNP19, SNP20, SNP21, SNP22, SNP23 and/or SNP24 will therefore most likely comprise QTL9.1 in its genome. The same holds for QTL1.1, QTL4.1 and QTL5.2 and the respective SNP markers linked to these QTLs (see e.g. Table 1 and 6).

In one aspect the *Citrullus* plant cells or *Citrullus* plants according to the invention comprise *Citrullus* plants having any degree of ploidy, including plants with even numbered degree of ploidy (2n, 4n, 6n, 8n etc.) and plants with uneven numbered degree of ploidy (3n, 5n etc.). As resistance conferred by QTL7.1 and QTL9.1 is dominant, plant cells and plants are CGMMV resistant even when the introgression fragment is in heterozygous state in the even numbered polyploids (one copy in 2n, two copies in 4n, four copies in 8n, etc.).

Polyploidisation is widespread in plants. It is responsible for increasing genetic diversity and producing species showing increase in robustness, size, vigour and disease resistance. Obvious advantages for polyploid plants are heterosis and gene redundancy.

A number of today cultivated broad acre and plantation crops have undergone one or more genome duplications. Examples are cotton, potato, bread wheat, oil seeds, corn, soybean, sunflower, banana, apple and coffee (Renny-Byfield 7 Wendel, 2014, American J. Botany, 101(10), 1711-1725).

In particular in vegetable breeding, polyploidy in various plants was induced by the use of chemicals including colchicine, colchamine, oryzalin, colcemid, trifluralin or amiprophosmethyl. Examples for genome duplications in vegetables produced by the use of chemicals are diploid brussels sprouts from haploid plants, tetraploid peas, tetraploid watermelons, tetraploid muskmelons, tetraploid onions, octaploid cocoyams, tetraploid snake gourds, triploid and tetraploid fluted pumpkins, tetraploid cucumbers and tetraploid french beans (Kazi, 2015, J. Global Biosciences 4(3), 1774-1779). The invention concerns in one aspect non-genetically engineered *Citrullus* plant cells or plants according to the invention having any degree of ploidy, wherein the degree of ploidy can be even or uneven numbered, preferably the degree of ploidy is 2n, 3n or 4n.

With respect to an uneven numbered degree of ploidy a preferred embodiment of the invention concerns non-genetically engineered *Citrullus* plant cells or plants according to the invention which are triploid (3n). In one aspect the plant cells or plants are of the species *C. lanatus* ssp *vulgaris* and are triploid and comprise the introgression fragment on at least one of the three homologous chromosomes, or on two of the three chromosomes, or preferably on all three of the three homologous chromosomes (i.e. the plant cell or plant is homozygous for the introgression fragment conferring CGMMV resistance). Such a triploid plant, or seed from which such a triploid plant can be grown, can easily be generated by crossing a diploid watermelon comprising e.g. the introgression fragment in homozygous form with a tetraploid watermelon comprising e.g. the introgression fragment in homozygous form (in four copies, for example produced by chromosome doubling of the homozygous diploid). The seeds produced are triploid seeds, from which a triploid watermelon plant can be grown. Such triploid seeds and triploid plants are resistant against CGMMV and are one aspect of the invention.

In one aspect the triploid plants are cultivated watermelon plants, plant parts or cells comprising QTL7.1 and/or QTL9.1, preferably in homozygous form (i.e. three copies). Optionally the cultivated watermelon plants, plant parts or cells further comprise a QTL selected from QTL1.1, QTL4.1 and QTL5.2 in homozygous form (three copies). Thus, the introgression fragment of each QTL is present in three copies (comprising three recombinant chromosomes, e.g. three recombinant chromosome 7 and/or 9) in a triploid plant cell or plant and the one or more SNP markers linked to the QTL are present in three copies and comprise the donor nucleotide in three copies.

In one aspect the triploid plants are cultivated watermelon plants comprising one or more or all QTLs selected from QTL1.1, QTL4.1, QTL5.2, QTL7.1 and QTL9.1 in homozygous form (i.e. three copies). The donor nucleotides of one or more of the SNP markers linked to each QTL are preferably then present in three copies in a triploid plant or plant cell.

With respect to an even numbered degree of ploidy a preferred embodiment of the invention concerns non-genetically engineered *Citrullus* plant cells or plants according to the invention which are diploid (2n) or tetraploid (4n). In one aspect the plant cells or plants are of the species *C. lanatus* ssp *vulgaris* and are diploid and comprise the introgression fragment(s) in heterozygous or homozygous form; in another aspect the plant cells or plants are of the species *C. lanatus* ssp *vulgaris* and are tetraploid and comprise the introgression fragment(s) in heterozygous (two copies) or homozygous (four copies) form. Such diploid and tetraploid seeds and diploid and tetraploid plants are resistant against CGMMV and are one aspect of the invention. They can be used as parents for producing triploid CGMMV resistant seeds and plants.

Thus, in one aspect the diploid plants are cultivated watermelon plants comprising QTL7.1 and/or QTL9.1 in homozygous form or in heterozygous form. Optionally the cultivated watermelon plants, plant parts or cells further comprise a QTL selected from QTL1.1, QTL4.1 and QTL5.2 in homozygous form (two copies). Thus, when the QTL is in homozygous form, e.g. in an inbred line, the introgression fragment of each QTL is present in two copies (comprising two recombinant chromosomes, e.g. two recombinant chromosome 7 and/or 9) in a diploid plant cell or plant and the one or more SNP markers linked to the QTL are present in two copies and comprise the donor nucleotide in two copies.

In another aspect the diploid plants are cultivated watermelon plants comprising one or more or all of the QTLs selected from QTL1.1, QTL4.1, QTL5.2, QTL7.1 and QTL9.1 in homozygous form or in heterozygous form.

In one further aspect the tetraploid plants are cultivated watermelon plants comprising QTL7.1 and/or QTL9.1 in homozygous form (four copies of QTL7.1 and/or QTL9.1) or in heterozygous form (two copies of QTL7.1 and/or QTL9.1). Optionally the cultivated watermelon plants, plant parts or cells further comprise a QTL selected from QTL1.1, QTL4.1 and QTL5.2 in heterozygous or in homozygous form (two copies or four copies respectively).

In another aspect the tetraploid plants are cultivated watermelon plants comprising one or more or all of the QTLs selected from QTL1.1, QTL4.1, QTL5.2, QTL7.1 and QTL9.1 in homozygous form or in heterozygous form.

"Even numbered degree of ploidy" in context of the present invention means that the number of homologous chromosome sets present in a cell or organism when divided by two results in an integer. The cells or organisms thus are diploid (2n), tetraploid (4n), hexaploid (6n), octaploid (8n) etc. "Uneven numbered degree of ploidy" in context of the present invention means that the number of homologous chromosome sets present in a cell or organism when divided by two does not result an integer. The cells or organisms thus are haploid (1n), triploid (3n) etc.

"Diploid plant cell or plant" in context of the present invention means a plant, vegetative plant part, fruit, seed or plant cell, having two sets of corresponding chromosomes, designated herein as 2n.

"Tetraploid plant cell or plant" in context of the present invention means a plant, vegetative plant part(s), fruit, seed or plant cell, having four sets of corresponding chromosomes, designated herein as 4n.

"Triploid plant cell or plant" in context of the present invention means a plant, vegetative plant part(s), fruit, seed or plant cell, having three sets of corresponding chromosomes, designated herein as 3n.

It is commonly understood in the art that sexually reproducing cells of plants (pollen and ovule) comprise a set of chromosomes which is half of the set of the remaining cells of said plant. Plant pollen and ovules can be regenerated into whole plants. In case of plants having an even numbered degree of ploidy it is therefore generally possible to reduce the degree of ploidy by half upon regeneration of pollen or ovules. From plants according to the invention having an even numbered degree of ploidy (e.g. 2n, 4n, 6n, 8n etc.) plants having a bisected set of chromosomes (e.g. 1n, 2n, 3n, 4n, etc., respectively) can be produced by means of pollen or ovule regeneration.

Diploid (2n) plants according to the invention can e.g. be regenerated from pollen or ovule cells comprising CGMMV resistance, the pollen or ovule cells being obtained from a tetraploid plant comprising CGMMV resistance. Preferably, the pollen or ovule cells being obtained from a tetraploid plant comprising CGMMV resistance in homozygous state. The derived diploid plants may then be used in further breeding and in generating plants having CGMMV resistance.

In one aspect of the invention the plants are cultivated watermelon, which are diploid (2n), tetraploid (4n) or triploid (3n) and comprise at least one chromosome of the homologous chromosomes comprising a CGMMV resistance conferring introgression fragment as described. In one aspect at least two, three or even all four of the homologous chromosomes comprise the introgression fragment.

Triploid (3n) plants, especially triploid cultivated watermelon plants, can be produced by crossing a diploid (2n) plant with a tetraploid (4n) plant. The hybrid plant seeds originating from said cross will be triploid (3n).

At least one of the diploid (2n) and tetraploid (4n) plants crossed with each other is resistant to CGMMV. Preferably the diploid (2n) and tetraploid (4n) plants according to the invention crossed with each other both are resistant to CGMMV. In one aspect both the diploid and the tetraploid plant, especially cultivated watermelon plants, are homozygous for the introgression fragment (i.e. the diploid comprises two copies and the tetraploid four copies of the introgression fragment) and the resulting triploid comprises three copies of the introgression fragment.

Plants with an uneven numbered degree of ploidy, e.g. triploid (3n) plants are commonly male and female sterile, because during meiosis the chromosomes cannot be equally divided to the daughter cells. Thus, seeds having an uneven numbered degree of ploidy, e.g. triploid plants can be cultivated for producing seedless fruits.

In one aspect, the diploid plant is a cultivated watermelon plant comprising an introgression fragment from a CGMMV resistant *C. colocynthis* donor, e.g. from NCIMB 42624 or from CGMMV resistant progeny thereof, which fragment confers CGMMV resistance onto the cultivated watermelon plant. As there are five QTLs in NCIMB 42624, the diploid plant is in one aspect a cultivated watermelon plant comprising one or more or all of the QTLs selected from QTL1.1, QTL4.1, QTL5.2, QTL7.1 and QTL9.1.

As mentioned, such a cultivated watermelon plant can be produced by backcrossing (one or more backcrosses) of the CGMMV resistance locus from the donor (e.g. NCIMB 42624 or CGMMV resistant progeny thereof) into an elite line or variety of cultivated watermelon. By selfing the backcrossed plant one or more times, the introgression fragment(s) will become homozygous and the plant will comprise the CGMMV resistance locus as found in, or as obtainable from the donor, e.g. NCIMB 42624.

Doubling the chromosomes of such a diploid will result in a tetraploid which is homozygous for the introgression fragment(s) and the plant will comprise the CGMMV resistance locus as found in, or as obtainable from the donor, e.g. NCIMB 42624. Subsequent crossing of a homozygous diploid with a homozygous tetraploid enables the production of a triploid comprising three copies of the CGMMV resistance locus as found in, or as obtainable from the donor, e.g. NCIMB 42624.

In this way, diploid watermelon plants comprising only one of the five QTLs can be made, but also plants comprising different combinations of the QTLs can be made. Likewise tetraploids and triploids comprising only one of the QTLs or different combinations of the QTLs can be made.

Cultivated watermelon plants comprising at least one of the dominant QTLs, QTL7.1 and/or QTL9.1 are a particular embodiment herein. Optionally these plants can comprise one or more of the recessive QTLs, QTL1.1, QTL4.1 and/or QTL5.2 in their genome, preferably in homozygous form.

The SNPs provided herein can be used for various purposes. They can be used to define the QTL containing region, or detect (e.g. in donor material or in cultivated material in e.g. diagnostic assays) the introgression fragment(s) comprising the QTL(s), or they can be used for marker assisted breeding methods for transferring the QTL(s) from a donor to a recipient plant or from one breeding line or variety into another.

The SNP markers linked to the QTLs are indicated in Table 1 above, as are there position in the watermelon genome, i.e. on the respective chromosome of cultivated watermelon. Also the SNP genotype of the resistant donor is indicated, whereby the donor is homozygous for the SNP and for the Sequence (e.g. the donor SNP or donor sequence for SNP1 is a 'Cytosine' ('C') at nucleotide 51 of SEQ ID NO: 1. The genotype of the diploid donor is therefore 'CC' ('Cytosine/Cytosine'), comprising two copies of SEQ ID NO: 1 and two copies of the donor nucleotide of SNP1.

As there may be variants of the QTLs in other *C. colocynthis* donors, the donor SNP may be present in slightly varying nucleotide sequences, for example one, two or three nucleotides of SEQ ID NO: 1 may be different from those of SEQ ID NO: 1 while still having the *C. colocynthis* donor SNP nucleotide (for SNP1 this is a Cytosine) at the equivalent position when doing a pairwise alignment of the sequences.

Thus, "SNP1" or "SNP1 marker" refers herein to nucleotide 51 of SEQ ID NO: 1, or of a sequence comprising at least 95% sequence identity with SEQ ID NO: 1. When referring to the *C. colocynthis* donor nucleotide for SNP1 herein, i.e. a Cytosine ('C') at nucleotide 51 of SEQ ID NO: 1 or of a sequence comprising at least 95% sequence identity to SEQ ID NO: 1, one can equally refer to SEQ ID NO: 1 itself (without mentioning the nucleotide at position 51 of SEQ ID NO: 1), or a sequence comprising at least 95% sequence identity to SEQ ID NO: 1 and comprising a Cytosine at nucleotide 51, because SEQ ID NO: 1 comprises the donor nucleotide (i.e. a Cytosine) at nucleotide 51. Thus plants or plant cells comprising an introgression fragment which is from the CGMMV resistant *C. colocynthis* donor, may comprise the donor nucleotide for SNP1 (i.e. a Cytosine at nucleotide 51) or "comprise SEQ ID NO: 1" or "a sequence comprising at least 95% sequence identity to SEQ ID NO: 1 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP1 in homozygous form, a diploid cell comprises two copies of SEQ ID NO: 1 (or of a sequence comprising at least 95% sequence identity to SEQ ID NO: 1), i.e. the "CC" genotype. A triploid plant or cell will comprise three copies and a tetraploid plant or cell four copies. Likewise, when the introgression fragment comprising the donor nucleotide for SNP1 in heterozygous form (only one chromosome of a pair of homologous chromosomes has the introgression), a diploid cell comprises one copy of SEQ ID NO: 1 (or of a sequence comprising at least 95% sequence identity to SEQ ID NO: 1). The other chromosome, lacking the introgression fragment comprises any of the other nucleotides, i.e. an Adenine, Guanine or Thymine at nucleotide 51 of SEQ ID NO: 1 (SNP1), i.e. the sequence of the susceptible recurrent parent. This depends on which recurrent parent was used. In one aspect this is a Thymine for SNP1, as indicated in Table 1, as this was the recurrent parent used in the backcrossing herein.

"Sequence identity" and "sequence similarity" can be determined by alignment of two peptide or two nucleotide sequences using global or local alignment algorithms. Sequences may then be referred to as "substantially identical" when they are optimally aligned by for example the programs GAP or BESTFIT or the Emboss program "Needle" (using default parameters, see below) share at least a certain minimal percentage of sequence identity defined further below). These programs use the Needleman and Wunsch global alignment algorithm to align two sequences over their entire length, maximizing the number of matches and minimizing the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1 992, PNAS 89, 1 09 1 5-1 09 1 9). Sequence alignments and scores for percentage sequence identity may for example be determined using computer programs, such as EMBOSS as available on the world wide web under ebi.ac.uk/Tools/psa/emboss_needle/). Alternatively sequence similarity or identity may be determined by searching against databases such as FASTA, BLAST, etc., but hits are preferably retrieved and aligned pairwise to compare sequence identity. Two proteins or two protein domains, or two nucleic acid sequences have "substantial sequence identity" if the percentage sequence identity is at least 95%, 98% or 99% (as determined by Emboss "needle" using default parameters, i.e. gap creation penalty=10, gap extension penalty=0.5, using scoring matrix DNAFULL for nucleic acids an Blosum62 for proteins). When reference is made to a nucleic acid sequence (e.g. DNA or genomic DNA) having "substantial sequence identity to" a reference sequence or having a sequence identity of at least 80%, e.g. at least 95%, 98% or 99% nucleic acid sequence identity to a reference sequence, in one embodiment said nucleotide sequence is considered substantially identical to the given nucleotide sequence and can be identified using stringent hybridization conditions.

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

Thus, "SNP2" or "SNP2 marker" refers herein to nucleotide 51 of SEQ ID NO: 2, or of a sequence comprising at least 95% sequence identity with SEQ ID NO: 2. When referring to the *C. colocynthis* donor nucleotide for SNP2 herein, i.e. a Guanine ('G') at nucleotide 51 of SEQ ID NO: 2 or of a sequence comprising at least 95% sequence identity to SEQ ID NO: 2, one can equally refer to SEQ ID NO: 2 itself (without mentioning the nucleotide at position 51 of SEQ ID NO: 2), or a sequence comprising at least 95% sequence identity to SEQ ID NO: 2 and comprising a Guanine at nucleotide 51, because SEQ ID NO: 2 comprises the donor nucleotide (i.e. a Guanine) at nucleotide 51. Thus plants or plant cells comprising an introgression fragment which is from the CGMMV resistant *C. colocynthis* donor, may comprise the donor nucleotide for SNP2 (i.e. a Guanine at nucleotide 51) or "comprise SEQ ID NO: 2" or "a sequence comprising at least 95% sequence identity to SEQ ID NO: 2 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle'. When the introgression fragment comprising the donor nucleotide for SNP2 in homozygous form, a diploid cell comprises two copies of SEQ ID NO: 2 (or of a sequence comprising at least 95% sequence identity to SEQ ID NO: 2), i.e. the "GG" genotype. A triploid plant or cell will comprise three copies and a tetraploid plant or cell four copies. Likewise, when the introgression fragment comprising the donor nucleotide for SNP2 in heterozygous form (only one chromosome of a pair of homologous chromosomes has the introgression), a diploid cell comprises one copy of SEQ ID NO: 2 (or of a sequence comprising at least 95% sequence identity to SEQ ID NO: 2). The other chromosome, lacking the introgression fragment comprises any of the other nucleotides, i.e. an Adenine, Cytosine or Thymine at nucleotide 51 of SEQ ID NO: 2 (SNP2), i.e. the sequence of the susceptible recurrent parent. This depends on which recurrent parent was used. In one aspect this is a Adenine for SNP2, as indicated in Table 1, as this was the recurrent parent used in the backcrossing herein.

Thus, "SNP3" or "SNP3 marker" refers herein to nucleotide 51 of SEQ ID NO: 3, or of a sequence comprising at least 95% sequence identity with SEQ ID NO: 3. When referring to the *C. colocynthis* donor nucleotide for SNP3 herein, i.e. a Cytosine ('C') at nucleotide 51 of SEQ ID NO: 3 of a sequence comprising at least 95% sequence identity to SEQ ID NO: 3, one can equally refer to SEQ ID NO: 3 itself (without mentioning the nucleotide at position 51 of SEQ ID NO: 3), or a sequence comprising at least 95% sequence identity to SEQ ID NO: 3 and comprising a Cytosine at nucleotide 51, because SEQ ID NO: 3 comprises the donor nucleotide (i.e. a Cytosine) at nucleotide 51. Thus plants or plant cells comprising an introgression fragment which is from the CGMMV resistant *C. colocynthis* donor, may comprise the donor nucleotide for SNP3 (i.e. a Cytosine at nucleotide 51) or "comprise SEQ ID NO: 3" or "a sequence comprising at least 95% sequence identity to SEQ ID NO: 3 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP3 in homozygous form, a diploid cell comprises two copies of SEQ ID NO: 3 (or of a sequence comprising at least 95% sequence identity to SEQ ID NO: 3), i.e. the "CC" genotype. A triploid plant or cell will comprise three copies and a tetraploid plant or cell four copies. Likewise, when the introgression fragment comprising the donor nucleotide for SNP3 in heterozygous form (only one chromosome of a pair of homologous chromosomes has the introgression), a diploid cell comprises one copy of SEQ ID NO: 3 (or of a sequence comprising at least 95% sequence identity to SEQ ID NO: 3). The other chromosome, lacking the introgression fragment comprises any of the other nucleotides, i.e. an Adenine, Guanine or Thymine at nucleotide 51 of SEQ ID NO: 3 (SNP3), i.e. the sequence of the susceptible recurrent parent. This depends on which recurrent parent was used. In one aspect this is a Thymine for SNP3, as indicated in Table 1, as this was the recurrent parent used in the backcrossing herein.

Thus "SNP4" or "SNP4 marker" refers herein to nucleotide 51 of SEQ ID NO: 4, or of a sequence comprising at least 95% sequence identity with SEQ ID NO: 4. When referring to the *C. colocynthis* donor nucleotide for SNP4 herein, i.e. a Cytosine ('C') at nucleotide 51 of SEQ ID NO: 4 of a sequence comprising at least 95% sequence identity to SEQ ID NO: 4, one can equally refer to SEQ ID NO: 4 itself (without mentioning the nucleotide at position 51 of SEQ ID NO: 4), or a sequence comprising at least 95% sequence identity to SEQ ID NO: 4 and comprising a Cytosine at nucleotide 51, because SEQ ID NO: 4 comprises the donor nucleotide (i.e. a Cytosine) at nucleotide 51. Thus plants or plant cells comprising an introgression fragment which is from the CGMMV resistant *C. colocynthis* donor, may comprise the donor nucleotide for SNP4 (i.e. a Cytosine at nucleotide 51) or "comprise SEQ ID NO: 4" or "a sequence comprising at least 95% sequence identity to SEQ ID NO: 4 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP4 in homozygous form, a diploid cell comprises two copies of SEQ ID NO: 4 (or of a sequence comprising at least 95% sequence identity to SEQ ID NO: 4), i.e. the "CC" genotype. A triploid plant or cell will comprise three copies and a tetraploid plant or cell four copies. Likewise, when the introgression fragment comprising the donor nucleotide for SNP4 in heterozygous form (only one chromosome of a pair of homologous chromosomes has the introgression), a diploid cell comprises one copy of SEQ ID NO: 4 (or of a sequence comprising at least 95% sequence identity to SEQ ID NO: 4). The other chromosome, lacking the introgression fragment comprises any of the other nucleotides, i.e. an Adenine, Guanine or Thymine at nucleotide 51 of SEQ ID NO: 4 (SNP4), i.e. the sequence of the susceptible recurrent parent. This depends on which recurrent parent was used. In one aspect this is a Thymine for SNP4, as indicated in Table 1, as this was the recurrent parent used in the backcrossing herein.

Thus, "SNP5" or "SNP5 marker" refers herein to nucleotide 51 of SEQ ID NO: 5, or of a sequence comprising at least 95% sequence identity with SEQ ID NO: 5. When referring to the *C. colocynthis* donor nucleotide for SNP5 herein, i.e. a Guanine ('G') at nucleotide 51 of SEQ ID NO: 5 or of a sequence comprising at least 95% sequence identity to SEQ ID NO: 5, one can equally refer to SEQ ID NO: 5 itself (without mentioning the nucleotide at position 51 of SEQ ID NO: 5), or a sequence comprising at least 95% sequence identity to SEQ ID NO: 5 and comprising a Guanine at nucleotide 51, because SEQ ID NO: 5 comprises the donor nucleotide (i.e. a Guanine) at nucleotide 51. Thus plants or plant cells comprising an introgression fragment which is from the CGMMV resistant *C. colocynthis* donor, may comprise the donor nucleotide for SNP5 (i.e. a Guanine at nucleotide 51) or "comprise SEQ ID NO: 5" or "a sequence comprising at least 95% sequence identity to SEQ ID NO: 5 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP5 in homozygous form, a diploid cell comprises two copies of SEQ ID NO: 5 (or of a sequence comprising at least 95% sequence identity to SEQ ID NO: 5), i.e. the "GG" genotype. A triploid plant or cell will comprise three copies and a tetraploid plant or cell four copies. Likewise, when the introgression fragment comprising the donor nucleotide for SNP5 in heterozygous form (only one chromosome of a pair of homologous chromosomes has the introgression), a diploid cell comprises one copy of SEQ ID NO: 5 (or of a sequence comprising at least 95% sequence identity to SEQ ID NO: 5). The other chromosome, lacking the introgression fragment comprises any of the other nucleotides, i.e. an Adenine, Cytosine or Thymine at nucleotide 51 of SEQ ID NO: 5 (SNP5), i.e. the sequence of the susceptible recurrent parent. This depends on which recurrent parent was used. In one aspect this is a Adenine for SNP5, as indicated in Table 1, as this was the recurrent parent used in the backcrossing herein.

Thus, "SNP6" or "SNP6 marker" refers herein to nucleotide 51 of SEQ ID NO: 6, or of a sequence comprising at least 95% sequence identity with SEQ ID NO: 6. When referring to the *C. colocynthis* donor nucleotide for SNP6 herein, i.e. a Thymine ('T') at nucleotide 51 of SEQ ID NO: 6 or of a sequence comprising at least 95% sequence identity to SEQ ID NO: 6, one can equally refer to SEQ ID NO: 6 itself (without mentioning the nucleotide at position 51 of SEQ ID NO: 6), or a sequence comprising at least 95% sequence identity to SEQ ID NO: 6 and comprising a Thymine at nucleotide 51, because SEQ ID NO: 6 comprises the donor nucleotide (i.e. a Thymine) at nucleotide 51. Thus plants or plant cells comprising an introgression fragment which is from the CGMMV resistant *C. colocynthis* donor, may comprise the donor nucleotide for SNP6 (i.e. a Thymine at nucleotide 51) or "comprise SEQ ID NO: 6" or "a sequence comprising at least 95% sequence identity to SEQ ID NO: 6 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP6 in homozygous form, a diploid cell comprises two copies of SEQ ID NO: 6 (or of a sequence comprising at least 95% sequence identity to SEQ ID NO: 6), i.e. the "TT" genotype. A triploid plant or cell will comprise three copies and a tetraploid plant or cell four copies. Likewise, when the introgression fragment comprising the donor nucleotide for SNP6 in heterozygous form (only one chromosome of a pair of homologous chromosomes has the introgression), a diploid cell comprises one copy of SEQ ID NO: 6 (or of a sequence comprising at least 95% sequence identity to SEQ ID NO: 6). The other chromosome, lacking the introgression fragment comprises any of the other nucleotides, i.e. an Adenine, Cytosine or Guanine at nucleotide 51 of SEQ ID NO: 6 (SNP6), i.e. the sequence of the susceptible recurrent parent. This depends on which recurrent parent was used. In one aspect this is a Cytosine for SNP6, as indicated in Table 1, as this was the recurrent parent used in the backcrossing herein.

SEQ ID NO: 1 (comprising SNP1), SEQ ID NO: 2 (comprising SNP2), SEQ ID NO: 3 (comprising SNP3), SEQ ID NO: 4 (comprising SNP4), SEQ ID NO: 5 (comprising SNP5) and SEQ ID NO: 6 (comprising SNP6) are physically linked to the CGMMV resistance QTL1.1 on chromosome 1 of the donor. Marker SNP5 is most closely linked. An introgression fragment comprising CGMMV resistance from C. colocynthis therefore comprises the resistant donor nucleotide (and the sequence comprising the donor nucleotide or a sequence comprising at least 95% sequence identity thereto and comprising the donor nucleotide) for one or more or all of the SNP markers of the group of SNP1, SNP2, SNP3, SNP4, SNP5 and SNP6, more preferably it comprises the resistant donor nucleotide for one or more or all of the SNP markers selected from the group of SNP4, SNP5 and SNP6, more preferably it comprises the donor nucleotide for SNP4 and/or SNP5 or for SNP5 and/or SNP6, even more preferably it comprises at least the resistant donor nucleotide for SNP5 (and thus SEQ ID NO: 5 or a sequence comprising at least 95% sequence identity to SEQ ID NO: 5 and comprising the donor nucleotide at nucleotide 51). Cultivated watermelon plants, plant cells and plant parts comprising such an introgression fragment, preferably in homozygous form, are an aspect of the invention.

Thus, "SNP7" or "SNP7 marker" refers herein to nucleotide 51 of SEQ ID NO: 7, or of a sequence comprising at least 95% sequence identity with SEQ ID NO: 7. When referring to the C. colocynthis donor nucleotide for SNP7 herein, i.e. a Thymine ('T') at nucleotide 51 of SEQ ID NO: 7 or of a sequence comprising at least 95% sequence identity to SEQ ID NO: 7, one can equally refer to SEQ ID NO: 7 itself (without mentioning the nucleotide at position 51 of SEQ ID NO: 7), or a sequence comprising at least 95% sequence identity to SEQ ID NO: 7 and comprising a Thymine at nucleotide 51, because SEQ ID NO: 7 comprises the donor nucleotide (i.e. a Thymine) at nucleotide 51. Thus plants or plant cells comprising an introgression fragment which is from the CGMMV resistant C. colocynthis donor, may comprise the donor nucleotide for SNP7 (i.e. a Thymine at nucleotide 51) or "comprise SEQ ID NO: 7" or "a sequence comprising at least 95% sequence identity to SEQ ID NO: 7 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP7 in homozygous form, a diploid cell comprises two copies of SEQ ID NO: 7 (or of a sequence comprising at least 95% sequence identity to SEQ ID NO: 7), i.e. the "TT" genotype. A triploid plant or cell will comprise three copies and a tetraploid plant or cell four copies. Likewise, when the introgression fragment comprising the donor nucleotide for SNP7 in heterozygous form (only one chromosome of a pair of homologous chromosomes has the introgression), a diploid cell comprises one copy of SEQ ID NO: 7 (or of a sequence comprising at least 95% sequence identity to SEQ ID NO: 7). The other chromosome, lacking the introgression fragment comprises any of the other nucleotides, i.e. an Adenine, Cytosine or Guanine at nucleotide 51 of SEQ ID NO: 7 (SNP7), i.e. the sequence of the susceptible recurrent parent. This depends on which recurrent parent was used. In one aspect this is a Adenine for SNP7, as indicated in Table 1, as this was the recurrent parent used in the backcrossing herein.

Thus "SNP8" or "SNP8 marker" refers herein to nucleotide 51 of SEQ ID NO: 8, or of a sequence comprising at least 95% sequence identity with SEQ ID NO: 8. When referring to the C. colocynthis donor nucleotide for SNP8 herein, i.e. a Cytosine ('C') at nucleotide 51 of SEQ ID NO: 8 of a sequence comprising at least 95% sequence identity to SEQ ID NO: 8, one can equally refer to SEQ ID NO: 8 itself (without mentioning the nucleotide at position 51 of SEQ ID NO: 8), or a sequence comprising at least 95% sequence identity to SEQ ID NO: 8 and comprising a Cytosine at nucleotide 51, because SEQ ID NO: 8 comprises the donor nucleotide (i.e. a Cytosine) at nucleotide 51. Thus plants or plant cells comprising an introgression fragment which is from the CGMMV resistant C. colocynthis donor, comprise the donor nucleotide for SNP8 (i.e. a Cytosine at nucleotide 51) or "comprise SEQ ID NO: 8" or "a sequence comprising at least 95% sequence identity to SEQ ID NO: 8 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP8 in homozygous form, a diploid cell comprises two copies of SEQ ID NO: 8 (or of a sequence comprising at least 95% sequence identity to SEQ ID NO: 8), i.e. the "CC" genotype. A triploid plant or cell will comprise three copies and a tetraploid plant or cell four copies. Likewise, when the introgression fragment comprising the donor nucleotide for SNP8 in heterozygous form (only one chromosome of a pair of homologous chromosomes has the introgression), a diploid cell comprises one copy of SEQ ID NO: 8 (or of a sequence comprising at least 95% sequence identity to SEQ ID NO: 8). The other chromosome, lacking the introgression fragment comprises any of the other nucleotides, i.e. an Adenine, Guanine or Thymine at nucleotide 51 of SEQ ID NO: 8 (SNP8), i.e. the sequence of the susceptible recurrent parent. This depends on which recurrent parent was used. In one aspect this is a Adenine for SNP8, as indicated in Table 1, as this was the recurrent parent used in the backcrossing herein.

Thus "SNP9" or "SNP9 marker" refers herein to nucleotide 51 of SEQ ID NO: 9, or of a sequence comprising at least 95% sequence identity with SEQ ID NO: 9. When referring to the C. colocynthis donor nucleotide for SNP9 herein, i.e. an Adenine ('A') at nucleotide 51 of SEQ ID NO:

9 of a sequence comprising at least 95% sequence identity to SEQ ID NO: 9, one can equally refer to SEQ ID NO: 9 itself (without mentioning the nucleotide at position 51 of SEQ ID NO: 9), or a sequence comprising at least 95% sequence identity to SEQ ID NO: 9 and comprising an Adenine at nucleotide 51, because SEQ ID NO: 9 comprises the donor nucleotide (i.e. an Adenine) at nucleotide 51. Thus plants or plant cells comprising an introgression fragment which is from the CGMMV resistant *C. colocynthis* donor, may comprise the donor nucleotide for SNP9 (i.e. an Adenine at nucleotide 51) or "comprise SEQ ID NO: 9" or "a sequence comprising at least 95% sequence identity to SEQ ID NO: 9 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP9 in homozygous form, a diploid cell comprises two copies of SEQ ID NO: 9 (or of a sequence comprising at least 95% sequence identity to SEQ ID NO: 9), i.e. the "AA" genotype. A triploid plant or cell will comprise three copies and a tetraploid plant or cell four copies. Likewise, when the introgression fragment comprising the donor nucleotide for SNP9 in heterozygous form (only one chromosome of a pair of homologous chromosomes has the introgression), a diploid cell comprises one copy of SEQ ID NO: 9 (or of a sequence comprising at least 95% sequence identity to SEQ ID NO: 9). The other chromosome, lacking the introgression fragment comprises any of the other nucleotides, i.e. an Cytosine, Guanine or Thymine at nucleotide 51 of SEQ ID NO: 9 (SNP9), i.e. the sequence of the susceptible recurrent parent. This depends on which recurrent parent was used. In one aspect this is a Guanine for SNP9, as indicated in Table 1, as this was the recurrent parent used in the backcrossing herein.

SEQ ID NO: 7 (comprising SNP7), SEQ ID NO: 8 (comprising SNP8) and SEQ ID NO: 9 (comprising SNP9) are physically linked to the CGMMV resistance QTL4.1 on chromosome 4 of the donor. Marker SNP8 is most closely linked. An introgression fragment comprising CGMMV resistance from *C. colocynthis* therefore comprises in one aspect the resistant donor nucleotide (and the sequence comprising the donor nucleotide or a sequence comprising at least 95% sequence identity thereto and comprising the donor nucleotide) for one or more or all of the SNP markers of the group SNP7, SNP8 and SNP9, most preferably it comprises the resistant donor nucleotide for SNP markers SNP7 and/or SNP8 or for SNP8 and/or SNP9, even most preferably it comprises at least the resistant donor nucleotide for SNP8 (and thus SEQ ID NO: 8 or a sequence comprising at least 95% sequence identity to SEQ ID NO: 8 and comprising the donor nucleotide at nucleotide 51). Cultivated watermelon plants, plant cells and plant parts comprising such an introgression fragment, preferably in homozygous form, are an aspect of the invention.

Thus, "SNP10" or "SNP10 marker" refers herein to nucleotide 51 of SEQ ID NO: 10, or of a sequence comprising at least 95% sequence identity with SEQ ID NO: 10. When referring to the *C. colocynthis* donor nucleotide for SNP10 herein, i.e. a Thymine ('T') at nucleotide 51 of SEQ ID NO: 10 or of a sequence comprising at least 95% sequence identity to SEQ ID NO: 10, one can equally refer to SEQ ID NO: 10 itself (without mentioning the nucleotide at position 51 of SEQ ID NO: 10), or a sequence comprising at least 95% sequence identity to SEQ ID NO: 10 and comprising a Thymine at nucleotide 51, because SEQ ID NO: 10 comprises the donor nucleotide (i.e. a Thymine) at nucleotide 51. Thus plants or plant cells comprising an introgression fragment which is from the CGMMV resistant *C. colocynthis* donor, may comprise the donor nucleotide for SNP10 (i.e. a Thymine at nucleotide 51) or "comprise SEQ ID NO: 10" or "a sequence comprising at least 95% sequence identity to SEQ ID NO: 10 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP10 in homozygous form, a diploid cell comprises two copies of SEQ ID NO: 10 (or of a sequence comprising at least 95% sequence identity to SEQ ID NO: 10), i.e. the "TT" genotype. A triploid plant or cell will comprise three copies and a tetraploid plant or cell four copies. Likewise, when the introgression fragment comprising the donor nucleotide for SNP10 in heterozygous form (only one chromosome of a pair of homologous chromosomes has the introgression), a diploid cell comprises one copy of SEQ ID NO: 10 (or of a sequence comprising at least 95% sequence identity to SEQ ID NO: 10). The other chromosome, lacking the introgression fragment comprises any of the other nucleotides, i.e. an Adenine, Cytosine or Guanine at nucleotide 51 of SEQ ID NO: 10 (SNP10), i.e. the sequence of the susceptible recurrent parent. This depends on which recurrent parent was used. In one aspect this is a Cytosine for SNP10, as indicated in Table 1, as this was the recurrent parent used in the backcrossing herein.

Thus "SNP11" or "SNP11 marker" refers herein to nucleotide 51 of SEQ ID NO: 11, or of a sequence comprising at least 95% sequence identity with SEQ ID NO: 11. When referring to the *C. colocynthis* donor nucleotide for SNP11 herein, i.e. an Adenine ('A') at nucleotide 51 of SEQ ID NO: 11 of a sequence comprising at least 95% sequence identity to SEQ ID NO: 11, one can equally refer to SEQ ID NO: 11 itself (without mentioning the nucleotide at position 51 of SEQ ID NO: 11), or a sequence comprising at least 95% sequence identity to SEQ ID NO: 11 and comprising an Adenine at nucleotide 51, because SEQ ID NO: 11 comprises the donor nucleotide (i.e. an Adenine) at nucleotide 51. Thus plants or plant cells comprising an introgression fragment which is from the CGMMV resistant *C. colocynthis* donor, may comprise the donor nucleotide for SNP11 (i.e. an Adenine at nucleotide 51) or "comprise SEQ ID NO: 11" or "a sequence comprising at least 95% sequence identity to SEQ ID NO: 11 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP11 in homozygous form, a diploid cell comprises two copies of SEQ ID NO: 11 (or of a sequence comprising at least 95% sequence identity to SEQ ID NO: 11), i.e. the "AA" genotype. A triploid plant or cell will comprise three copies and a tetraploid plant or cell four copies. Likewise, when the introgression fragment comprising the donor nucleotide for SNP11 in heterozygous form (only one chromosome of a pair of homologous chromosomes has the introgression), a diploid cell comprises one copy of SEQ ID NO: 11 (or of a sequence comprising at least 95% sequence identity to SEQ ID NO: 11). The other chromosome, lacking the introgression fragment comprises any of the other nucleotides, i.e. a Cytosine, Guanine or Thymine at nucleotide 51 of SEQ ID NO: 11 (SNP11), i.e. the sequence of the susceptible recurrent parent. This depends on which recurrent parent was used. In one aspect this is a Guanine for SNP11, as indicated in Table 1, as this was the recurrent parent used in the backcrossing herein.

Thus, "SNP12" or "SNP12 marker" refers herein to nucleotide 51 of SEQ ID NO: 12, or of a sequence comprising at least 95% sequence identity with SEQ ID NO: 12. When referring to the *C. colocynthis* donor nucleotide for SNP12 herein, i.e. a Thymine ('T') at nucleotide 51 of SEQ ID NO: 12 or of a sequence comprising at least 95% sequence identity to SEQ ID NO: 12, one can equally refer to SEQ ID NO: 12 itself (without mentioning the nucleotide at position 51 of SEQ ID NO: 12), or a sequence comprising at least 95% sequence identity to SEQ ID NO: 12 and comprising a Thymine at nucleotide 51, because SEQ ID NO: 12 comprises the donor nucleotide (i.e. a Thymine) at nucleotide 51. Thus plants or plant cells comprising an introgression fragment which is from the CGMMV resistant *C. colocynthis* donor, may comprise the donor nucleotide for SNP12 (i.e. a Thymine at nucleotide 51) or "comprise SEQ ID NO: 12" or "a sequence comprising at least 95% sequence identity to SEQ ID NO: 12 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP12 in homozygous form, a diploid cell comprises two copies of SEQ ID NO: 12 (or of a sequence comprising at least 95% sequence identity to SEQ ID NO: 12), i.e. the "TT" genotype. A triploid plant or cell will comprise three copies and a tetraploid plant or cell four copies. Likewise, when the introgression fragment comprising the donor nucleotide for SNP12 in heterozygous form (only one chromosome of a pair of homologous chromosomes has the introgression), a diploid cell comprises one copy of SEQ ID NO: 12 (or of a sequence comprising at least 95% sequence identity to SEQ ID NO: 12). The other chromosome, lacking the introgression fragment comprises any of the other nucleotides, i.e. an Adenine, Cytosine or Guanine at nucleotide 51 of SEQ ID NO: 12 (SNP12), i.e. the sequence of the susceptible recurrent parent. This depends on which recurrent parent was used. In one aspect this is a Cytosine for SNP12, as indicated in Table 1, as this was the recurrent parent used in the backcrossing herein.

SEQ ID NO: 10 (comprising SNP10), SEQ ID NO: 11 (comprising SNP11) and SEQ ID NO: 12 (comprising SNP12) are linked to the CGMMV resistance QTL5.2 on chromosome 5 of the donor. Marker SNP11 is most closely linked. An introgression fragment comprising CGMMV resistance from *C. colocynthis* therefore comprises in one aspect the resistant donor nucleotide (and the sequence comprising the donor nucleotide or a sequence comprising at least 95% sequence identity thereto and comprising the donor nucleotide) for one or more or all of the SNP markers of the group SNP10, SNP11 and SNP12, most preferably it comprises the resistant donor nucleotide for SNP markers SNP10 and/or SNP11 or for SNP11 and/or SNP12, even most preferably it comprises at least the resistant donor nucleotide for SNP11 (and thus SEQ ID NO: 11 or a sequence comprising at least 95% sequence identity to SEQ ID NO: 11 and comprising the donor nucleotide at nucleotide 51). Cultivated watermelon plants, plant cells and plant parts comprising such an introgression fragment, preferably in homozygous form, are an aspect of the invention.

Thus "SNP13" or "SNP13 marker" refers herein to nucleotide 51 of SEQ ID NO: 13, or of a sequence comprising at least 95% sequence identity with SEQ ID NO: 13. When referring to the *C. colocynthis* donor nucleotide for SNP13 herein, i.e. an Adenine ('A') at nucleotide 51 of SEQ ID NO: 13 of a sequence comprising at least 95% sequence identity to SEQ ID NO: 13, one can equally refer to SEQ ID NO: 13 itself (without mentioning the nucleotide at position 51 of SEQ ID NO: 13), or a sequence comprising at least 95% sequence identity to SEQ ID NO: 13 and comprising an Adenine at nucleotide 51, because SEQ ID NO: 13 comprises the donor nucleotide (i.e. an Adenine) at nucleotide 51. Thus plants or plant cells comprising an introgression fragment which is from the CGMMV resistant *C. colocynthis* donor, may comprise the donor nucleotide for SNP13 (i.e. an Adenine at nucleotide 51) or "comprise SEQ ID NO: 13" or "a sequence comprising at least 95% sequence identity to SEQ ID NO: 13 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP13 in homozygous form, a diploid cell comprises two copies of SEQ ID NO: 13 (or of a sequence comprising at least 95% sequence identity to SEQ ID NO: 13), i.e. the "AA" genotype. A triploid plant or cell will comprise three copies and a tetraploid plant or cell four copies. Likewise, when the introgression fragment comprising the donor nucleotide for SNP13 in heterozygous form (only one chromosome of a pair of homologous chromosomes has the introgression), a diploid cell comprises one copy of SEQ ID NO: 13 (or of a sequence comprising at least 95% sequence identity to SEQ ID NO: 13). The other chromosome, lacking the introgression fragment comprises any of the other nucleotides, i.e. an Cytosine, Guanine or Thymine at nucleotide 51 of SEQ ID NO: 13 (SNP13), i.e. the sequence of the susceptible recurrent parent. This depends on which recurrent parent was used. In one aspect this is a Guanine for SNP13, as indicated in Table 1, as this was the recurrent parent used in the backcrossing herein.

Thus "SNP14" or "SNP14 marker" refers herein to nucleotide 51 of SEQ ID NO: 14, or of a sequence comprising at least 95% sequence identity with SEQ ID NO: 14. When referring to the *C. colocynthis* donor nucleotide for SNP14 herein, i.e. an Adenine ('A') at nucleotide 51 of SEQ ID NO: 14 of a sequence comprising at least 95% sequence identity to SEQ ID NO: 14, one can equally refer to SEQ ID NO: 14 itself (without mentioning the nucleotide at position 51 of SEQ ID NO: 14), or a sequence comprising at least 95% sequence identity to SEQ ID NO: 14 and comprising an Adenine at nucleotide 51, because SEQ ID NO: 14 comprises the donor nucleotide (i.e. an Adenine) at nucleotide 51. Thus plants or plant cells comprising an introgression fragment which is from the CGMMV resistant *C. colocyn-*

*this* donor, may comprise the donor nucleotide for SNP14 (i.e. an Adenine at nucleotide 51) or "comprise SEQ ID NO: 14" or "a sequence comprising at least 95% sequence identity to SEQ ID NO: 14 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP14 in homozygous form, a diploid cell comprises two copies of SEQ ID NO: 14 (or of a sequence comprising at least 95% sequence identity to SEQ ID NO: 14), i.e. the "AA" genotype. A triploid plant or cell will comprise three copies and a tetraploid plant or cell four copies. Likewise, when the introgression fragment comprising the donor nucleotide for SNP14 in heterozygous form (only one chromosome of a pair of homologous chromosomes has the introgression), a diploid cell comprises one copy of SEQ ID NO: 14 (or of a sequence comprising at least 95% sequence identity to SEQ ID NO: 14). The other chromosome, lacking the introgression fragment comprises any of the other nucleotides, i.e. a Cytosine, Guanine or Thymine at nucleotide 51 of SEQ ID NO: 14 (SNP14), i.e. the sequence of the susceptible recurrent parent. This depends on which recurrent parent was used. In one aspect this is a Guanine for SNP14, as indicated in Table 1, as this was the recurrent parent used in the backcrossing herein.

Thus, "SNP15" or "SNP15 marker" refers herein to nucleotide 51 of SEQ ID NO: 15, or of a sequence comprising at least 95% sequence identity with SEQ ID NO: 15. When referring to the *C. colocynthis* donor nucleotide for SNP15 herein, i.e. a Guanine ('G') at nucleotide 51 of SEQ ID NO: 15 or of a sequence comprising at least 95% sequence identity to SEQ ID NO: 15, one can equally refer to SEQ ID NO: 15 itself (without mentioning the nucleotide at position 51 of SEQ ID NO: 15), or a sequence comprising at least 95% sequence identity to SEQ ID NO: 15 and comprising a Guanine at nucleotide 51, because SEQ ID NO: 15 comprises the donor nucleotide (i.e. a Guanine) at nucleotide 51. Thus plants or plant cells comprising an introgression fragment which is from the CGMMV resistant *C. colocynthis* donor, may comprise the donor nucleotide for SNP15 (i.e. a Guanine at nucleotide 51) or "comprise SEQ ID NO: 15" or "a sequence comprising at least 95% sequence identity to SEQ ID NO: 15 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP15 in homozygous form, a diploid cell comprises two copies of SEQ ID NO: 15 (or of a sequence comprising at least 95% sequence identity to SEQ ID NO: 15), i.e. the "GG" genotype. A triploid plant or cell will comprise three copies and a tetraploid plant or cell four copies. Likewise, when the introgression fragment comprising the donor nucleotide for SNP15 in heterozygous form (only one chromosome of a pair of homologous chromosomes has the introgression), a diploid cell comprises one copy of SEQ ID NO:15 (or of a sequence comprising at least 95% sequence identity to SEQ ID NO: 15). The other chromosome, lacking the introgression fragment comprises any of the other nucleotides, i.e. an Adenine, Cytosine or Thymine at nucleotide 51 of SEQ ID NO: 15 (SNP15), i.e. the sequence of the susceptible recurrent parent. This depends on which recurrent parent was used. In one aspect this is a Adenine for SNP15, as indicated in Table 1, as this was the recurrent parent used in the backcrossing herein.

Thus, "SNP16" or "SNP16 marker" refers herein to nucleotide 51 of SEQ ID NO: 16, or of a sequence comprising at least 95% sequence identity with SEQ ID NO: 16. When referring to the *C. colocynthis* donor nucleotide for SNP16 herein, i.e. a Guanine ('G') at nucleotide 51 of SEQ ID NO: 16 or of a sequence comprising at least 95% sequence identity to SEQ ID NO: 16, one can equally refer to SEQ ID NO: 16 itself (without mentioning the nucleotide at position 51 of SEQ ID NO: 16), or a sequence comprising at least 95% sequence identity to SEQ ID NO: 16 and comprising a Guanine at nucleotide 51, because SEQ ID NO: 16 comprises the donor nucleotide (i.e. a Guanine) at nucleotide 51. Thus plants or plant cells comprising an introgression fragment which is from the CGMMV resistant *C. colocynthis* donor, may comprise the donor nucleotide for SNP16 (i.e. a Guanine at nucleotide 51) or "comprise SEQ ID NO: 16" or "a sequence comprising at least 95% sequence identity to SEQ ID NO: 16 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP16 in homozygous form, a diploid cell comprises two copies of SEQ ID NO: 16 (or of a sequence comprising at least 95% sequence identity to SEQ ID NO: 16), i.e. the "GG" genotype. A triploid plant or cell will comprise three copies and a tetraploid plant or cell four copies. Likewise, when the introgression fragment comprising the donor nucleotide for SNP16 in heterozygous form (only one chromosome of a pair of homologous chromosomes has the introgression), a diploid cell comprises one copy of SEQ ID NO:16 (or of a sequence comprising at least 95% sequence identity to SEQ ID NO: 16). The other chromosome, lacking the introgression fragment comprises any of the other nucleotides, i.e. an Adenine, Cytosine or Thymine at nucleotide 51 of SEQ ID NO: 16 (SNP16), i.e. the sequence of the susceptible recurrent parent. This depends on which recurrent parent was used. In one aspect this is a Thymine for SNP16, as indicated in Table 1, as this was the recurrent parent used in the backcrossing herein.

Thus, "SNP17" or "SNP17 marker" refers herein to nucleotide 51 of SEQ ID NO: 17, or of a sequence comprising at least 95% sequence identity with SEQ ID NO: 17. When referring to the *C. colocynthis* donor nucleotide for SNP17 herein, i.e. a Thymine ('T') at nucleotide 51 of SEQ ID NO: 17 or of a sequence comprising at least 95% sequence identity to SEQ ID NO: 17, one can equally refer to SEQ ID NO: 17 itself (without mentioning the nucleotide at position 51 of SEQ ID NO: 17), or a sequence comprising at least 95% sequence identity to SEQ ID NO: 17 and comprising a Thymine at nucleotide 51, because SEQ ID NO: 17 comprises the donor nucleotide (i.e. a Thymine) at nucleotide 51. Thus plants or plant cells comprising an introgression fragment which is from the CGMMV resistant *C. colocynthis* donor, may comprise the donor nucleotide for SNP17 (i.e. a Thymine at nucleotide 51) or "comprise SEQ ID NO: 17" or "a sequence comprising at least 95% sequence identity to SEQ ID NO: 17 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP17 in homozygous form, a diploid cell comprises two copies of SEQ ID NO: 17 (or of a sequence comprising at least 95% sequence identity to SEQ ID NO: 17), i.e. the "TT" genotype. A triploid plant or cell will comprise three copies and a tetraploid plant or cell four copies. Likewise, when the introgression fragment comprising the donor nucleotide for SNP17 in heterozygous form (only one chromosome of a pair of homologous chromosomes has the introgression), a diploid cell comprises one copy of SEQ ID NO: 17 (or of a sequence comprising at least 95% sequence identity to SEQ ID NO: 17). The other chromosome, lacking the introgression fragment comprises any of the other nucleotides, i.e. an Adenine, Cytosine or Guanine at nucleotide 51 of SEQ ID NO: 17 (SNP17), i.e. the sequence of the susceptible recurrent parent. This depends on which recurrent parent was used. In one aspect this is a Cytosine for SNP17, as indicated in Table 1, as this was the recurrent parent used in the backcrossing herein.

Thus "SNP18" or "SNP18 marker" refers herein to nucleotide 51 of SEQ ID NO: 18, or of a sequence comprising at least 95% sequence identity with SEQ ID NO: 18. When referring to the *C. colocynthis* donor nucleotide for SNP18 herein, i.e. an Adenine ('A') at nucleotide 51 of SEQ ID NO: 18 of a sequence comprising at least 95% sequence identity to SEQ ID NO: 18, one can equally refer to SEQ ID NO: 18 itself (without mentioning the nucleotide at position 51 of SEQ ID NO: 18), or a sequence comprising at least 95% sequence identity to SEQ ID NO: 18 and comprising an Adenine at nucleotide 51, because SEQ ID NO: 18 comprises the donor nucleotide (i.e. an Adenine) at nucleotide 51. Thus plants or plant cells comprising an introgression fragment which is from the CGMMV resistant *C. colocynthis* donor, may comprise the donor nucleotide for SNP18 (i.e. an Adenine at nucleotide 51) or "comprise SEQ ID NO: 18" or "a sequence comprising at least 95% sequence identity to SEQ ID NO: 18 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP18 in homozygous form, a diploid cell comprises two copies of SEQ ID NO: 18 (or of a sequence comprising at least 95% sequence identity to SEQ ID NO: 18), i.e. the "AA" genotype. A triploid plant or cell will comprise three copies and a tetraploid plant or cell four copies. Likewise, when the introgression fragment comprising the donor nucleotide for SNP18 in heterozygous form (only one chromosome of a pair of homologous chromosomes has the introgression), a diploid cell comprises one copy of SEQ ID NO: 18 (or of a sequence comprising at least 95% sequence identity to SEQ ID NO: 18). The other chromosome, lacking the introgression fragment comprises any of the other nucleotides, i.e. an Cytosine, Guanine or Thymine at nucleotide 51 of SEQ ID NO: 18 (SNP18), i.e. the sequence of the susceptible recurrent parent. This depends on which recurrent parent was used. In one aspect this is a Guanine for SNP18, as indicated in Table 1, as this was the recurrent parent used in the backcrossing herein.

SEQ ID NO: 13 (comprising SNP13), SEQ ID NO: 14 (comprising SNP14), SEQ ID NO: 15 (comprising SNP15), SEQ ID NO: 16 (comprising SNP16), SEQ ID NO: 17 (comprising SNP17) and SEQ ID NO: 18 (comprising SNP18) are physically linked to the CGMMV resistance QTL7.1 on chromosome 7 of the donor. Marker SNP14 is most closely linked. An introgression fragment comprising CGMMV resistance from *C. colocynthis* therefore comprises the resistant donor nucleotide (and the sequence comprising the donor nucleotide or a sequence comprising at least 95% sequence identity thereto and comprising the donor nucleotide) for one or more or all of the SNP markers of the group of SNP13, SNP14, SNP15, SNP16, SNP17 and SNP18, more preferably it comprises the resistant donor nucleotide for one or more or all of the SNP markers selected from the group of SNP13, SNP14 and SNP15, more preferably it comprises the donor nucleotide for SNP13 and/or SNP14 or for SNP14 and/or SNP15, even more preferably it comprises at least the resistant donor nucleotide for SNP14 (and thus SEQ ID NO: 14 or a sequence comprising at least 95% sequence identity to SEQ ID NO: 14 and comprising the donor nucleotide at nucleotide 51). Cultivated watermelon plants, plant cells and plant parts comprising such an introgression fragment, in heterozygous or in homozygous form, are an aspect of the invention.

Further, "SNP19" or "SNP19 marker" refers herein to nucleotide 51 of SEQ ID NO: 19, or of a sequence comprising at least 95% sequence identity with SEQ ID NO: 19. When referring to the *C. colocynthis* donor nucleotide for SNP19 herein, i.e. a Cytosine ('C') at nucleotide 51 of SEQ ID NO: 19 of a sequence comprising at least 95% sequence identity to SEQ ID NO: 19, one can equally refer to SEQ ID NO: 19 itself (without mentioning the nucleotide at position 51 of SEQ ID NO: 19), or a sequence comprising at least 95% sequence identity to SEQ ID NO: 19 and comprising a Cytosine at nucleotide 51, because SEQ ID NO: 19 comprises the donor nucleotide (i.e. a Cytosine) at nucleotide 51. Thus plants or plant cells comprising an introgression fragment which is from the CGMMV resistant *C. colocynthis* donor, may comprise the donor nucleotide for SNP19 (i.e. a Cytosine at nucleotide 51) or "comprise SEQ ID NO: 19" or "a sequence comprising at least 95% sequence identity to SEQ ID NO: 19 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP19 in homozygous form, a diploid cell comprises two copies of SEQ ID NO: 19 (or of a sequence comprising at least 95% sequence identity to SEQ ID NO: 19), i.e. the "CC" genotype. A triploid plant or cell will comprise three copies and a tetraploid plant or cell four copies. Likewise, when the introgression fragment comprising the donor nucleotide for SNP19 in heterozygous form (only one chromosome of a pair of homologous chromosomes has the introgression), a diploid cell comprises one copy of SEQ ID NO: 19 (or of a sequence comprising at least 95% sequence identity to SEQ ID NO: 19). The other chromosome, lacking the introgression fragment comprises any of the other nucleotides, i.e. an Adenine, Guanine or Thymine at nucleotide 51 of SEQ ID NO: 19 (SNP19), i.e. the sequence of the susceptible recurrent parent. This depends on which recurrent parent was used. In one aspect this is a Thymine for SNP19, as indicated in Table 1, as this was the recurrent parent used in the backcrossing herein.

Thus, "SNP20" or "SNP20 marker" refers herein to nucleotide 51 of SEQ ID NO: 20, or of a sequence comprising at least 95% sequence identity with SEQ ID NO: 20. When referring to the *C. colocynthis* donor nucleotide for SNP20 herein, i.e. a Guanine ('G') at nucleotide 51 of SEQ ID NO: 20 or of a sequence comprising at least 95% sequence identity to SEQ ID NO: 20, one can equally refer to SEQ ID NO: 20 itself (without mentioning the nucleotide at position 51 of SEQ ID NO: 20), or a sequence comprising at least 95% sequence identity to SEQ ID NO: 20 and comprising a Guanine at nucleotide 51, because SEQ ID NO: 20 comprises the donor nucleotide (i.e. a Guanine) at nucleotide 51. Thus plants or plant cells comprising an introgression fragment which is from the CGMMV resistant *C. colocynthis* donor, may comprise the donor nucleotide for SNP20 (i.e. a Guanine at nucleotide 51) or "comprise SEQ ID NO: 20" or "a sequence comprising at least 95% sequence identity to SEQ ID NO: 20 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP20 in homozygous form, a diploid cell comprises two copies of SEQ ID NO: 20 (or of a sequence comprising at least 95% sequence identity to SEQ ID NO: 20), i.e. the "GG" genotype. A triploid plant or cell will comprise three copies and a tetraploid plant or cell four copies. Likewise, when the introgression fragment comprising the donor nucleotide for SNP20 in heterozygous form (only one chromosome of a pair of homologous chromosomes has the introgression), a diploid cell comprises one copy of SEQ ID NO: 20 (or of a sequence comprising at least 95% sequence identity to SEQ ID NO: 20). The other chromosome, lacking the introgression fragment comprises any of the other nucleotides, i.e. an Adenine, Cytosine or Thymine at nucleotide 51 of SEQ ID NO: 20 (SNP20), i.e. the sequence of the susceptible recurrent parent. This depends on which recurrent parent was used. In one aspect this is a Cytosine for SNP20, as indicated in Table 1, as this was the recurrent parent used in the backcrossing herein.

Thus, "SNP21" or "SNP21 marker" refers herein to nucleotide 51 of SEQ ID NO: 21, or of a sequence comprising at least 95% sequence identity with SEQ ID NO: 21. When referring to the *C. colocynthis* donor nucleotide for SNP21 herein, i.e. a Guanine ('G') at nucleotide 51 of SEQ ID NO: 21 or of a sequence comprising at least 95% sequence identity to SEQ ID NO: 21, one can equally refer to SEQ ID NO: 21 itself (without mentioning the nucleotide at position 51 of SEQ ID NO: 21), or a sequence comprising at least 95% sequence identity to SEQ ID NO: 21 and comprising a Guanine at nucleotide 51, because SEQ ID NO: 21 comprises the donor nucleotide (i.e. a Guanine) at nucleotide 51. Thus plants or plant cells comprising an introgression fragment which is from the CGMMV resistant *C. colocynthis* donor, may comprise the donor nucleotide for SNP21 (i.e. a Guanine at nucleotide 51) or "comprise SEQ ID NO: 21" or "a sequence comprising at least 95% sequence identity to SEQ ID NO: 21 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP21 in homozygous form, a diploid cell comprises two copies of SEQ ID NO: 21 (or of a sequence comprising at least 95% sequence identity to SEQ ID NO: 21), i.e. the "GG" genotype. A triploid plant or cell will comprise three copies and a tetraploid plant or cell four copies. Likewise, when the introgression fragment comprising the donor nucleotide for SNP21 in heterozygous form (only one chromosome of a pair of homologous chromosomes has the introgression), a diploid cell comprises one copy of SEQ ID NO: 21 (or of a sequence comprising at least 95% sequence identity to SEQ ID NO: 21). The other chromosome, lacking the introgression fragment comprises any of the other nucleotides, i.e. an Adenine, Cytosine or Thymine at nucleotide 51 of SEQ ID NO: 21 (SNP21), i.e. the sequence of the susceptible recurrent parent. This depends on which recurrent parent was used. In one aspect this is a Adenine for SNP21, as indicated in Table 1, as this was the recurrent parent used in the backcrossing herein.

Thus, "SNP22" or "SNP22 marker" refers herein to nucleotide 51 of SEQ ID NO: 22, or of a sequence comprising at least 95% sequence identity with SEQ ID NO: 22. When referring to the *C. colocynthis* donor nucleotide for SNP22 herein, i.e. a Cytosine ('C') at nucleotide 51 of SEQ ID NO: 22 of a sequence comprising at least 95% sequence identity to SEQ ID NO: 22, one can equally refer to SEQ ID NO: 22 itself (without mentioning the nucleotide at position 51 of SEQ ID NO: 22), or a sequence comprising at least 95% sequence identity to SEQ ID NO: 22 and comprising a Cytosine at nucleotide 51, because SEQ ID NO: 22 comprises the donor nucleotide (i.e. a Cytosine) at nucleotide 51. Thus plants or plant cells comprising an introgression fragment which is from the CGMMV resistant *C. colocynthis* donor, may comprise the donor nucleotide for SNP22 (i.e. a Cytosine at nucleotide 51) or "comprise SEQ ID NO: 22" or "a sequence comprising at least 95% sequence identity to SEQ ID NO: 22 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP22 in homozygous form, a diploid cell comprises two copies of SEQ ID NO: 22 (or of a sequence comprising at least 95% sequence identity to SEQ ID NO: 22), i.e. the "CC" genotype. A triploid plant or cell will comprise three copies and a tetraploid plant or cell four copies. Likewise, when the introgression fragment comprising the donor nucleotide for SNP22 in heterozygous form (only one chromosome of a pair of homologous chromosomes has the introgression), a diploid cell comprises one copy of SEQ ID NO: 22 (or of a sequence comprising at least 95% sequence identity to SEQ ID NO: 22). The other chromosome, lacking the introgression fragment comprises any of the other nucleotides, i.e. an Adenine, Guanine or Thymine at nucleotide 51 of SEQ ID NO: 22 (SNP22), i.e. the sequence of the susceptible recurrent parent. This depends on which recurrent parent was used. In one aspect this is a Thymine for SNP22, as indicated in Table 1, as this was the recurrent parent used in the backcrossing herein.

Thus, "SNP23" or "SNP23 marker" refers herein to nucleotide 51 of SEQ ID NO: 23, or of a sequence comprising at least 95% sequence identity with SEQ ID NO: 23. When referring to the C. colocynthis donor nucleotide for SNP23 herein, i.e. a Cytosine ('C') at nucleotide 51 of SEQ ID NO: 23 of a sequence comprising at least 95% sequence identity to SEQ ID NO: 23, one can equally refer to SEQ ID NO: 23 itself (without mentioning the nucleotide at position 51 of SEQ ID NO: 23), or a sequence comprising at least 95% sequence identity to SEQ ID NO: 23 and comprising a Cytosine at nucleotide 51, because SEQ ID NO: 23 comprises the donor nucleotide (i.e. a Cytosine) at nucleotide 51. Thus plants or plant cells comprising an introgression fragment which is from the CGMMV resistant C. colocynthis donor, may comprise the donor nucleotide for SNP23 (i.e. a Cytosine at nucleotide 51) or "comprise SEQ ID NO: 23" or "a sequence comprising at least 95% sequence identity to SEQ ID NO: 23 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP23 in homozygous form, a diploid cell comprises two copies of SEQ ID NO: 23 (or of a sequence comprising at least 95% sequence identity to SEQ ID NO: 23), i.e. the "CC" genotype. A triploid plant or cell will comprise three copies and a tetraploid plant or cell four copies. Likewise, when the introgression fragment comprising the donor nucleotide for SNP23 in heterozygous form (only one chromosome of a pair of homologous chromosomes has the introgression), a diploid cell comprises one copy of SEQ ID NO: 23 (or of a sequence comprising at least 95% sequence identity to SEQ ID NO: 23). The other chromosome, lacking the introgression fragment comprises any of the other nucleotides, i.e. an Adenine, Guanine or Thymine at nucleotide 51 of SEQ ID NO: 23 (SNP23), i.e. the sequence of the susceptible recurrent parent. This depends on which recurrent parent was used. In one aspect this is a Thymine for SNP23, as indicated in Table 1, as this was the recurrent parent used in the backcrossing herein.

Thus, "SNP24" or "SNP24 marker" refers herein to nucleotide 51 of SEQ ID NO: 24, or of a sequence comprising at least 95% sequence identity with SEQ ID NO: 24. When referring to the C. colocynthis donor nucleotide for SNP24 herein, i.e. a Guanine ('G') at nucleotide 51 of SEQ ID NO: 24 or of a sequence comprising at least 95% sequence identity to SEQ ID NO: 24, one can equally refer to SEQ ID NO: 24 itself (without mentioning the nucleotide at position 51 of SEQ ID NO: 24), or a sequence comprising at least 95% sequence identity to SEQ ID NO: 24 and comprising a Guanine at nucleotide 51, because SEQ ID NO: 24 comprises the donor nucleotide (i.e. a Guanine) at nucleotide 51. Thus plants or plant cells comprising an introgression fragment which is from the CGMMV resistant C. colocynthis donor, may comprise the donor nucleotide for SNP24 (i.e. a Guanine at nucleotide 51) or "comprise SEQ ID NO: 24" or "a sequence comprising at least 95% sequence identity to SEQ ID NO: 24 and comprising the donor nucleotide at nucleotide 51, or at the equivalent position when aligned pairwise". The equivalent position when pairwise aligned may be a slightly different position due to e.g. nucleotide insertions or deletions, e.g. it may be nucleotide 49, 50 or 52 or 53. Sequence identity is preferably determined by pairwise alignment, using e.g. the Emboss program 'Needle". When the introgression fragment comprising the donor nucleotide for SNP24 in homozygous form, a diploid cell comprises two copies of SEQ ID NO: 24 (or of a sequence comprising at least 95% sequence identity to SEQ ID NO: 24), i.e. the "GG" genotype. A triploid plant or cell will comprise three copies and a tetraploid plant or cell four copies. Likewise, when the introgression fragment comprising the donor nucleotide for SNP24 in heterozygous form (only one chromosome of a pair of homologous chromosomes has the introgression), a diploid cell comprises one copy of SEQ ID NO: 24 (or of a sequence comprising at least 95% sequence identity to SEQ ID NO: 24). The other chromosome, lacking the introgression fragment comprises any of the other nucleotides, i.e. an Adenine, Cytosine or Thymine at nucleotide 51 of SEQ ID NO: 24 (SNP24), i.e. the sequence of the susceptible recurrent parent. This depends on which recurrent parent was used. In one aspect this is a Thymine for SNP24, as indicated in Table 1, as this was the recurrent parent used in the backcrossing herein.

SEQ ID NO: 19 (comprising SNP19), SEQ ID NO: 20 (comprising SNP20), SEQ ID NO: 21 (comprising SNP21), SEQ ID NO: 22 (comprising SNP22), SEQ ID NO: 23 (comprising SNP23) and SEQ ID NO: 24 (comprising SNP24) are physically linked to the CGMMV resistance QTL9.1 on chromosome 9 of the donor. Marker SNP22 is most closely linked. An introgression fragment comprising CGMMV resistance from C. colocynthis therefore comprises the resistant donor nucleotide (and the sequence comprising the donor nucleotide or a sequence comprising at least 95% sequence identity thereto and comprising the donor nucleotide) for one or more or all of the SNP markers of the group of SNP19, SNP20, SNP21, SNP22, SNP23 and SNP24, more preferably it comprises the resistant donor nucleotide for one or more or all of the SNP markers selected from the group of SNP21, SNP22, SNP23, more preferably it comprises the donor nucleotide for SNP21 and/or SNP22 or for SNP22 and/or SNP23, even more preferably it comprises at least the resistant donor nucleotide for SNP22 (and thus SEQ ID NO: 22 or a sequence comprising at least 95% sequence identity to SEQ ID NO: 22 and comprising the donor nucleotide at nucleotide 51). Cultivated watermelon plants, plant cells and plant parts comprising such an introgression fragment, in heterozygous or in homozygous form, are an aspect of the invention.

In one aspect a cultivated watermelon plant, plant part or plant cell is provided comprising an introgression fragment from chromosome 7 and/or on chromosome 9 of a CGMMV resistant donor plant of the species Citrullus colocynthis, wherein the introgression fragment on chromosome 7 comprises QTL7.1 from the donor and a sequence of the CGMMV resistant donor plant in-between SNP13 and SNP18, or in-between SNP13 and SNP17, or in-between SNP13 and SNP16, or in-between SNP13 and SNP15, or in-between SNP13 and SNP14, or in-between SNP14 and SNP15, or in-between SNP14 and SNP16, or in-between SNP14 and SNP17 or in-between SNP14 and SNP18; preferably the introgression fragment comprises a sequence of the CGMMV resistant donor in-between SNP13 and SNP15, or in-between SNP13 and SNP14 or in-between SNP14 and SNP15; and/or wherein the introgression fragment on chromosome 9 comprises QTL9.1 from the donor and a sequence of the CGMMV resistant donor plant in-between SNP19 and SNP24, or in-between SNP19 and SNP23, or in-between SNP19 and SNP22, or in-between SNP20 and SNP24, or in-between SNP20 and SNP23, or in-between SNP20 and SNP22, or in-between SNP21 and SNP24, or in-between SNP21 and SNP23, or in-between SNP21 and SNP22, or in-between SNP22 and SNP24, or in-between SNP22 and SNP23; preferably the introgression fragment comprises a sequence of the CGMMV resistant donor in-between SNP21 and SNP23, or in-between SNP21 and SNP22 or in-between SNP22 and SNP23.

When referring herein to the introgression fragment comprising the donor chromosome sequence or a donor sequence (and the QTL) "in-between" two SNPs (Single Nucleotide Polymorphisms), this encompasses in one aspect that one or both of the two SNPs themselves are also from the resistant donor, i.e. have the donor nucleotide, but it is also encompassed that neither of the two SNPs are from the resistant donor, but that only the chromosomal sequence in-between the two SNPs is from the donor and comprises the QTL. The SNP marker nucleotides "flanking" the introgression fragment comprising the QTL may, thus, in one aspect be part of the introgression fragment (from the donor) or may be part of the recipient chromosome (from the recipient).

So, for example when the introgression fragment from the donor is "in-between SNP13 and SNP18", SNP13 and/or SNP18 may comprise the donor nucleotide, but the introgression fragment may also be shorter and comprise the susceptible nucleotide of e.g. the recurrent parent for SNP13 and/or SNP18. For example, only the sequence and the SNPs lying in-between SNP13 and SNP18 may be from the donor, so, e.g. SNP14, SNP15, SNP16 and SNP17 may be from the donor, or only SNP14, SNP15 and SNP16 may be from the donor, or only one or two of the SNP markers may be from the donor, e.g. only one or two of SNP14, SNP15 and SNP16. The introgression fragment comprising the QTL may therefore not comprise all of the donor nucleotides for the SNPs of the group SNP13 to SNP18.

In one aspect the introgression fragment comprises at least one, optionally at least two or all three, of donor nucleotides of SNP13, SNP14 and/or SNP15, i.e. the introgression fragment comprises at least one, optionally at least two or three of the sequences SEQ ID NO:13 (or a sequence comprising at least 95% sequence identity to SEQ ID NO: 13 and comprising a Adenine at nucleotide 51 or at the equivalent position), SEQ ID NO: 14 (or a sequence comprising at least 95% sequence identity to SEQ ID NO: 14 and comprising a Adenine at nucleotide 51 or at the equivalent position) and/or SEQ ID NO: 15 (or a sequence comprising at least 95% sequence identity to SEQ ID NO: 15 and comprising a Guanine at nucleotide 51 or at the equivalent position). The introgression fragment obviously comprises the QTL7.1 from the donor, which confers CGMMV resistance to an otherwise susceptible watermelon plant.

Likewise, for example when the introgression fragment from the donor is "in-between SNP19 and SNP24", SNP19 and/or SNP24 may comprise the donor nucleotide, but the introgression fragment may also be shorter and comprise the susceptible nucleotide of e.g. the recurrent parent for SNP19 and/or SNP24. For example, only sequence and the SNPs lying in-between SNP19 and SNP24 may be from the donor, so, e.g. SNP20, SNP21, SNP22 and SNP23 may be from the donor, or only SNP21, SNP22 and SNP23 may be from the donor, or only one or two of the SNP markers may be from the donor, e.g. one or two of SNP21, SNP22 and SNP23. The introgression fragment comprising the QTL may therefore not comprise all of the donor nucleotides for the SNPs of the group SNP19 to SNP24. In one aspect the introgression fragment comprises at least one, optionally at least two or all three, of donor nucleotides of SNP21, SNP22 and/or SNP23, i.e. the introgression fragment comprises at least one, optionally at least two or three of the sequences SEQ ID NO:21 (or a sequence comprising at least 95% sequence identity to SEQ ID NO: 21 and comprising a Guanine at nucleotide 51 or at the equivalent position), SEQ ID NO: 22 (or a sequence comprising at least 95% sequence identity to SEQ ID NO: 22 and comprising a Cytosine at nucleotide 51 or at the equivalent position) and/or SEQ ID NO: 23 (or a sequence comprising at least 95% sequence identity to SEQ ID NO: 23 and comprising a Cytosine at nucleotide 51 or at the equivalent position). The introgression fragment obviously comprises the QTL9.1 from the donor, which confers CGMMV resistance to an otherwise susceptible watermelon plant.

In one aspect a cultivated watermelon plant, plant part or plant cell is provided comprising an introgression fragment from chromosome 7 and/or on chromosome 9 of a CGMMV resistant donor plant of the species *Citrullus colocynthis*, wherein the introgression fragment on chromosome 7 comprises a sequence of the CGMMV resistant donor plant for SNP14 (an Adenine at nucleotide 51 in SEQ ID NO: 14) or comprises SEQ ID NO: 14 or a sequence comprising at least 95% sequence identity to SEQ ID NO: 14 and comprises an Adenine at nucleotide 51, and/or wherein the introgression fragment on chromosome 9 comprises a sequence of the CGMMV resistant donor plant for SNP22 (a Cytosine at nucleotide 51 in SEQ ID NO: 22) or comprises SEQ ID NO: 22 or a sequence comprising at least 95% sequence identity to SEQ ID NO:22 and comprises a Cytosine at nucleotide 51.

In one aspect the invention provides a cultivated watermelon plant, plant part or plant cell comprising an introgression fragment from chromosome 7 and/or on chromosome 9 of a CGMMV resistant donor plant of the species *Citrullus colocynthis*, wherein the introgression fragment on chromosome 7 comprises QTL7.1 from the donor and comprises an Adenine at nucleotide 51 of SEQ ID NO: 13 or of a sequence comprising at least 95% sequence identity to SEQ ID NO: 13, and/or a Adenine at nucleotide 51 of SEQ ID NO: 14 or of a sequence comprising at least 95% sequence identity to SEQ ID NO:14, and/or a Guanine at nucleotide 51 of SEQ ID NO: 15 or of a sequence comprising at least 95% sequence identity to SEQ ID NO:15, and/or a Guanine at nucleotide 51 of SEQ ID NO: 16 or of a sequence comprising at least 95% sequence identity to SEQ ID NO:16, and/or a Thymine at nucleotide 51 of SEQ ID NO: 17 or of a sequence comprising at least 95% sequence identity to SEQ ID NO: 17, and/or an Adenine at nucleotide 51 of SEQ ID NO: 18 or of a sequence comprising at least 95% sequence identity to SEQ ID NO: 18; preferably the introgression fragment on chromosome 7 comprises an Adenine at nucleotide 51 of SEQ ID NO: 13 or of a sequence comprising at least 95% sequence identity to SEQ ID NO: 13, and/or a Adenine at nucleotide 51 of SEQ ID NO: 14 or of a sequence comprising at least 95% sequence identity to SEQ ID NO:14, and/or a Guanine at nucleotide 51 of SEQ ID NO: 15 or of a sequence comprising at least 95% sequence identity to SEQ ID NO:15; and/or wherein the introgression fragment on chromosome 9 comprises QTL9.1 from the donor and comprises a Cytosine at nucleotide 51 of SEQ ID NO: 19 or of a sequence comprising at least 95% sequence identity to SEQ ID NO: 19, and/or a Guanine at nucleotide 51 of SEQ ID NO: 20 or of a sequence comprising at least 95% sequence identity to SEQ ID NO: 20, and/or a Guanine at nucleotide 51 of SEQ ID NO: 21 or of a sequence comprising at least 95% sequence identity to SEQ ID NO: 21, and/or a Cytosine at nucleotide 51 of SEQ ID NO: 22 or of a sequence comprising at least 95% sequence identity to SEQ ID NO: 22, and/or a Cytosine at nucleotide 51 of SEQ ID NO: 23 or of a sequence comprising at least 95% sequence identity to SEQ ID NO: 23, and/or a Guanine at nucleotide 51 of SEQ ID NO: 24 or of a sequence comprising at least 95% sequence identity to SEQ ID NO: 24; preferably the introgression fragment on chromosome 9 comprises a Guanine at nucleotide 51 of SEQ ID NO: 21 or of a sequence comprising at least 95% sequence identity to SEQ ID NO: 21, and/or a Cytosine at nucleotide 51 of SEQ ID NO: 22 or of a sequence comprising at least 95% sequence identity to SEQ ID NO: 22, and/or a Cytosine at nucleotide 51 of SEQ ID NO: 23 or of a sequence comprising at least 95% sequence identity to SEQ ID NO: 23.

As the marker most closely linked to QTL7.1 is SNP14, the introgression fragment preferably comprises QTL7.1 and at least one, two or all three donor markers selected from SNP13, SNP14 and SNP15, i.e. an Adenine at nucleotide 51 of SEQ ID NO: 13 or of a sequence comprising at least 95% sequence identity to SEQ ID NO: 13, and/or a Adenine at nucleotide 51 of SEQ ID NO: 14 or of a sequence comprising at least 95% sequence identity to SEQ ID NO:14, and/or a Guanine at nucleotide 51 of SEQ ID NO: 15 or of a sequence comprising at least 95% sequence identity to SEQ ID NO:15.

As the marker most closely linked to QTL9.1 is SNP22, the introgression fragment preferably comprises QTL9.1 and at least one, two or all three donor markers selected from SNP21, SNP22 and SNP23, i.e. a. Guanine at nucleotide 51 of SEQ ID NO: 21 or of a sequence comprising at least 95% sequence identity to SEQ ID NO: 21, and/or a Cytosine at nucleotide 51 of SEQ ID NO: 22 or of a sequence comprising at least 95% sequence identity to SEQ ID NO: 22, and/or a Cytosine at nucleotide 51 of SEQ ID NO: 23 or of a sequence comprising at least 95% sequence identity to SEQ ID NO: 23.

Whether the QTL is present on the introgression fragment can be determined phenotypically, using a CGMMV test as described herein and in the examples. So, for example a plant comprising one or more of the donor nucleotides for any of the described SNPs can be crossed with a susceptible plant and the progeny (e.g. F1) can be analysed for CGMMV resistance. QTL7.1 and QTL9.1 are both dominant, so that the phenotype is already seen in F1 progeny. Plants and plant cells comprising QTL7.1 or QTL9.1 alone are an embodiment of the invention, as well as plants comprising both QTLs in their genome, i.e. comprising two recombinant chromosomes, one recombinant chromosome 7, comprising an introgression fragment from a CGMMV resistant *C. colocynthis* donor, and one recombinant chromosome 9, comprising an introgression fragment from a CGMMV resistant *C. colocynthis* donor, preferably from the same *C. colocynthis* donor (although this is not required, they may also be from different donors).

The cultivated watermelon plants comprising QTL7.1 and/or QTL9.1 are CGMMV resistant and preferably have a CGMMV score of 3, or more preferably of 4 (no symptoms), when tested as described. Preferably the plants or scions derived from the plants comprise extremely low levels of CGMMV virus in the leaves and optionally in the fruits, significantly lower than a susceptible control treated in the same way. In one aspect the seeds produced in the fruits of such plants remain CGMMV virus free.

The cultivated watermelon plant or plant cell according to the invention comprises the introgression fragment on chromosome 7 in homozygous or in heterozygous form and/or comprises the introgression fragment on chromosome 9 is in homozygous form or in heterozygous form. Making F1 hybrid varieties is easiest of the introgression fragment or fragments is/are in homozygous form in the inbred parent lines. The F1 hybrid, made by crossing the two homozygous inbred lines comprises the QTL(s) then also in homozygous form.

In one aspect the present invention relates to cultivated watermelon plant cells or watermelon plants (or plant parts) comprising an introgression fragment from chromosome 1 (comprising QTL1.1 from the donor), 4 (comprising QTL4.1), 5 (comprising QTL5.2), 7 (comprising QTL7.1) and/or 9 (comprising QTL9.1) of a CGMMV resistant donor plant, wherein the introgression fragment confers CGMMV resistance and the introgression fragment is detectable by (comprises) the SNP genotype of the donor plant for one or more (or all) of the following SNPs: SNP1, SNP2, SNP3, SNP4, SNP5 and/or SNP6 for the fragment on chromosome 1; and/or one or more of SNP7, SNP8 and/or SNP9 for the fragment on chromosome 4; and/or one or more of SNP10, SNP11 and/or SNP12 for the fragment on chromosome 5; and/or one or more of SNP13, SNP14, SNP15, SNP16, SNP17 and/or SNP18 for the fragment on chromosome 7; and/or one or more of SNP19, SNP20, SNP21, SNP22, SNP23 and/or SNP24 for the fragment on chromosome 9. The CGMMV resistance conferring QTL is present on the introgression fragment as can be determined by a CGMMV resistance assay as described e.g. in the Examples. The cultivated watermelon plant comprising an introgression fragment from chromosome 7 (comprising QTL7.1) and/or from chromosome 9 (comprising QTL9.1), described further above, may optionally also comprise one or more of the QTLs selected from QTL1.1, QTL4.1 and/or QTL5.2.

Therefore, in one aspect a cultivated watermelon plant, plant part or plant cell is provided further comprising an introgression fragment from chromosome 1 and/or on chromosome 4 and/or chromosome 5 of a CGMMV resistant donor plant of the species *Citrullus colocynthis*, wherein the introgression fragment on chromosome 1 comprises QTL1.1 from the donor and a sequence of the CGMMV resistant donor plant in-between SNP1 and SNP6, or in-between SNP1 and SNP5, or in-between SNP1 and SNP4, or in-between SNP2 and SNP6, or in-between SNP2 and SNP5, or in-between SNP2 and SNP4, or in-between SNP3 and SNP6, or in-between SNP3 and SNP5 or in-between SNP3 and SNP4, or in-between SNP4 and SNP6, or in-between SNP4 and SNP5 or in-between SNP5 and SNP6; preferably the introgression fragment comprises a sequence of the CGMMV resistant donor in-between SNP4 and SNP6, or in-between SNP4 and SNP5 or in-between SNP5 and SNP6; and/or wherein the introgression fragment on chromosome 4 comprises QTL4.1 from the donor and a sequence of the CGMMV resistant donor plant in-between SNP7 and SNP9, or in-between SNP8 and SNP8, or in-between SNP7 and SNP8; and/or wherein the introgression fragment on chromosome 5 comprises QTL5.2 from the donor and a sequence of the CGMMV resistant donor plant in-between SNP10 and SNP12, or in-between SNP10 and SNP11, or in-between SNP11 and SNP12.

Preferably these introgression fragments, comprising QTL1.1, QTL4.1 or QTL5.2 are present in homozygous form in the plant. They may also be present in a cultivated watermelon plant individually or combined, e.g. QTL1.1 and QTL4.1 or QTL1.1 and QTL5.2 or QTL4.1 and QTL5.2, or all three combined. As mentioned, optionally also one or both of QTL7.1 and QTL9.1 may be combined in one plant with one or more of these recessive QTLs.

When the introgression fragment from the donor is mentioned to be "in-between SNP1 and SNP6", for example, SNP1 and/or SNP6 may comprise the donor nucleotide, but the introgression fragment may also be shorter and comprise the susceptible nucleotide of e.g. the recurrent parent for SNP1 and/or SNP6. For example, only the sequence and the SNPs lying in-between SNP1 and SNP6 may be from the donor, so, e.g. SNP2, SNP3, SNP4 and SNP5 may be from the donor, or only SNP3, SNP4 and SNP5 may be from the donor, or only one or two of the SNP markers may be from the donor, e.g. only one or two of SNP3, SNP4 and SNP5. The introgression fragment comprising the QTL may therefore not comprise all of the donor nucleotides for the SNPs of the group SNP1 to SNP6.

In one aspect the introgression fragment comprising QTL1.1 comprises at least one, optionally at least two or all three, of donor nucleotides of SNP4, SNP5 and/or SNP6, i.e. the introgression fragment comprises at least one, optionally at least two or three of the sequences SEQ ID NO:4 (or a sequence comprising at least 95% sequence identity to SEQ ID NO: 4 and comprising a Cytosine at nucleotide 51 or at the equivalent position), SEQ ID NO: 5 (or a sequence comprising at least 95% sequence identity to SEQ ID NO: 5 and comprising a Guanine at nucleotide 51 or at the equivalent position) and/or SEQ ID NO: 6 (or a sequence comprising at least 95% sequence identity to SEQ ID NO: 6 and comprising a Thymine at nucleotide 51 or at the equivalent position). The introgression fragment obviously comprises the QTL1.1 from the donor, which confers CGMMV resistance to an otherwise susceptible watermelon plant.

Likewise, for example when the introgression fragment comprising QTL4.1 from the donor is "in-between SNP7 and SNP9", SNP7 and/or SNP9 may comprise the donor nucleotide, but the introgression fragment may also be shorter and comprise the susceptible nucleotide of e.g. the recurrent parent for SNP7 and/or SNP9. For example, only sequence and the SNPs lying in-between SNP7 and SNP9 may be from the donor, so, e.g. SNP8 may be from the donor. The introgression fragment comprising the QTL4.1 may therefore not comprise all of the donor nucleotides for the SNPs of the group SNP7 to SNP9. In one aspect the introgression fragment comprises at least one, optionally at least two or all three, of donor nucleotides of SNP7, SNP8 and/or SNP9, i.e. the introgression fragment comprises at least one, optionally at least two or three of the sequences SEQ ID NO:7 (or a sequence comprising at least 95% sequence identity to SEQ ID NO: 7 and comprising a Thymine at nucleotide 51 or at the equivalent position), SEQ ID NO: 8 (or a sequence comprising at least 95% sequence identity to SEQ ID NO: 8 and comprising a Cytosine at nucleotide 51 or at the equivalent position) and/or SEQ ID NO: 9 (or a sequence comprising at least 95% sequence identity to SEQ ID NO: 9 and comprising an Adenine at nucleotide 51 or at the equivalent position). The introgression fragment obviously comprises the QTL4.1 from the donor, which confers CGMMV resistance to an otherwise susceptible watermelon plant.

Likewise, for example when the introgression fragment comprising QTL5.2 from the donor is "in-between SNP10 and SNP12", SNP10 and/or SNP12 may comprise the donor nucleotide, but the introgression fragment may also be shorter and comprise the susceptible nucleotide of e.g. the recurrent parent for SNP10 and/or SNP12. For example, only sequence and the SNPs lying in-between SNP10 and SNP12 may be from the donor, so, e.g. SNP11 may be from the donor. The introgression fragment comprising the QTL5.2 may therefore not comprise all of the donor nucleotides for the SNPs of the group SNP10 to SNP12. In one aspect the introgression fragment comprises at least one, optionally at least two or all three, of donor nucleotides of SNP10, SNP11 and/or SNP12, i.e. the introgression fragment comprises at least one, optionally at least two or three of the sequences SEQ ID NO:10 (or a sequence comprising at least 95% sequence identity to SEQ ID NO: 10 and comprising a Thymine at nucleotide 51 or at the equivalent position), SEQ ID NO: 11 (or a sequence comprising at least 95% sequence identity to SEQ ID NO: 11 and comprising a Adenine at nucleotide 51 or at the equivalent position) and/or SEQ ID NO: 12 (or a sequence comprising at least 95% sequence identity to SEQ ID NO: 12 and comprising an Thymine at nucleotide 51 or at the equivalent position). The introgression fragment obviously comprises the QTL5.2 from the donor, which confers CGMMV resistance to an otherwise susceptible watermelon plant.

In one aspect a cultivated watermelon plant, plant part or plant cell is provided comprising an introgression fragment from chromosome 1 (comprising QTL1.1) and/or on chromosome 4 (comprising QTL4.1) and/or from chromosome 5 (comprising QTL5.2) of a CGMMV resistant donor plant of the species *Citrullus colocynthis*, wherein the introgression fragment on chromosome 1 comprises a sequence of the CGMMV resistant donor plant for SNP5 (an Guanine at nucleotide 51 in SEQ ID NO: 5) or comprises SEQ ID NO: 5 or a sequence comprising at least 95% sequence identity to SEQ ID NO: 5 and comprises an Guanine at nucleotide 51, and/or wherein the introgression fragment on chromosome 4 comprises a sequence of the CGMMV resistant donor plant for SNP8 (a Cytosine at nucleotide 51 in SEQ ID NO: 22) or comprises SEQ ID NO: 8 or a sequence comprising at least 95% sequence identity to SEQ ID NO:8 and comprises a Cytosine at nucleotide 51; and/or wherein the introgression fragment on chromosome 5 comprises a sequence of the CGMMV resistant donor plant for SNP11 (an Adenine at nucleotide 51 in SEQ ID NO: 11) or comprises SEQ ID NO: 11 or a sequence comprising at least 95% sequence identity to SEQ ID NO:11 and comprises a Adenine at nucleotide 51.

In one aspect the invention provides a cultivated watermelon plant, plant part or plant cell comprising an introgression fragment from chromosome 1 and/or on chromosome 4 and/or on chromosome 5 of a CGMMV resistant donor plant of the species *Citrullus colocynthis*, wherein the introgression fragment on chromosome 1 comprises QTL1.1 from the donor and comprises an Cytosine at nucleotide 51 of SEQ ID NO: 1 or of a sequence comprising at least 95% sequence identity to SEQ ID NO: 1, and/or a Guanine at nucleotide 51 of SEQ ID NO: 2 or of a sequence comprising at least 95% sequence identity to SEQ ID NO:2, and/or a Cytosine at nucleotide 51 of SEQ ID NO: 3 or of a sequence comprising at least 95% sequence identity to SEQ ID NO:3, and/or a Cytosine at nucleotide 51 of SEQ ID NO: 4 or of a sequence comprising at least 95% sequence identity to SEQ ID NO:4, and/or a Guanine at nucleotide 51 of SEQ ID NO: 5 or of a sequence comprising at least 95% sequence identity to SEQ ID NO: 5, and/or an Thymine at nucleotide 51 of SEQ ID NO: 6 or of a sequence comprising at least 95% sequence identity to SEQ ID NO: 6; preferably the introgression fragment on chromosome 1 comprises a Cytosine at nucleotide 51 of SEQ ID NO: 4 or of a sequence comprising at least 95% sequence identity to SEQ ID NO:4, and/or a Guanine at nucleotide 51 of SEQ ID NO: 5 or of a sequence comprising at least 95% sequence identity to SEQ ID NO: 5, and/or an Thymine at nucleotide 51 of SEQ ID NO: 6 or of a sequence comprising at least 95% sequence identity to SEQ ID NO: 6; and/or wherein the introgression fragment on chromosome 4 comprises QTL4.1 from the donor and comprises a Thymine at nucleotide 51 of SEQ ID NO: 7 or of a sequence comprising at least 95% sequence identity to SEQ ID NO: 7, and/or a Cytosine at nucleotide 51 of SEQ ID NO: 8 or of a sequence comprising at least 95% sequence identity to SEQ ID NO: 8, and/or a Adenine at nucleotide 51 of SEQ ID NO: 9 or of a sequence comprising at least 95% sequence identity to SEQ ID NO: 9; and/or wherein the introgression fragment on chromosome 5 comprises QTL5.1 from the donor and comprises a Thymine at nucleotide 51 of SEQ ID NO: 10 or of a sequence comprising at least 95% sequence identity to SEQ ID NO: 10, and/or a Adenine at nucleotide 51 of SEQ ID NO: 11 or of a sequence comprising at least 95% sequence identity to SEQ ID NO: 11, and/or a Thymine at nucleotide 51 of SEQ ID NO: 12 or of a sequence comprising at least 95% sequence identity to SEQ ID NO: 12.

As the marker most closely linked to QTL1.1 is SNP5, the introgression fragment preferably comprises QTL1.1 and at least one, two or all three donor markers selected from SNP4, SNP5 and SNP6, i.e. an Cytosine at nucleotide 51 of SEQ ID NO: 4 or of a sequence comprising at least 95% sequence identity to SEQ ID NO: 4, and/or a Guanine at nucleotide 51 of SEQ ID NO: 5 or of a sequence comprising at least 95% sequence identity to SEQ ID NO:5, and/or a Thymine at nucleotide 51 of SEQ ID NO: 6 or of a sequence comprising at least 95% sequence identity to SEQ ID NO:6.

As the marker most closely linked to QTL4.1 is SNP8, the introgression fragment preferably comprises QTL4.1 and at least one, two or all three donor markers selected from SNP7, SNP8 and SNP5, i.e. a. Thymine at nucleotide 51 of SEQ ID NO: 7 or of a sequence comprising at least 95% sequence identity to SEQ ID NO: 7, and/or a Cytosine at nucleotide 51 of SEQ ID NO: 8 or of a sequence comprising at least 95% sequence identity to SEQ ID NO: 8, and/or an Adenine at nucleotide 51 of SEQ ID NO: 9 or of a sequence comprising at least 95% sequence identity to SEQ ID NO: 9.

As the marker most closely linked to QTL5.2 is SNP11, the introgression fragment preferably comprises QTL5.2 and at least one, two or all three donor markers selected from SNP10, SNP11 and SNP12, i.e. a. Thymine at nucleotide 51 of SEQ ID NO: 10 or of a sequence comprising at least 95% sequence identity to SEQ ID NO: 10, and/or a Adenine at nucleotide 51 of SEQ ID NO: 11 or of a sequence comprising at least 95% sequence identity to SEQ ID NO: 11, and/or an Thymine at nucleotide 51 of SEQ ID NO: 12 or of a sequence comprising at least 95% sequence identity to SEQ ID NO: 12.

As mentioned, in one aspect the cultivated watermelon plant or plant cell comprises the introgression fragment(s) from a *Citrullus colocynthis* accession. This may be any CGMMV resistant *C. colocynthis* accession, especially an accession which has a CGMMV score of 4 (no symptoms) when inoculated with CGMMV as described. Although in one aspect the introgression fragments are present in, and derivable from, NCIMB 42624, the *C. colocynthis* donor does not necessarily need to be the accession having been deposited under accession number NCIMB 42624 (or progeny thereof). The skilled person can for example identify any other *C. colocynthis* accession which has a CGMMV score of 4 (no symptoms) and/or which comprises a SNP marker profile identical or very similar to that of NCIMB 42624 for any of the QTLs, which would mean that the same QTL or QTLs (selected from QTL1.1, QTL4.1, QTL5.2, QTL7.1 and QTL9.1) are present in that donor. Such a *C. colocynthis* accession does not have to have exactly the same SNP genotype as NCIMB 42624. It may for example be heterozygous for some SNP markers, and would need to be selfed one or more times to select a progeny homozygous for one or more or all of the QTL(s). Also, the donor may vary somewhat in the SNP genotype, e.g. regarding QTL7.1 or QTL9.1 it may only comprise five, four or three of the donor SNP markers of SNP13 to SNP18 (linked to QTL7.1) or of SNP19 to SNP24 (linked to QTL9.1).

Examples of *C. colocynthis* accessions which may comprise CGMMV resistance (i.e. one or more of QTL1.1, QTL4.1, QTL5.2, QTL7.1 and QTL9.1 are accessions which contain plants that have a score of 4 (no symptoms). Such accessions, or selfing progeny of selected individual plants with a score of 4, can be tested for the genotype of the SNP markers provided herein in Table 1 and Table 6. It is noted that such accessions themselves are of course not part of the invention as they generally produce small, white fleshed fruits with low brix (2 or 3° brix) and are not agronomically useful, but only QTLs transferred (introgressed) individually or in combination into crop plants, such as cultivated watermelon, to confer CGMMV resistance to cultivated watermelon plants having good agronomic properties (high brix, good quality fruit and good fruit yield) are encompassed herein.

In one aspect the introgression fragment(s) is/are derived from the *C. colocynthis* donor of which a representative sample of seeds has been deposited under accession number NCIMB 42624 or of a descendant thereof.

Any of the five QTLs identified in the present invention can be transferred from a *C. colocynthis* donor to cultivated watermelon plants, alone or in different combinations. Comprising at least one dominant QTL, QTL7.1 and/or QTL9.1 is desirable. But the minor recessive QTLs, QTL1.1, QTL4.1 and/or QTL5.2 may also be useful, e.g. in lowering the virus titer in inoculated plants even further or making CGMMV virus undetectable by RT-qPCR and/or making plants and plant parts non-infectious and/or making the virus non-seed transmissible and/or conferring immunity. In one aspect, therefore, a cultivated watermelon plant is provided comprising QTL7.1 and/or QTL9.1 and further comprising one or more of QTL1.1, QTL4.1 and QTL5.2, preferably in homozygous form as they are recessive.

In one aspect the cultivated watermelon plants are diploid plants. In another aspect they are tetraploid plants. In yet a further aspect they are triploid plants, especially produced by pollinating a tetraploid inbred parent line (preferably comprising four copies of the introgression fragment(s) and SNP markers on the introgression fragments, e.g. four copies of QTL7.1 and/or QTL9.1) with pollen of a diploid inbred parent line (preferably comprising two copies of the introgression fragment(s), e.g. two copies of QTL7.1 and/or QTL9.1), to produce F1 triploid hybrid plants comprising three copies of the introgression fragment(s), e.g. three copies of QTL7.1 and/or QTL9.1.

When a SNP marker nucleotide, e.g. a donor nucleotide, is in diploid, triploid or tetraploid form, this can be detected in a genotyping assay, e.g. a KASP assay. So, for example a plant, plant part or plant cell (or DNA obtained therefrom) comprising two copies of an introgression fragment which comprises the donor nucleotide for SNP14 will have the genotype 'AA', while a plant, plant part or cell comprising three copies will have the genotype 'AAA' and a plant, plant part or cell comprising four copies will have the genotype 'AAAA'. Such SNP genotyping assays, for detecting whether a plant, plant part or plant cell comprises one or more of the CGMMV resistance QTLs of the invention, using one or more of the SNP markers provided herein, is also an aspect of the invention.

The cultivated watermelon plant, plant part or plant cell according to the invention preferably comprises an average CGMMV resistance of scale 3 (mild symptoms) or scale 4 (no symptoms).

In one aspect the cultivated watermelon plant or plant cell according to the invention is an inbred plant or plant cell, or an F1 hybrid plant or plant cell, or a diploid or tetraploid or triploid plant or plant cell. Also encompassed herein are seeds which grow into a plant of the invention as described herein.

Likewise, cultivated watermelon fruit or fruit parts comprising plant cells according to the invention are encompassed herein.

Also cultivated watermelon plant propagation material comprising a cultivated watermelon plant cell according to the invention is an embodiment.

Plant parts of plants according to the invention are also cuttings, scions, rootstocks, grafted seedlings or plants comprising a scion and/or rootstock of a plant according to the invention, leaves, fruits, parts of fruits, seeds, parts of seeds, cells, tissue cultures, flowers, pollen, embryos, roots, etc.

In one aspect a method for producing triploid hybrid cultivated watermelon seeds comprising the following steps is provided:
a) providing a first CGMMV resistant inbred diploid watermelon plant comprising two chromosomes 7, each having an introgression fragment from chromosome 7 of a CGMMV resistant donor plant of the species *Citrullus colocynthis*, the introgression fragment comprising QTL7.1 and the sequence of the donor plant for SNP14 (SEQ ID NO: 14), or in-between SNP13 and SNP18, or in-between SNP13 and SNP15; or the introgression fragment comprising QTL7.1 and the resistant donor nucleotide for one or more or all of SNP13, SNP14, SNP15, SNP16, SNP17, and SNP18;
b) providing a second CGMMV resistant inbred tetraploid watermelon plant comprising four chromosomes 7 each having an introgression fragment from chromosome 7 of a CGMMV resistant donor plant of the species *Citrullus colocynthis*, the introgression fragment comprising QTL7.1 and the sequence of the and the sequence of the donor plant for SNP14 (SEQ ID NO: 14), or in-between SNP13 and SNP18, or in-between SNP13 and SNP15; or the introgression fragment comprising QTL7.1 and the resistant donor genotype for one or more or all of SNP13, SNP14, SNP15, SNP16, SNP17, and SNP18;
c) allowing pollination of the tetraploid watermelon plant provided in step b) with pollen of the diploid watermelon plant provided in step a); and
d) collecting seeds from the fruits produced in step c).

Likewise a method for producing triploid hybrid cultivated watermelon seeds comprising the following steps is provided:
a) providing a first CGMMV resistant inbred diploid watermelon plant comprising two chromosomes 9, each having an introgression fragment from chromosome 9 of a CGMMV resistant donor plant of the species *Citrullus colocynthis*, the introgression fragment comprising QTL9.1 and the sequence of the donor plant for SNP22 (SEQ ID NO: 22), or in-between SNP19 and SNP24, or in-between SNP21 and SNP23; or the introgression fragment comprising QTL9.1 and the resistant donor genotype for one or more or all of SNP19, SNP20, SNP21, SNP22, SNP23 and SNP24;
b) providing a second CGMMV resistant inbred tetraploid watermelon plant comprising four chromosomes 9 each having an introgression fragment from chromosome 9 of a CGMMV resistant donor plant of the species *Citrullus colocynthis*, the introgression fragment comprising QTL9.1 and the sequence of the and the sequence of the donor plant for SNP22 (SEQ ID NO: 22), or in-between SNP19 and SNP24, or in-between SNP21 and SNP23; or the introgression fragment comprising QTL9.1 and the resistant donor genotype for one or more or all of SNP19, SNP20, SNP21, SNP22, SNP23 and SNP24;
c) allowing pollination of the tetraploid watermelon plant provided in step b) with pollen of the diploid watermelon plant provided in step a); and
d) collecting seeds from the fruits produced in step c).

The above two methods can also be used to generate triploid watermelon plants (and seeds from which such plants can grow) comprising three copies of QTL7.1 and three copies of QTL9.1. The plant under a) then comprises two copies of QTL7.1 and of QTL9.1 and the plant under b) comprises four copies of QTL7.1 and of QTL9.1.

The seeds collected in step d) are also an aspect of the invention, as are plants grown from these seeds and plant parts and cells of those plants. For example, triploid fruits, comprising three copies of QTL7.1 and/or of QTL9.1.

In one aspect the invention provides the use of one or more of markers SNP13, SNP14, SNP15, SNP16, SNP17, and SNP18 and/or one or more of markers SNP19, SNP20, SNP21, SNP22, SNP23 and SNP24 for identification of a CGMMV resistant watermelon plant or plant part or plant cell.

In another aspect the invention provides the use of one or more of markers SNP13, SNP14, SNP15, SNP16, SNP17, and SNP18 and/or one or more of markers SNP19, SNP20, SNP21, SNP22, SNP23 and SNP24 for introgression of CGMMV resistance into a CGMMV susceptible cultivated watermelon plant.

In a further aspect the invention provides the use of one or more of markers SNP1, SNP2, SNP3, SNP4, SNP5, and SNP6 and/or one or more of markers SNP7, SNP8 and SNP9 and/or one or more of markers SNP10, SNP11 and SNP12 for identification of a CGMMV resistant watermelon plant or plant part or plant cell.

In another aspect the invention provides the use of one or more of markers SNP1, SNP2, SNP3, SNP4, SNP5, and SNP6 and/or one or more of markers SNP7, SNP8 and SNP9 and/or one or more of markers SNP10, SNP11 and SNP12 introgression of CGMMV resistance into a CGMMV susceptible cultivated watermelon plant.

Also encompassed herein is a method of screening one or more *Citrullus* plants or plant parts, or DNA derived therefrom, for the presence of a CGMMV resistance conferring fragment on chromosome 7 and/or 9 comprising the steps of:
a) screening the genomic DNA for the SNP genotype of one or more or all of SNP13, SNP14, SNP15, SNP16, SNP17 and SNP18 and/or for one or more of SNP19, SNP20, SNP21, SNP22, SNP23 and SNP24; and optionally
b) selecting a plant or plant part which comprise the resistant donor nucleotide for one or more or all of SNP13, SNP14, SNP15, SNP16, SNP17 and SNP18 and/or for one or more or all of SNP19, SNP20, SNP21, SNP22, SNP23 and SNP24.

Also encompassed herein is a method of screening one or more *Citrullus* plants or plant parts, or DNA derived therefrom, for the presence of a CGMMV resistance conferring fragment on chromosome 1 and/or 4 and/or 5 comprising the steps of:
  a) screening the genomic DNA for the SNP genotype of one or more or all of SNP1, SNP2, SNP3, SNP4, SNP5, and SNP6 and/or for one or more of SNP7, SNP8, and SNP9 and/or for one or more of SNP10, SNP11 and SNP12; and optionally
  b) selecting a plant or plant part which comprise the resistant donor nucleotide for one or more or all of SNP1, SNP2, SNP3, SNP4, SNP5, and SNP6 and/or for one or more of SNP7, SNP8, and SNP9 and/or for one or more of SNP10, SNP11 and SNP12.

Obviously, the screening methods can be combined into one screening method to screen for the presence of a CGMMV resistance conferring fragment on chromosome 1, 4, 5, 7 and/or 9.

In one aspect the *Citrullus* plants or plant parts or DNA are *Citrullus colocynthis* plants or plant parts or DNA, such as PI accessions of seedbanks, which potentially comprise one or more of the QTLs as described herein. For examples the PI accessions of the USDA GRIN seedbank, e.g. mentioned above, can be screened in this way. Optionally the plant can be tested for CGMMV resistance, e.g. as described elsewhere herein and in the Examples. This can be done before SNP marker screening (e.g. to start only with plants having a score of 3 or 4 in the CGMMV assay), and/or after the marker screening, e.g. after step b), in order to verify that the selected plant or plant part has CGMMV resistance.

In another aspect the *Citrullus* plants, plant parts or DNA are *Citrullus lanatus* ssp. *vulgaris*, e.g. varieties, inbred lines, breeding lines, diploids, triploids, tetraploids, etc. which are screened to check whether they comprise one or more introgression fragments and/or heterozygosity or homozygosity or number of recombinant chromosomes comprising the introgression fragment(s).

The plant part may be any part comprising cells of the plant (or DNA derived therefrom), e.g. leaf or part of a leaf, seed, seed coat, embryo, pollen, flowers, ovules, roots, stems, fruit, part of fruits, cells, etc. The plant part screened for the SNP marker genotype may also be the seed coat, as the seed coat is maternal DNA. So when the seed coat of a F1 hybrid is screened, and compared to the genotype of the F1 hybrid itself, the genotype of the male parent line can be inferred. Thus, the presence of one or more introgression fragments according to the invention in the parent lines of a hybrid can be determined. Marker screening can be carried out using various methods, such as SNP genotyping assays (e.g. KASP assays, TaqMan assays, a High Resolution Melting (HRM) assays, SNP-genotyping arrays such as e.g. Fluidigm, Illumina, etc., or DNA sequencing may equally be used.

For example SNP markers can be detected using a KASP-assay (see \Vww.kpbioscience.co.uk) or other assays. A KASP-assay can be developed for the SNPs described herein. For developing KASP-assays for the SNPs two allele specific forward primers and one allele specific reverse primer were designed according to common general knowledge (see e.g. Allen et al. 2011, Plant Biotechnology J. 9, 1 0 86-1 099, especially p097-098 for KASP assay method).

Also provided is a method of growing any of the cultivated watermelon plants of the invention in an area where CGMMV occurs.

Further, a method of selecting a cultivated watermelon plant comprising an introgression fragment from a *C. colo-cynthis* donor as described (e.g. comprising QTL7 and or QTL9) is provided, said method comprising the steps:
  a) Providing a population of watermelon plants derived from a cross between a (e.g. CGMMV susceptible) watermelon plant and a CGMMV resistant *C. colocynthis* plant, such as a plant of NCIMB 42624 or progeny thereof (e.g. obtained by selfing) or a CGMMV resistant watermelon plant, such as a line or variety comprising one or more introgression fragments from a CGMMV resistant *C. colocynthis* plant (comprising e.g. QTL7.1 and/or QTL9.1),
  b) selecting a plant from that population which comprises one or more introgression fragment from the *C. colocynthis* donor, which introgression fragment comprises a QTL selected from QTL1.1, QTL4.1, QTL5.2, QTL7.1 and/or QTL9.1 as described herein.

The population of plants may be e.g. an F2 or F3 population or a backcross population, an inbred population (e.g. Recombinant inbred lines), or any other population comprising one or more recombinant chromosomes, i.e. chromosomes comprising fragments of the *C. colocynthis* donor, especially a recombinant chromosome comprising 1 comprising QTL1.1, and/or a recombinant chromosome 4 comprising QTL4.1, and/or a recombinant chromosome 5 comprising QTL5.2, and/or a recombinant chromosome 7 comprising QTL7.1 and/or a recombinant chromosome 9 comprising QTL9.1.

Selection can be done by any method described herein, e.g. SNP genotyping for one or more of the SNP markers linked to the QTLs, sequencing, CGMMV resistance testing, etc.

The selected plant comprises at least one of the QTLs of the invention and is also an embodiment of the invention.

Non-genetically engineered *Citrullus* plant cells or plants (e.g. diploid, triploid or tetraploid, or another ploidy), and seeds from which any of the herein described plants can be grown, obtainable, obtained, derivable or derived, identified or selected by any of the methods described above are also an embodiment of the invention.

Also plant parts, such as scions, shoots, leaves, flowers, cuttings, roots, fruits, fruit parts, pollen, ovules and seeds, obtainable by or obtained, derivable or derived from plants according to the invention are an embodiment of the invention.

Production and cultivation of seedless watermelon plants has become popular and is known to those skilled in the art. Normal watermelon plants are diploid (2n). Seedless fruit producing watermelons are produced by crossing a male diploid (2n) watermelon plant with a female tetraploid (4n) watermelon plant. The resulting F1 seeds are triploid (3n) and can be grown into triploid (3n) F1 plants. Induction of fruit setting in the F1 plants requires pollination. As the triploid (3n) F1 plants do not produce fertile pollen, so called polliniser plants have to be planted in the same field. The polliniser plants are diploid (2n). Generally a ratio of polliniser to triploid (3n) plants of around 1 to 3 must be planted in a given scheme for providing sufficient pollen for pollinating. The cross-pollination between the diploid (2n) polliniser and the flowers of the female triploid (3n) plant induces fruit set and leads to the production of seedless triploid (3n) fruits on the triploid F1 plant. The diploid (2n) and tetraploid (4n) parents of the F1 plants each produce seed bearing fruits and can both be propagated independently from each other by self-pollination.

Specialised pollinisers have been produced which are usually compact plants (so as not to compete with triploids), producing small inedible and/or unmarketable fruits with a rind pattern that can easily be distinguished from the triploid (3n) fruit during harvesting. The choice of using edible and/or marketable dual purpose polliniseres or inedible and/or unmarketable specialised polliniseres depends on whether the grower has a market or use for the seeded fruits produced by the respective polliniser. The choice of polliniser affects yield. (McGregor & Waters, 2014, HortScience 49(6), 714-721).

Some polliniseres produce diploid fruits which are marketable, while others produce fruits that are unsuitable for consumption and/or marketing. Polliniseres producing marketable fruits are designated "dual purpose polliniseres". Polliniseres producing inedible and unmarketable fruits which is easily distinguishable from the seedless fruits are designated "specialised polliniseres".

In a further embodiment of the invention, the non-genetically engineered *Citrullus* plants according to the invention are polliniser plants or the *Citrullus* plants according to the invention are used as polliniser plant grown in a field. Preferably, the polliniser plant according to the invention is diploid (2n). The polliniser plant according to the invention can be a specialised polliniser plant or a dual purpose polliniser plant.

The term "polliniser plant" is used herein for a plant providing pollen for fertilisation of another plant, not producing sufficient viable pollen by itself.

Non-genetically engineered *Citrullus* plants comprising non-genetically engineered *Citrullus* plant cells according to the invention are another embodiment of the invention.

In one aspect the CGMMV resistant plants are hybrids, e.g. single cross hybrids (F1 hybrids) produced by crossing two inbred parent lines with each other. The hybrid, e.g. the F1 hybrid, may be homozygous or heterozygous for the CGMMV resistance QTL or QTLs. In a further aspect the plants comprising the CGMMV resistance QTL or QTLs are inbred lines.

Also seeds from which any of the described plants can be grown are an embodiment of the invention. Furthermore, the invention concerns plant parts obtainable by, derivable by, obtained, derived or originating from non-genetically engineered *Citrullus* plants according to the invention. Preferably, the plant parts according to the invention comprise non-genetically engineered *Citrullus* plant cells according to the invention.

The term "plant part" as used herein shall mean any piece or section of a plant including fruits, fruit parts, rootstocks, scions, cuttings, pollen, anthers, ovules, embryos, roots, stems, leaves, cotyledons, hypocotyls, flowers, callus, in vitro cell or tissue cultures comprising plant material, plant in vitro propagation material, etc. The plant part can be eligible to be regenerated into a whole plant (regenerable plant part) or it can be a part not eligible to be regenerated into a whole plant (non-regenerable plant part). Such a non-regenerable plant part may be part of the whole plant or part of the seed from which the plant can be grown. The CGMMV resistance QTL or QTLs and/or introgression fragment(s) comprising the resistance QTL(s), is/are present and detectable in such a plant part, e.g. by marker analysis (e.g. using one or more of the SNP markers described herein), sequence analysis, chromosome painting, etc.

Preferred plant parts according to the invention are seeds or fruits. Preferably, the seeds or fruits according to the invention comprise non-genetically engineered *Citrullus* plant cells according to the invention.

Another embodiment concerns fruits according to the invention which are seedless fruits. Likewise, *Citrullus* plants according to the invention producing seedless fruits are an embodiment of the invention. The term "fruit" in its botanical meaning is commonly understood to be a seed bearing structure developed from the ovary of angiosperm flowers.

A "seedless fruit" as commonly used in the art and in particular in breeding, although being somehow contradicting the botanical meaning of "fruit", is to be understood in context with the present invention to be a fruit without mature or viable seeds. Mature or viable seeds can be germinated in soil under conditions appropriate for the respective plant and grown into plants. This test can be used to determine if a plant produces seedless fruits. Seedless fruits will not produce seed which will germinate and grow into a plant under conditions appropriate for the respective plant.

A further specific embodiment according to the invention concerns plant propagation material of plants described herein or concerns propagation material comprising non-genetically engineered plant cells according to the invention, or propagation material of plants obtainable/obtained by a method according to the invention for production of a CGMMV resistant *Citrullus* plant. One embodiment of the invention is propagation material of plants comprising one or more of the QTLs as described herein. Also comprised by the invention is propagation material of CGMMV resistant plants obtained/obtainable from plants originating from a crossing with a plant obtained from seeds of deposit accession number NCIMB 42624 with another plant. Preferably the propagation material obtained/obtainable from a crossing with plants obtained from seeds of deposit accession number NCIMB 42624 comprises non-genetically engineered plant cells according to the invention. In one aspect the invention relates to propagation material of CGMMV resistant plants, said plants comprise a CGMMV resistance QTL or QTLs obtained/obtainable from, or as present in, seeds of deposit accession number NCIMB 42624 or CGMMV resistant progeny thereof.

Here, the term "propagation material" comprises those components of the plant which are suitable for generating progeny via the vegetative (agamic) or generative (gamic, sexual) route. Suitable for vegetative propagation are, for example, cuttings, in vitro tissue, cell, protoplast, embryo or callus cultures or micropropagation methods. Other propagation material includes, for example, fruits, seeds, seedling, being resistant to CGMMV etc. The propagation material in one aspect takes the form of cuttings which are propagated by grafting to another rootstock or in vitro tissue culture material, in particular embryo cultures. In particular preferred is propagation material in the form of in vitro tissue culture material, particularly in vitro embryo cultures. It is understood that the propagating material comprises the CGMMV resistance QTL or QTLs as described.

Grafting is used more and more in the vegetable industry for production of seedlings which after transplanting are grown by farmers. Indeed, this technique improves the quality of final plants by combining the features of the rootstock, such as abiotic stress resistance, disease resistance and vigour, with the features of the scion producing high quality fruits.

Grafting watermelons has a number of advantages, as is explained in Davis et al. (2008, Critical Reviews in Plant Sciences Vol. 27, "Cucurbit Grafting", page 50-74). Apart from providing resistance against fungi and viruses, the use of grafting can also increase tolerance against different abiotic stresses such as cold/low temperature, drought, salinity, flooding/water and can have beneficial effects on e.g. growth, yield, nutrient uptake, plant vigour, fruit size and fruit quality.

The main advantage of grafting with respect to the present invention is that rootstocks or scions can be used which provide or enhance resistance against soil born diseases, especially when genetic or chemical approaches for disease management are not available or not sufficient, as is the case currently with infections by CGMMV in watermelon. Thus, CGMMV resistant rootstocks or scions can be used in graftings, e.g. with CGMMV susceptible scions or rootstocks, before transplanting. CGMMV susceptible watermelon scions can e.g. be grafted onto CGMMV resistant rootstocks for watermelon production or CGMMV resistant scions can be grafted onto CGMMV susceptible rootstocks. It was found that a CGMMV resistant scion, when grafted onto a CGMMV virus infected susceptible rootstock, remains free of CGMMV symptoms (the scion has a CGMMV score of 4), i.e. keeps having a CGMMV resistant in phenotype.

Park et al. (2005, Plant Cell Rep 24, 350) disclose production of transgenic CGMMV resistant watermelon plants from the wild cultivar *Citrullus lanatus* subspecies gongdae by introducing a recombinant nucleic acid conferring expression of a CGMMV coat protein in the transgenic plant. Park suggests the use of the transgenic plants for producing rootstocks onto which scions from *Citrullus* crop plants can grafted for combating CGMMV induced yield loss.

In the present invention, it has been surprisingly found, that grafting a CGMMV resistant *Citrullus* scion onto a *Citrullus* rootstock infected with and susceptible to CGMMV does enable the growth of *Citrullus* plants being free of CGMMV caused symptoms. An advantage of the present application is that grafted *Citrullus* seedlings, comprising a rootstock and/or a scion being resistant to CGMMV can be grown into symptom free plants. Thus, it is possible to grow such plants even in areas in which the soil is contaminated with CGMMV without losses in quality and yield of fruits. Thus, using a CGMMV resistant scion according to the invention, especially a cultivated watermelon scion comprising one or more of the QTLs described herein, combined with a rootstock which may be a CGMMV susceptible rootstock, enables the scion to remain free of CGMMV symptoms.

Further preferred plant parts according to the invention therefore are rootstocks and/or scions. Preferably, the rootstocks and/or scions according to the invention comprise non-genetically engineered *Citrullus* plant cells according to the invention. The rootstock and/or scion comprises one or more (or all) of the QTLs described herein, detectable by e.g. the SNP markers linked to the QTLs.

In one aspect the rootstock and/or the scion is a CGMMV resistant *Citrullus* rootstock or scion, especially a *C. colocynthis* rootstock or scion according to the invention comprising one or more of the herein described QTLs, e.g. NCIMB 42624 or descendants thereof. Bigdelo et al. 2017 (Australian Journal of Crop Science, AJCS, 11(06):727-732) describe the advantages of using a *C. colocynthis* rootstock with cultivated watermelon scions.

In another aspect the rootstock and/or the scion is a CGMMV resistant cultivated watermelon rootstock according to the invention comprising one or more of the herein described QTLs, e.g. obtainable from seed deposited under accession number NCIMB 42624 or descendants thereof by e.g. (back)crossing such plants or descendants with cultivated watermelon and selecting progeny comprising one or more QTLs from a CGMMV resistant *C. colocynthis* donor.

"Rootstock" with respect to be used in the technical field of plant grafting refers herein to a detached plant part or stem onto which a graft is made. Typically the rootstock represents the bottom portion, including the roots and the lower stem part of a grafted plant. At the time of or directly after grafting, it is not necessary in any event that roots are present at the rootstock, because in respective cases roots will regrow from the rootstock stem in case they have been removed before.

A "scion" refers to a detached living part of a plant (such as a shoot or branch) supplying solely aerial parts to a grafted plant.

See also US 2013/0298273 A1, incorporated herein by reference, for watermelon grafting methods, both single grafts and double grafts.

In a preferred embodiment of the invention the rootstock according to the invention and/or the scion according to the invention is a rootstock or a scion, respectively, of a cultivated watermelon plant comprising one or more QTLs originating from, obtained from or obtainable by using a CGMMV resistant *Citrullus colocynthis* plant, e.g. a plant grown from seeds deposited under accession Number NCIMB 42624 or progeny thereof, as donor of the introgression fragment(s) comprising one or more of the QTL(s), e.g. QTL7.1 and/or QTL9.1.

In another aspect the rootstock according to the invention and/or the scion according to the invention is a rootstock or a scion, respectively, obtainable by or obtained, derived, derivable or originating from a plant grown from seeds deposited under accession Number NCIMB 42624 or progeny thereof.

A further embodiment of the present invention concerns a grafted plant comprising at least one rootstock and at least one scion, wherein at least one rootstock of the grafted plant is a rootstock according to the invention or at least one scion of the grafted plant is a scion according to the invention and/or at least one rootstock of the grafted plant comprises non-genetically engineered *Citrullus* plant cells according to the invention or at least one scion of the grafted plant comprises non-genetically engineered *Citrullus* plant cells according to the invention.

A preferred embodiment of the invention concerns a grafted plant according to the invention wherein at least one scion of the grafted plant is a scion according to the invention and/or at least one scion of the grafted plant comprises non-genetically engineered *Citrullus* plant cells according to the invention. Thus, in one aspect the scion is of a CGMMV resistant plant of the invention, especially a cultivated watermelon scion comprising one or more of the QTLs. The rootstock may be a CGMMV susceptible rootstock, e.g. It may also be a CGMMV resistant rootstock. Likewise it may be any commonly known rootstock, such as *Lagenaria* or *Cucurbita* rootstocks or others described herein and known in the art. Alternatively two scions may be grafted onto a single rootstock, so in one aspect at least one of the two scions, optionally both scions are scions of a CGMMV resistant plant of the invention, especially cultivated watermelon.

In another embodiment the grafted plant according to the invention comprises at least one rootstock which is a rootstock according to the invention and/or at least one rootstock of the grafted plant comprises non-genetically engineered *Citrullus* plant cells according to the invention.

In a further embodiment, the grafted plant according to the invention is a seedling or a grafted seedling. In connection with the present invention the term "grafted plant" refers to a plant appearing to grow or growing as a single plant, which plant however is composed of different plant parts, wherein the plant parts originate from plants having different genotypes. Commonly the different plant parts are designated rootstock and scion.

"Grafting" refers to the method of joining together different plant parts having different genotypes so that those different plant parts appear to grow or grow as a single plant.

"Seedling" herein refers to a young plant especially one that develops from an embryo of a seed. "Grafted seedling" herein refers to a young plant which consists of parts of different seedlings having a different genotype. Commonly the different parts are designated rootstock and scion.

It is well known in the art that a grafted plant or seedling may consist of more than two parts of different plants. Grafted plants can be e.g. composed of more than a single rootstock. The method used for producing such kind of plants is commonly known in the art and designated "multi-rootstock grafting" in contrast to single rootstock-grafting. Grafted watermelon plants or methods for producing grafted watermelon plants having one ("single-rootstock grafting"), two ("dual-rootstock grafting") or three ("threefold-rootstock grafting") rootstocks, are known in the art and have been described e.g. in (Qin et al., 2014, Not Bot Agrobo 42(2), 495-500).

A further embodiment of the invention therefore concerns a grafted plant according to the invention or a grafted seedling according to the invention comprising one, two or three rootstocks. More preferably, the grafted plant according to the invention or the grafted seedling according to the invention comprises two rootstocks, even more preferred, one rootstock.

It is common to graft *Citrullus* scions to *Citrullus* rootstocks. In the majority of cases of watermelon grafting rootstocks from other Cucurbit plants, in particular to mention the genera *Lagenaria, Cucurbita* and interspecific *Cucurbita* hybrids, are used. Watermelon plants are grafted onto rootstocks from other Cucurbit plants e.g. to control *Fusarium* wilt, to increase low temperature tolerance and to increase yield by enhancing water and plant nutrients uptake. Rootstocks that are commonly used for grafting watermelon are *Cucurbita moschata* (pumpkin), *Cucurbita maxima* (squash), *Benincasa hispida* (winter melon), *Lagenaria siceraria* (bottle gourd) as well as hybrids of the above-mentioned species, e.g. *Cucurbita maxima* x *Cucurbita moschata* (Yetisir & Sari, 2003, Austarlian J. Experimental Agriculture 43, 1269-1274).

In grafted watermelon plants rootstocks from *Lagenaria siceraria, Benincasa hispida, Cucurbita moschata, Cucurbita pepo* and hybrids of *Cucurbita maxima* x *Cucurbita moschata* are used for e.g. *Fusarium* wilt control and *Sicyos angulatus* rootstocks are used e.g. for nematode control. Hybrids of *Cucurbita maxima* x *Cucurbita moschata, Cucurbita moschata* or *Cucurbita pepo* rootstocks are used additionally in watermelon grafting for increasing resistance to low temperatures (Singh & Rao, 2014, Agri. Reviews 35(1), 24-33).

Using a scion according to the invention grafted to a respective rootstock now enables the control of CGMMV infection in *Citrullus* crop plants in addition to other biotic stresses or abiotic stresses. This can be achieved by grafting a scion according to the invention to a respective rootstock which can be selected according to the respective needs in the cultivation area, like controlling specific biotic (e.g *Fusarium* or nematode infection) and/or abiotic (e.g. low temperature) stresses.

Therefore, a further embodiment of the invention concerns a grafted plant according to the invention or a grafted seedling according to the invention, wherein at least one rootstock is from a *Citrullus* plant or from a plant of a different genus, preferably the rootstock from a plant of a different genus is selected from the group consisting of a plant of the genus *Cucurbita, Lagenaria, Sicyos* or *Benincasa* or a hybrid between plants from these genera. In a more preferred embodiment the grafted plant according to the invention or the grafted seedling according to the invention comprises at least one rootstock from a *Citrullus lanatus* plant, *Cucurbita moschata* plant, *Cucurbita maxima* plant, *Cucurbita pepo* plant, *Benincasa hispida* plant, *Lagenaria siceraria* plant, *Sicyos angulatus* plant or a hybrid plant of *Cucurbita maxima* x *Cucurbita moschata.*

In one embodiment of the invention the grafted plant according to the invention or the grafted seedling according to the invention comprises a scion according to the invention and comprises a rootstock obtained from plants selected from the group consisting of a *Lagenaria* plant, *Citrullus lanatus* plant, *Cucurbita moschata* plant, *Cucurbita maxima* plant or a hybrid plant of *Cucurbita maxima* x *Cucurbita moschata*, even more preferably the rootstock is obtained from plants selected from *Citrullus lanatus* or a hybrid plant of *Cucurbita maxima* x *Cucurbita moschata.*

A preferred *Cucurbita maxima* x *Cucurbita moschata* hybrid in connection with the present invention is *Cucurbita maxima* x *Cucurbita moschata* cultivar Ercole (Nunhems; commercially available). Other preferred rootstocks are Shintosa, e.g. Shintosa Camelforce (Nunhems; commercially available) or *Lagenaria* rootstocks, e.g. *Lagenaria* hybrid rootstock Colosso (Nunhems; commercially available). Like for rootstocks, it is also established in the art that a grafted plant can have more than one scion. Double grafted or "double-scion grafted" watermelon plants comprising two scions grafted to a rootstock have been described e.g. in WO2012062672 A1 and US 20130298273. US 20130298273 discloses watermelon plants having two scions grafted to a rootstock wherein the scions can either be from genetically identical plants or from genetically different plants. The scions may be diploid (2n) or triploid (3n). Concerning the scions obtained from genetically different plants, one scion grafted to the rootstock may be diploid (2n) and the other scion grafted to the same rootstock may be triploid (3n). Such a combination of a diploid (2n) and a triploid (3n) scion grafted to the same rootstock may be used for producing seedless fruits (see herein above) and the diploid scion under these circumstances may be a specialised polliniser or dual purpose polliniser.

Therefore, a further embodiment of the invention concerns a grafted plant according to the invention or a grafted seedling according to the invention, wherein the grafted plant or seedling comprises at least two scions, wherein at least one scion is a scion according to the invention and/or at least one scion comprises non-genetically engineered *Citrullus* plant cells according to the invention. In a preferred embodiment the grafted plant according to the invention or the grafted seedling according to the invention comprises two scions according to the invention and/or each of the two scions comprises non-genetically engineered *Citrullus* plant cells according to the invention. In one further embodiment the two scions according to the invention have an identical (the same) genotype and/or the two scions comprise non-genetically engineered *Citrullus* plant cells according to the invention having an identical (the same) genotype. In another embodiment the two scions according to the invention have a different genotype and/or the two scions comprise non-genetically engineered *Citrullus* plant cells according to the invention having a genotype different from each other, preferably one scion is diploid (2n) and the other scion is triploid (3n). In respect to grafted plants according to the invention or grafted seedlings according to the invention where one scion is diploid (2n) and the other scion is triploid (3n) the diploid (2n) scion may be a specialised polliniser or a dual purpose polliniser.

In one specific embodiment the grafted plant according to the invention comprises at least one rootstock according to the invention and at least one scion according to the invention. Preferably, the grafted plant according to the invention comprises one rootstock according to the invention and at least one scion according to the invention or the grafted plant according to the invention comprises at least one rootstock according to the invention and one scion according to the invention. More preferably, the grafted plant according to the invention comprises one rootstock according to the invention and one scion according to the invention.

Methods for production of grafted plants, including watermelon are common in the art. Manual (hand work) grafting and machine (robotic) grafting methods have been established. Various grafting techniques are known for watermelon, including the "tongue approach grafting", "hole insertion grafting", "one cotyledon grafting" and "side grafting". (Hassell et al., 2008, HortScience 43(6), 1677). Grafting methods in vegetables, including watermelon are also reviewed in Singh & Rao (2014, Agri. Reviews 35(1), 24-33).

As discussed herein above, the provision of CGMMV resistant *Citrullus* plants now enables production of further *Citrullus* crop plants being resistant to CGMMV.

A further aspect of the invention therefore concerns a method for production of a CGMMV resistant *Citrullus* plant comprising the following steps:
 a) crossing a CGMMV resistant *Citrullus* plant (donor) with another *Citrullus* plant (recipient), e.g. a CGMMV susceptible plant, or providing progeny of such a cross, and
 b) obtaining seeds from the crossed plants according step a), or selecting seeds/plants comprising CGMMV resistance.

The method may optionally further comprise selfing and/or backcrossing (e.g. to the other *Citrullus* plant in step a), e.g. to a susceptible cultivated watermelon line or variety) a plant grown from the seeds in step b) one or more times, and selecting a selfing descendant and/or a backcross descendant comprising the CGMMV resistance (e.g. one or more of the QTLs).

The CGMMV resistant donor plant may be selected phenotypically and/or genotypically using one or more of the SNP markers linked to the QTLs described herein. So for example the donor may comprise one or more or all of QTL1.1, QTL4.1, QTL5.2, QTL7.1 and QTL9.1. The donor may be e.g. a *C. colocynthis* donor (optionally selfed one or more times) or a *Citrullus lanatus* ssp. *vulgaris* donor into which already one or more of the QTLs has been introgressed and which are transferred in this method into another CGMMV susceptible plant.

The selection of a donor and/or of a descendant comprising the CGMMV resistance derived from the donor can be done as described herein, e.g. phenotypically, e.g. using mechanical leaf inoculation to determine the resistance phenotype and/or detecting CGMMV virus levels using RT-qPCR, and/or other assays for detecting CGMMV virus such as ELISA or dot-blots, and/or quick assays for detecting CGMMV symptoms such as dipping roots into virus solutions or soaking seeds in virus solution, etc., and/or genotypically using one or more molecular markers linked to the QTLs as described herein. So, for example the donor can be tested for CGMMV resistance and/or for e.g. the CGMMV resistance donor genotype for one or more of SNP1, SNP2, SNP3, SNP4, SNP5 and/or SNP6 linked to QTL1.1; and/or one or more of SNP7, SNP8 and/or SNP9 linked to QTL4.1; and/or one or more of SNP10, SNP11 and/or SNP12 linked to QTL5.2; and/or one or more of SNP13, SNP14, SNP15, SNP16, SNP17 and/or SNP18 linked to QTL7.1; and/or one or more of SNP19, SNP20, SNP21, SNP22, SNP23 and/or SNP24 linked to QTL9.1, all as described elsewhere herein.

The CGMMV resistant plant in step a) in the method according to the invention for production of a *Citrullus* plant can be any *Citrullus* plant as long as it is resistant to CGMMV. Preferably the *Citrullus* plant provided in step a) is a *Citrullus* plant having a diploid (2n) chromosome number of 22 and/or is crossable with a *Citrullus* crop plant. More preferably, the CGMMV resistant plant in step a) is a non-genetically engineered plant according to the invention, more preferably it is a plant of the species *Citrullus colocynthis*, even more preferred it is a plant grown from seeds deposited under accession number NCIMB 42624. In another aspect it is a cultivated watermelon plant as described, e.g. comprising one or more or all of the CGMMV resistance QTLs introgressed from a *C. colocynthis* donor, e.g. one or more of the QTLs as obtained/obtainable from seeds deposited under NCIMB 42624 or CGMMV resistant progeny thereof.

The method above may therefore optionally comprise a step of analyzing the DNA for one or more markers linked to any one or more of the QTLs in order to optionally select a donor and/or a descendant comprising one or more of the QTLs. In one aspect QTL7.1 and/or QTL9.1 are present in the donor and are transferred to the descendants of the cross. If the donor is an elite line or variety of cultivated watermelon already comprising an introgression fragment (comprising a QTL), then it is simply a matter of selecting progeny which retain the recombinant chromosome comprising the introgression fragment. This can simply be done by phenotypic testing and/or genotyping using one or more of the SNP markers, e.g. in a KASP assay or other genotyping assay. Obviously also other methods such as sequencing may be used to determine if the sequences comprising the donor nucleotides are present. Crossing is a process common for a person skilled in the art. The other *Citrullus* plant in step a) in the method according to the invention for production of a *Citrullus* plant preferably is a *Citrullus lanatus, Citrullus colocynthis* or *Citrullus naudinianus* plant, more preferably the plant is a *Citrullus lanatus* plant, most preferred it is a *Citrullus lanatus* subspecies *vulgaris* plant. In one aspect it is a CGMMV susceptible cultivated watermelon line or variety.

Assays for detection of CGMMV encoded proteins in plant tissue are commercially available, e.g. an ELISA Reagent Set for CGMMV detection or an CGMMV ImmunoStrip test both are on sale by Agdia, Inc., 52642 County Road 1, Elkhart, Ind. 46514. Those tests are suitable in detecting CGMMV proteins in infected plants and thus may also be used for showing the absence of virus protein in plants which had been previously inoculated.

CGMMV RNA can be detected in plant material by various methods, e.g. by PCR based analysis as described herein under General Methods. A highly sensitive real time reverse-Transcription PCR test for CGMMV has been described by Hongyun et al. (2008, J Virological Methods 149, 326-329). A preferred phenotypic test for identifying CGMMV resistant plants is testing on the basis of visually evaluated symptoms described herein under General Methods, but clearly other tests exist, such as field tests involving appropriate susceptible controls.

In a another embodiment the method according to the invention for production of a *Citrullus* plant comprises a further step which is producing further Critrullus plants by using the CGMMV resistant *Citrullus* plant identified. The production of further plants from a given plant is well established is in the art. The further plants produced are characterized in that they are resistant to CGMMV. These further plants can be produced by means of vegetative (agamic) or generative (gamic, sexual) reproduction or by crossings with other *Citrullus* plants. Suitable for vegetative propagation are, for example, cuttings, in vitro tissue, cell, protoplast, embryo or callus cultures, micropropagation, rhizomes or tubers. Other propagation material includes, for example, fruits, seeds, seedlings, being heterozygous or homozygous for a chromosomal fragments conferring resistance to CGMMV.

Techniques for vegetative (agamic) propagation, including micropropagation of plants are well known in the art and e.g. described for banana, citrus, mango, papaya, avocado, (sweet) melon, have been described in Pua and Davey (2007, Springer Science & Business Media, ISBN: 3540491619, 9783540491613). Sultana and Rhaman (2012, LAP Lambert Academic Publishing, ISBN-13: 978-3-8484-3937-9) e.g. disclose various tissue culture and micropropagation methods for watermelon.

In one embodiment the method according to the invention for production of a *Citrullus* plant is a method for production of a non-genetically engineered *Citrullus* plant according to the invention.

Plants obtainable/obtained by a method according to the invention for production of a *Citrullus* plant are also an embodiment of the invention.

As discussed herein above, the CGMMV resistant plants disclosed herein are also suitable for producing CGMMV resistant grafted plants.

A further embodiment of the invention therefore concerns a first method for producing a grafted plant or a grafted seedling comprising the following steps:
  a) providing a rootstock selected from plants of the group of the genera *Citrullus, Curcubita, Lagenaria, Sicyos* or *Benincasa* or a hybrid produced by crossing of two species of any of these genera,
  b) providing a scion according to the invention,
  c) grafting the scion according to step b) to the rootstock according to step a).

It has been described herein above that it is common in the art to use rootstocks from various genera for grafting of *Citrullus* plants. Concerning step a) of the first method according to the invention for producing a grafted plant or a grafted seedling the rootstock can therefore be obtained from the genera indicated in step a). The hybrid mentioned in step a) of the first method according to the invention for producing a grafted plant or a grafted seedling can be any hybrid obtained by crossing of two different species selected from the indicated genera. The hybrid therefore can be obtained by crossing two different species of the same genus or by crossing of two different species from different genera.

Preferably the rootstock according to step a) is selected from the group of species consisting of *Citrullus lanatus, Cucurbita moschata, Cucurbita maxima, Cucurbita pepo, Benincasa hispida, Lagenaria siceraria, Sicyos angulatus* or a hybrid plant produced by crossing of two *Cucurbita* species.

Examples for specific rootstocks are Nunhems rootstock varieties Macis F1 (species *Lagenaria siceraria*), Nun 3001 RT F1 (species *Lagenaria siceraria*), Shintosa Camelforce F1 (interspecific *Cucurbita* hybrid), Ercole F1 (interspecific *Cucurbita* hybrid); or from Syngenta's rootstock varieties Emphasis (Langenaria type rootstock) and Strong Tosa (Interspecific squash hybrid); or from other watermelon compatible rootstocks.

In one specific embodiment, concerning step a) of the method according to the invention for producing a grafted plant or grafted seedling the rootstock is a rootstock according to the invention and/or the rootstock comprises non-genetically engineered *Citrullus* plant cells according to the invention.

The scion according to step b) of the first method according to the invention for producing a grafted plant or grafted seedling can be any scion which has been described herein as embodiment of a scion according to the invention. Preferably the scion according to step b) is obtained from a non-genetically engineered *Citrullus* plant according to the invention, more preferably the scion is obtained from a non-genetically engineered *Citrullus lanatus* plant according to the invention, most preferably from a non-genetically engineered *Citrullus lanatus* subspecies *vulgaris* plant according to the invention.

A further embodiment of the invention concerns a second method for producing a grafted plant or a grafted seedling comprising the following steps:
  a) providing a rootstock according to the invention,
  b) providing a scion of a *Citrullus* plant,
  c) grafting the seedling according to step b) to the rootstock according to step a).

The rootstock according to step a) of the second method according to the invention for producing a grafted plant or grafted seedling can be any rootstock which has been described herein as embodiment of a rootstock according to the invention. Preferably the rootstock according to step a) is obtained from a non-genetically engineered *Citrullus* plant according to the invention, more preferably the rootstock is obtained from a non-genetically engineered *Citrullus colocynthis* or *Citrullus lanatus* (including *Citrullus lanatus* subspecies *vulgaris*) plant according to the invention. In one aspect NUN 42624 or a CGMMV resistant descendant thereof is used as roostock in step a).

The scion according to step b) of the second method according to the invention for producing a grafted plant or grafted seedling can be a scion of any species selected from *Citrullus lanatus, Citrullus colocynthis* or *Citrullus naudinianus*. Preferably the scion is a scion of a *Citrullus lanatus* plant, even more preferably the scion is a scion of a *Citrullus lanatus* subspecies *vulgaris* plant. In one aspect the scion is a cultivated watermelon scion, of a CGMMV resistant plant according to the invention comprising one or more of the QTLs described.

In one specific embodiment, concerning step b) of the second method according to the invention for producing a grafted plant or grafted seedling the scion is a scion according to the invention and/or the scion comprises non-genetically engineered *Citrullus* plant cells according to the invention.

Well known grafting methods have been discussed herein and are applicable here accordingly in respect with step c) of the first and second method according to the invention for producing a grafted plant or grafted seedling. Optionally, depending on the grafting method used, after merging rootstock and scion for preventing the graft from drying out and supporting healing, the merged area between rootstock and scion may be covered with a seal (e.g. aluminium) and/or a grafting clip or a silicone sleeve may be used for keeping rootstock and scion together.

Optionally, the first or second method according to the invention for producing a grafted plant or grafted seedling comprise a further step d), wherein the grafts obtained in step c) are placed in a healing room or a humidity chamber. Preferably the grafts are kept in the healing room or humidity chamber until the healing process is complete. After the healing process is completed, plants are put into a greenhouse for acclimatization, before they are transplanted.

In one specific embodiment of the invention, the rootstock according step a) and the scion according to step b) of the first or second method according to the invention for producing a grafted plant or grafted seedling can be any rootstock or any scion which has been described herein as embodiment of a rootstock or a scion, respectively, according to the invention. Preferably the scion according to step b) is obtained from a non-genetically engineered *Citrullus* plant according to the invention, more preferably the rootstock according to step a) is a rootstock from a non-genetically engineered *Citrullus colocynthis* or a *Citrullus lanatus* plant according to the invention most preferably from a *Citrullus lanatus* subspecies *vulgaris* plant according to the invention. Preferably the scion according to step b) is obtained from a non-genetically engineered *Citrullus* plant according to the invention, more preferably the scion is obtained from a non-genetically engineered *Citrullus lanatus* plant according to the invention, most preferably from a non-genetically engineered *Citrullus lanatus* subspecies *vulgaris* plant according to the invention.

In one embodiment the first or second method according to the invention for producing a grafted plant or a grafted seedling is used for producing a grafted plant or a grafted seedling according to the invention. Thus, it is understood that also grafted plants or grafted seedlings having at least two different rootstocks and/or at least two different scions can be produced by the first or second method according to the invention for producing a grafted plant or a grafted seedling.

CGMMV resistant grafted plants or seedlings obtainable or obtained by the first or second method according to the invention for production of a grafted plant or a grafted seedling are also an embodiment of the invention.

Provision of plants according to the invention now allows combating CGMMV infection of *Citrullus* plants, combating, reducing or preventing CGMMV induced yield loss of *Citrullus* fruits or producing CGMMV resistant seeds from *Citrullus* plants.

A further embodiment of the invention therefore concerns a method for combating CGMMV infection in *Citrullus* plants comprising the following steps:

sowing a seed according to the invention or transplanting a grafted plant according to the invention or transplanting a grafted seedling according to the invention, growing the plant sown or growing the grafted plant or the grafted seedling according to step a).

"Transplanting" is used herein to describe the transfer of a seedling or a grafted seedling into a cultivation or growing area by hand work or machine.

In step a) of the method according to the invention for combating CGMMV infection of *Citrullus* plants seeds are preferably sown into a cultivation area, which can be any area suitable for growing *Citrullus* plants, like a field, a pot or a tray, wherein the pot or tray can be placed into the open space or into a greenhouse and the growing area may or may not be covered, e.g. with foil or gaze tunnels.

Preferably the *Citrullus* plants grown according to step b) of the method according to the invention for combating CGMMV do show no symptoms (scale 4) or mild symptoms (scale 3) caused by CGMMV upon infection with CGMMV, due to the resistance to CGMMV comprised by the seeds or grafted transplants according to step a).

In one specific embodiment the method according to the invention for combating CGMMV infection is a method for combating, reducing or preventing CGMMV induced yield loss of fruits of *Citrullus* plants, wherein the method comprises a further step c) which is harvesting the fruits from plants grown according to step b).

Fruits of CGMMV resistant plants obtainable or obtained by the method according to the invention for combating, reducing or preventing CGMMV induced yield loss of fruits of *Citrullus* plants, especially cultivated watermelon plants, are also an embodiment of the invention. The fruits can be distinguished from other fruits due to the presence of one or more QTLs, which are detectable by the SNP markers linked to the QTLs. In other words, the fruits comprise at least one recombinant chromosome, comprising an introgression fragment from a *C. colocynthis* donor, which introgression fragment is detectable by the sequences and SNP markers linked to the QTL. The fruits are preferably of good agronomic quality, have a high brix, good fruit texture an no internal symptoms of CGMMV infection. Preferably the CGMMV virus is not detectable in the fruits using e.g. RT-qPCR. The fruits comprise one, two, three or four recombinant chromosomes, depending on the ploidy. In one aspect the fruits are triploid and seedless, and comprise three copies of the recombinant chromosome and thus three copies of the introgression fragment and three copies of the donor SNP nucleotides, e.g. for SNP14 linked to QTL7.1 the SNP genotype would be 'AAA' (three copies of SEQ ID NO: 14) for the resistant plants and plant parts. In a diploid watermelon plant homozygous for QTL7.1, the SNP genotype would be 'AA' for SNP14 and in a tetraploid watermelon plant homozygous for QTL7.1, the SNP genotype would be 'AAAA' for SNP14. The same applies for the other SNP markers of Table 1 and Table 6. SNP genotyping can be done using various methods, e.g. a KASP assay may be used or other methods, such as sequencing etc.

"Brix" or "degree Brix" or "° brix" refers to the mean total soluble solids content as measured on several mature fruits using a refractometer. Preferably the mean of at least three fruits, each measured between the center and the rind of the cut-open fruit, is calculated.

In one aspect the fruits of the cultivated watermelon plants of the invention, comprising one or more QTLs as described, have a brix of at least 9.0, preferably at least 10.0 or 11.0 or more.

In one aspect the fruits of the cultivated watermelon plants of the invention, comprising one or more QTLs as described, are marketable fruits. "Marketable" in relation to fruit quality means that the watermelon fruits are suitable for being sold for fresh consumption, having no external or internal symptoms of CGMMV infection, having good flavour (no off-flavours), a degree brix of at least 9.0, preferably at least 10.0 or at least 11.0 and preferably also a uniform fruit flesh color, being e.g. white (e.g. variety Cream of Saskatchewan), yellow (e.g. variety Yamato Cream 1), orange (e.g. variety Tendersweet), pink (e.g. variety Sadul), pinkish red (e.g. variety Crimson Sweet), red (e.g. variety Sugar Baby) or dark red (e.g. variety Dixie Lee).

"Uniform fruit flesh color" means that the color throughout the mature fruits, when cut open through the middle (midsection), is evenly distributed throughout the fruit flesh, i.e. not patchy. Thus, a red fruit is red throughout the fruit flesh and does not contain white patches. An example of a fruit with uniform red color is the diploid variety Premium F1 (Nunhems).

An advantage of the present invention is that fruits of non-genetically engineered *Citrullus* plants or grafted plants according to the invention or fruits produced by plants used in one of the methods according to the invention described herein do not show CGMMV induced symptoms. Thus, even if plants or scions according to the invention grown in a field are infected by CGMMV to a low level, those plants will produce fruits free of CGMMV symptoms. These fruits will be marketable and thus yield loss can be reduced or prevented.

In another specific embodiment the method according to the invention for combating CGMMV infection is a method for producing CGMMV resistant seeds, wherein the method in addition to the method for combating, reducing or preventing CGMMV induced yield loss of fruits comprises a further step d) which is obtaining seeds from the fruits of plants harvested according to step c). Optionally, the method according to the invention for producing CGMMV resistant seeds comprises a further step e) wherein the seeds obtained in step d) are grown into plants and said plants are tested for resistance to CGMMV, wherein resistance to CGMMV is preferably analysed phenotypically, e.g. by means of visual evaluation of symptoms and/or genotypically e.g. by means of SNP marker genotyping. Seeds will be obtained when the flowers of diploid or tetraploid cultivated watermelons according to the invention are fertilized e.g. by own pollen (self-fertilization) or other pollen (cross-fertilization). If the diploid or tetraploid cultivated watermelon plants are homozygous for the introgression fragment(s), the 51 seed (produced after self-fertilization) will also be homozygous and the F1 seed (produced after cross-fertilization) will be homozygous or heterozygous, depending on whether the pollen is from a plant which also comprises the introgression fragment(s) or which lacks the introgression fragment(s).

CGMMV resistant seeds obtainable or obtained by the method according to the invention for producing CGMMV resistant seeds are also an embodiment of the invention. The seeds comprise at least one recombinant chromosome as described. Preferably, the plants grown from the seeds are also CGMMV resistant (e.g. scale 4 or scale 3 in the CGMMV assay) due to the introgression fragment comprising the QTL(s). This will be the case for the dominant QTLs, QTL7.1 and/or QTL9.1. The recessive QTLs need to be in homozygous form to express a CGMMV resistance phenotype.

In one aspect, CGMMV resistant seeds produced on plants of the invention are free of CGMMV virus, i.e. no CGMMV virus is detectable in those seeds by e.g. RT-qPCR. Thus, in one aspect, the one or more QTLs of the invention result in CGMMV virus not being transmittable to the seeds produced on such plants. In one aspect a cultivated watermelon plant comprising QTL7.1 and/or QTL9.1 will produce CGMMV free seeds in its fruits.

The plants and plant parts of the invention have various uses.

Use of one or more of markers selected from SNP1, SNP1, SNP3, SNP4, SNP5, and SNP6; and/or use of one or more of markers selected from SNP7, SNP8 and SNP9; and/or use of one or more of markers selected from SNP10, SNP11 and SNP12; and/or use of one or more of markers selected from SNP13, SNP14, SNP15, SNP16, SNP17 and SNP18; and/or use of one or more of markers selected from SNP19, SNP20, SNP21, SNP22, SNP23 and SNP24, for identification of a CGMMV resistant *Citrullus* plant or plant part or plant cell, preferably a CGMMV resistant *Citrullus colocynthis* plant or plant part or plant cell or a CGMMV resistant *Citrullus lanatus* ssp. *vulgaris* plant or plant part or plant cell.

Use of one or more of markers selected from SNP1, SNP1, SNP3, SNP4, SNP5, and SNP6; and/or use of one or more of markers selected from SNP7, SNP8 and SNP9; and/or use of one or more of markers selected from SNP10, SNP11 and SNP12; and/or use of one or more of markers selected from SNP13, SNP14, SNP15, SNP16, SNP17 and SNP18; and/or use of one or more of markers selected from SNP19, SNP20, SNP21, SNP22, SNP23 and SNP24, for identification or detection of a CGMMV resistance conferring QTL or introgression fragment comprising a CGMMV resistance conferring QTL in a *Citrullus* plant or plant part or plant cell, preferably a CGMMV resistant *Citrullus colocynthis* plant or plant part or plant cell or a CGMMV resistant *Citrullus lanatus* ssp. *vulgaris* plant or plant part or plant cell.

Use of one or more of markers selected from SNP1, SNP1, SNP3, SNP4, SNP5, and SNP6; and/or use of one or more of markers selected from SNP7, SNP8 and SNP9; and/or use of one or more of markers selected from SNP10, SNP11 and SNP12; and/or use of one or more of markers selected from SNP13, SNP14, SNP15, SNP16, SNP17 and SNP18; and/or use of one or more of markers selected from SNP19, SNP20, SNP21, SNP22, SNP23 and SNP24, for identification or detection of a plant or plant part or plant cell comprising a CGMMV resistance conferring QTL or an introgression fragment comprising a CGMMV resistance conferring QTL, wherein the plant or plant part or plant cell is a *Citrullus* plant or plant part or plant cell, preferably a *Citrullus colocynthis* plant or plant part or plant cell or a *Citrullus lanatus* ssp. *vulgaris* plant or plant part or plant cell.

Use of one or more of markers selected from SNP1, SNP1, SNP3, SNP4, SNP5, and SNP6; and/or use of one or more of markers selected from SNP7, SNP8 and SNP9; and/or use of one or more of markers selected from SNP10, SNP11 and SNP12; and/or use of one or more of markers selected from SNP13, SNP14, SNP15, SNP16, SNP17 and SNP18; and/or use of one or more of markers selected from SNP19, SNP20, SNP21, SNP22, SNP23 and SNP24, for introgression of CGMMV resistance (or a CGMMV resistance conferring QTL) into a CGMMV susceptible cultivated watermelon plant.

Use of a *Citrullus colocynthis* plant or a *Citrullus colocynthis* plant cell according to the invention for the production of a CGMMV resistant *Citrullus lanatus* plant preferably for the production of a *Citrullus lanatus* subspecies *vulgaris* plant or for the production of a *Citrullus lanatus* plant cell preferably a *Citrullus lanatus* subspecies *vulgaris* plant cell is another embodiment of the invention. In a preferred embodiment, the *Citrullus colocynthis* plant or a *Citrullus colocynthis* plant cell according to the invention is used for producing CGMMV resistant *Citrullus lanatus* plants according to the invention.

Use of pollen of a *Citrullus colocynthis* plant according to the invention for pollinating a *Citrullus lanatus* plant preferably a *Citrullus lanatus* subspecies *vulgaris* plant is also an embodiment of the invention.

Use of a *Citrullus* plant or a *Citrullus* plant cell according to the invention, for the production of a grafted plant, preferably a grafted plant according to the invention is another embodiment of the invention.

Use of non-genetically engineered *Citrullus* plants or a *Citrullus* plant cells according to the invention for the production of CGMMV resistant seeds is another embodiment of the invention.

Use of seeds deposited under accession number NCIMB 42624 for the production of a CGMMV resistant *Citrullus* plant, preferably a non-genetically engineered CGMMV resistant *Citrullus* plant according to the inventions is also an embodiment of the invention.

Use of a non-genetically engineered *Citrullus* plants or *Citrullus* plant cells according to the invention for the production of fruits, preferably fruits according to the invention is another embodiment of the invention.

Use of non-genetically engineered *Citrullus* plants or *Citrullus* plant cells according to the invention, for the production of seedless fruits, preferably seedless fruits according to the invention, is another embodiment of the invention.

The verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one", e.g. "a plant cell" refers also to several cells plants, etc. Similarly, "a fruit" or "a plant" also refers to a plurality of fruits and plants.

In one aspect the plants, plant parts and plant cells according to the invention are not exclusively obtained by means of an essentially biological process as defined by Rule 28 (2) EPC (European Patent Convention). For example causal gene of the *C. colocynthis* QTLs, e.g. QTL7.1 or QTL9.1, may determined by e.g. fine mapping and/or sequencing of the chromosome 7 or chromosome 9 region where the QTL is found, the ortholog gene of cultivated watermelon may be determined and the cultivated watermelon orthologous gene may be mutated, by e.g. UV mutagenesis, EMS mutagenesis, CRISPR-Cas genome modification, etc. Thereby a CGMMV resistant watermelon plant comprising a modified gene underlying e.g. QTL7.1 or QTL9.1 can be generated. In this aspect, the references herein to *C. colocynthis* introgression fragments is replaced by the watermelon plants being CGMMV resistant because they 'comprise a (human induced) mutated gene of the orthologous watermelon gene of the *C. colocynthis* gene present at QTL7.1 locus or QTL9.1 locus' (or any of the other loci).

In one aspect the CGMMV resistance conferring QTLs described herein are not obtained from/obtainable from *C. colocynthis* accessions PI386015, PI388770, PI525082 and PI537300 of the USDA core collection.

Seed Deposit

Diploid *Citrullus colocynthis* seeds of CGMMV resistant plants have been deposited by Nunhems B.V. under the Budapest Treaty under accession number NCIMB 42624 at NCIMB Ltd., Bucksburn Aberdeen AB21 9YA, Scotland on 10 Aug. 2016.

Access to the deposits will be available during the pendency of this application to persons determined by the Commissioner of Patent and Trademarks to be entitled thereto upon request.

The Applicant requests that samples of the biological material and any material derived from said samples be only released to a designated Expert in accordance with Rule 32(1) EPC or related legislation of countries or treaties having similar rules and regulation, until the mention of the grant of the patent, or for 20 years from the date of filing if the application is refused, abandoned, withdrawn or deemed to be withdrawn.

Subject to 37 C.F.R. § 1.808(b), all restrictions imposed by the depositor on the availability to the public of one or more deposits will be irrevocably removed upon the granting of the patent by affording access to the deposits. The deposits will be maintained for a period of 30 years, or 5 years after the most recent request, or for the enforceable life of the patent whichever is longer, and will be replaced if it ever becomes non-viable during that period. Applicant does not waive any rights granted under this patent on this application or under the Plant Variety Protection Act (7 USC 2321 et seq.).

DESCRIPTION OF SEQUENCES

Figure 1:
FIG. 1: NCIMB 42624 plant used for production of scions and CGMMV infected *Citrullus lanatus* cultivar Sugar baby plant (picture taken at 25 dpi) used for production of rootstock (A); NCIMB 42624 scion grafted onto CGMMV infected *Citrullus lanatus* cultivar Sugar baby rootstock, picture taken after 140 dpi shows no symptoms on scion (Scale 4) (B); CGMMV infected *Citrullus lanatus* cultivar Sugar baby plant, picture taken after 140 dpi shows severe symptoms (C)
Figure 1:
Figure 1:

SEQ ID NO: 1 to SEQ ID NO:6 refer to sequences of chromosome 1 linked to QTL1.1 from *C. colocynthis* comprising the donor nucleotide of SNP1 to SNP6 respectively;

SEQ ID NO: 7 to SEQ ID NO: 9 refer to sequences of chromosome 4 linked to QTL4.1 from *C. colocynthis* comprising the donor nucleotide of SNP7 to SNP9 respectively;

SEQ ID NO: 10 to SEQ ID NO: 12 refer to sequences of chromosome 5 linked to QTL5.2 from *C. colocynthis* comprising the donor nucleotide of SNP10 to SNP12 respectively;

SEQ ID NO: 13 to SEQ ID NO: 18 refer to sequences of chromosome 7 linked to QTL7.1 from *C. colocynthis* comprising the donor nucleotide of SNP13 to SNP18 respectively;

SEQ ID NO: 19 to SEQ ID NO: 24 refer to sequences of chromosome 9 linked to QTL9.1 from *C. colocynthis* comprising the donor nucleotide of SNP19 to SNP24 respectively;

SEQ ID NO 25: Reverse primer used in RT PCR for detection of CGMMV RNA in plant tissue.

SEQ ID NO 26: Forward primer used in RT PCR for detection of CGMMV RNA in plant tissue.

SEQ ID NO 27: Sense primer used in quantitative RT PCR for quantification of CGMMV RNA in plant tissue.

SEQ ID NO 28: Antisense primer used in quantitative RT PCR for quantification of CGMMV RNA in plant tissue.

SEQ ID NO 29: Probe oligonucleotide used in quantitative RT PCR for quantification of CGMMV RNA in plant tissue.

EXAMPLES

General Methods

Example: Mechanical Leaf Inoculation to Evaluate CGMMV Resistance

Item 1: Preparation of CGMMV Inoculum for Plant Infection

Inoculum for infection of *Citrullus* plants was produced from CGMMV susceptible cucumber plants (e.g. variety Sheila, Nunhems B.V.) infected with European type strain Ve459 (CNR, Turin). Fresh young leaves showing clear symptoms of CGMMV infection (symptomatic leaves) were taken off the cucumber plants. Per 1 gram of symptomatic cucumber leaves 5 ml of refrigerated (5° C.) 0.03M phosphate buffer were added and per 1 gram of cucumber leaf 0.05 gram active carbon and 0.1 gram diatomaceous earth was added. The leaf material was crushed with a pestle in a mortar kept ice cold during and after crushing.

For testing if *Citrullus* plants are resistant to CGMMV it is advisable to use freshly prepared inoculum from freshly multiplied material.

Item 2: Infection of (*Citrullus*) Plants with CGMMV

Leaf inoculation was done by rubbing the inoculum onto the first true leaf of young seedlings. Thus, the seedlings of (*Citrullus*) plants were inoculated with inoculum, prepared as described under General Methods Item 1, when the first true leaf is expanded (approximately 15-20 days after sowing). Seedlings were inoculated a second time 4 to 5 days after the first inoculation. Control seedlings are inoculated with buffer only (Mock inoculation). The inoculated plants were kept in indirect sunlight and direct sunlight was avoided until the second inoculation. The temperature regime for maintaining the inoculated seedlings was 18° C. at night time and 25° C. at daytime with 12-14 hours of daylight. Inoculate preferably at least 10 plants per genotype (e.g. CGMMV resistant genotype, susceptible control genotype) in at least two replicates. In addition include a number of plants which are mock inoculated.

Item 3: Assessment of Disease Symptoms

Plants having been inoculated were analyzed for symptoms and/or presence for CGMMV virus at the following points in time after the first inoculation (dpi, days post inoculation):

15 dpi
30 dpi
45 dpi
60 dpi

In case desired, fruits can be tested for symptoms and/or presence of CGMMV after e.g. about 140 dpi or even later.

Control Plants

Controls have to be included into all test series. It is important to include (*Citrullus*) plants known to be susceptible to CGMMV (e.g. *Citrullus lanatus* commercial variety Sugar baby) as a positive control to check for efficiency of infection with CGMMV. Preferably at least 95% of the positive control plants should show severe symptoms (scale 1) on leaves after 20 dpi and preferably fruits produced by these plants should show severe symptoms. In addition, negative control plants should be included represented by CGMMV susceptible plants which have been inoculated with phosphate buffer only as Mock inoculation. In addition, non-inoculated plants can be included into the test series. The negative controls should not show symptoms of CGMMV infection at any time in leaves or fruits and CGMMV protein and/or RNA should not be detectable in Mock inoculated plants.

Visual Evaluation of CGMMV Symptoms on Leaves

Figure 2:
FIG. 2: Example of *Citrullus* plants showing severe symptoms, leaf deformation, blistering and clear mosaic after inoculation with CGMMV representing scale 1 according visual evaluation of symptoms described under General Methods.

Visually evaluated symptoms on leaves are classified according to the following scale:

Scale 1: Severe symptoms: leaf deformation, blistering and clear mosaic (exemplified in FIG. 2)

Figure 3:
FIG. 3: Example of *Citrullus* plants showing medium symptoms, mild leaf deformation but clear mosaic after inoculation with CGMMV representing scale 2 according visual evaluation of symptoms described under General Methods.

Scale 2: Medium symptoms: mild leaf deformation but clear mosaic (exemplified in FIG. 3)

Figure 4:
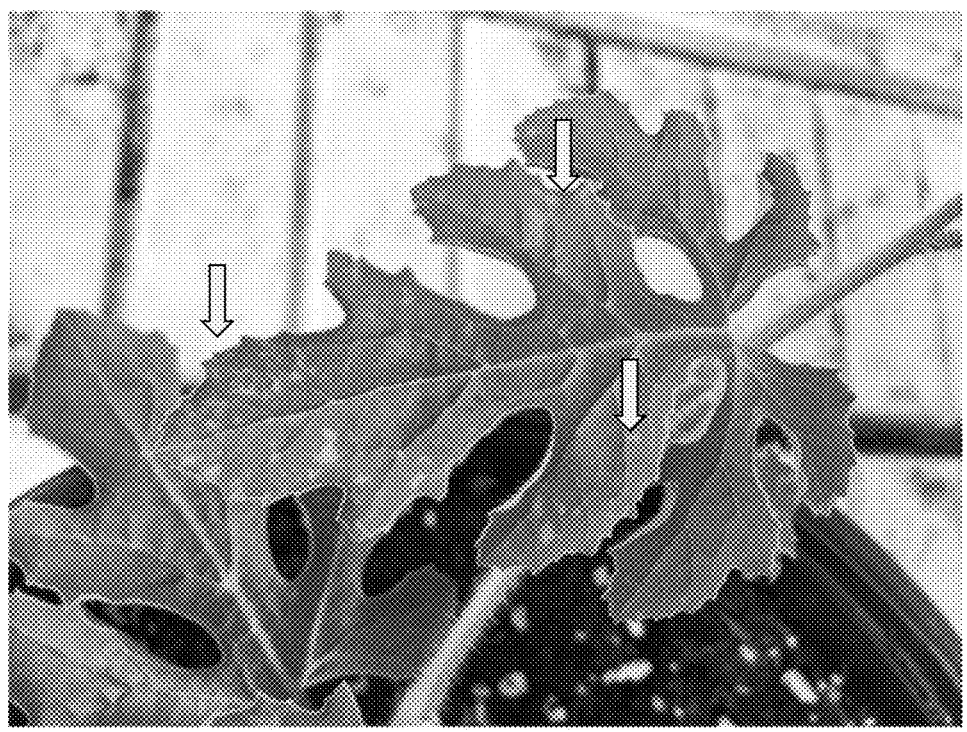
FIG. 4: Example of a *Citrullus* plant showing mild symptoms, very mild mosaic and few clearing spots after inoculation with CGMMV representing scale 3 according visual evaluation of symptoms described under General Methods.
Figure 5:
FIG. 5: Example of fruit showing severe CGMMV symptoms, the fruit being produced by a CGMMV susceptible *Citrullus* plant inoculated with CGMMV.
Figure 6:
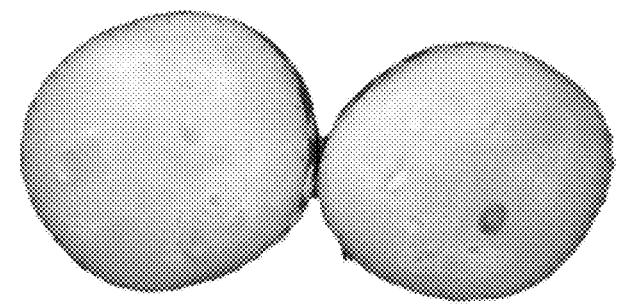
FIG. 6: Example of fruit showing no symptoms, the fruit being produced by a CGMMV resistant *Citrullus* plant inoculated with CGMMV.

Scale 3: Mild symptoms: very mild mosaic and few clearing spots (exemplified in FIG. 4)

Scale 4: No symptoms (exemplified in FIG. 1B)

Virus Detection in Inoculated Plant Tissue: ELISA

For demonstrating presence or absence of CGMMV in plants an ELISA assay was performed after the second evaluation (30 dpi) for all plants classified as scale 4 by visual evaluation of symptoms. Depending on the results obtained by the ELISA assay, the plants tested were classified according to the following scale:

Negative by ELISA

Low positive if Absorbance is <0.5

Positive by ELISA if Absorbance is >0.5

Presence or absence of CGMMV in plant material can also be evaluated by RT-PCR or quantified by RT-qPCR detection (see General Methods item 4) and/or by the Tissue print or DotBlot (General methods item 5).

Item 4: Virus detection in inoculated plant tissue: PCR detection of CGMMV in plant tissue Presence of CGMMV in plant material was detected by reverse transcriptase polymerase chain reaction (RT-PCR) and for quantification of CGMMV in plant material reverse transcriptase quantitative polymerase chain reaction (RT-qPCR, TaqMan) was used. See also Hongyun et al., 2008, J Virological Methods 149, 326-329, incorporated by reference.

a) Extraction of RNA from Plant Material

Leaf tissue (200 mg) was ground to a fine powder in liquid nitrogen with a pestle in a mortar and transferred into a sterile microcentrifuge tube. Total RNA was extracted with Trizol reagent (Invitrogen) according to the manufacturer's instruction. The resulting RNA pellet was resuspended in 30 µl DEPC-treated water and stored at −80° C. RNA concentration was determined by ND-1000 Spectrophotometer (NanoDrop Technologies).

b) Reverse Transcriptase PCR (RT-PCR)

The oligonucleotides used for RT-PCR were designed based on the CGMMV coat protein gene and 3' noncoding region (NCR) nucleotide sequence available from the EMBL database. The first strand of cDNA was synthesized by the SuperScript II reverse transcriptase (Invitrogen) primed with reverse primer: 5'-TTG CAT GCT GGG CCC CTA CCC GGG GAA AG-3' (SphI; SEQ ID NO 25). The sequence of forward primer used for PCR is: 5'-CCG AAT TCA TGG CTT ACA ATC CGA TCA C-3' (EcoRI; SEQ ID NO 26). The thermal cycling scheme was: 3 minutes at 94° C., 35 cycles of 30 seconds at 94° C., 45 seconds at 53° C., 1 minute at 72° C. followed by a final incubation of 7 minutes at 72° C. Expected PCR products of 700 base pairs were cloned into pGEM-3Zf plasmid and positive clones were sequenced in both directions with an automated ABI 3730 DNA sequencer to confirm the amplified sequence to be obtained from CGMMV virus RNA.

c) RT-qPCR

The primers and probe for the TaqMan assay were designed with the Primer Express software (Applied Biosystems, ver. 2.0), following the procedure as described in the instruction supplied by manufacturer. CGMMV specific primers were 5'-GCA TAG TGC TTT CCC GTT CAC-3' (sense; SEQ ID NO 27) and 5'-TGC AGA ATT ACT GCC CAT AGA AAC-3' (antisense; SEQ ID NO 28). The probe was 5'-CGG TTT GCT CAT TGG TTT GCG GA-3' (SEQ ID NO 29), labelled with 6-carboxyfluorescein (FAM) and 3' end was labelled with N,N,B',N'-tetramethyl-6-carboxyrhodamine (TAMRA). All reactions were carried out in a final volume of 50 µl containing: 25 µl 2× Master Mix without UNG, 1.25 µl 40× MultiScribe and RNase Inhibitor Mix, 1 µl forward primer (20 µL), 2 µl reverse primer (20 µL), 0.5 µl probe (20 µL), 1 µl total RNA or 5 µl RNA transcripts, and the volume of DEPC-water was adjusted with template. Thermo-cycling was run on LightCycler® 96 (Roche LifeScience) as follows: 30 minutes at 48° C., 10 minutes at 95° C., 40 cycles of 15 seconds at 95° C., 1° min at 60° C. Conversion of microgram of single stranded RNA to picomole and the number of RNA molecules was performed as described by Olmos et al. (2005, J Virol Methods 128(1-2), 151-155). Tenfold serial dilutions of the transcripts were prepared from 5×1012 to 50 copies per 5 µl, aliquoted and stored at −80° C. Dilutions from 5×108 to 5×100 were amplified by the real time RT-PCR assay. The stable amplification could be observed as low as 50 copies of RNA transcripts undertaking three repetitions of assay.

Item 5: Detection of CGMMV by Hybridization (Tissue Print or DotBlot)

Membrane Preparation for Tissue Print

Wearing gloves, prepare the nylon membrane by cutting to the required size with sterilized scissors, and place a micro-plate grid template on top (actual size depends on the type of sample being used). Make a transversal cut across the leaf stalk with a clean, sterile scalpel, and lightly press into one of the grids until all sap is absorbed. Make a fresh cut for each subsequent print. For purified DNA or RNA samples, 1 µl of sample is sufficient.

Include healthy negative controls and known infected positive controls of a respective same plant species. Purified virus or an amplified PCR product thereof should also be included as a positive control. Wait until the membrane is totally dry, and fix the nucleic acids to the membrane using UV light at 0.120 J cm−2 (crosslink). Store the dry membranes at room temperature, sealed in plastic bags.

Membrane Preparation for DotBlot

Sample tissue is weighed and ground in the appropriate extraction buffer at the appropriate dilution. Take 10-20 µl of extract with a micropipette, and carefully remove the tip, ensuring the liquid inside does not rise and become air-locked. Lightly touch (swiftly) the pipette tip against the membrane, using the micro-plate grid as a guide and apply the extract onto the membrane (printing). The resulting dots are about 250 nl in volume, and 4 can be placed in each grid position. Use 2-4 dots per sample, depending on the purpose of the membrane and quality of hybridization probe.

Print controls, crosslink and store as described above for Tissue Print membranes.

You may print duplicate membranes as back-up in case problems during processing should arise.

Prehybridization of Membranes

Place the membrane prepared as described above for tissue prints or DotBlots into a hybridization tube using flat tweezers. Add pre-hybridization solution (DIG Easy plus 1% blocking agent) at room temperature (sufficient to cover the membrane; e.g. 20 ml for 8×12 cm membrane, 10 ml for 8×6 cm). Incubate for aprox. 2 hours at 54° C. rotating in an hybridization oven. Ensure that the membrane does not dry out from now on.

Hybridization of Membranes

Prepare fresh hybridization solution (DIG Easy solution plus 1% blocking agent), using frozen stock probe solutions to obtain 80-120 ng probe per 8×12 cm membrane. Pre-heat the hybridization solution for 10 minutes at 100° C. (for DNA probes) or 65° C. for RNA probes. Discard the pre-hybridization solution from the membranes and add the diluted probe solution to the membranes. Incubate overnight at 54° C. rotating in the hybridization oven.

Washing of Membranes

Discard hybridization solution from the membranes and carry out the following steps in the hybridization tube with rotation in the hybridization oven:

1. Wash with 2× hybridization volume in 6×SSC+1% SDS for 40 minutes at hybridization temperature.

2. Discard liquid and repeat wash.

3. Transfer membrane to a detection tray+Solution 1 (avoid drying out of the membrane).

Detection

Transfer the membrane to a tray slightly larger than the membrane. From here on, the process is at room temperature and with gentle agitation. Adjust the solution volumes to the tray and membrane size (e.g. 600 µl/cm2 or 50 ml for 8×12 cm membrane). It is important that the membrane does not dry out during the following steps:

Wash the Membrane with the Following Solutions:

1. Solution I, 1 min
2. Wash solution, 5 min
3. Solution I, 1 min
4. Solution II, 30 min (prepare 2× volume in measuring cylinder)
5. Solution II (from previous step)+Anti-DIG(1:20000), 30 min
6. Wash solution, 15 min
7. Wash solution, 15 min
8. Solution I, 1 min
9. Solution III, 5 min minimum Dilute alkaline-phosphatase chemiluminescent substrate (CDP-Star (1:100) in 600 µl of Solution III. Place the membrane between two sheets of acetate and distribute the substrate evenly over the membrane using a micropipette (1 drop=4 small quadrants). Mix by lifting and lowering the top acetate several times, taking care not to introduce air bubbles. Incubate 5 minutes in the dark (e.g. cover with aluminum foil). Remove excess substrate by pressing with filter paper and heat-seal edges of acetate.

The following reagents are needed for preparing the solutions mentioned herein:

Reagents:
Blocking agent (Roche)
Maleic Acid.
NaCl

Tris-HCL
Tween 20
Anti-Dig (Roche).
CDP-Star (Roche).
Solutions:
Solution I: 0.1 M Maleic acid, 0.15 M NaCl, pH 7.5
Solution II: 1% blocking agent in Solution I.
Solution III: 0.1 M Tris-HCl pH 9.5, 0.1 M NaCl
Wash Solution: 0.3% Tween 20 in Solution I
Digital Imaging Place membrane in Digital Imaging chamber, and take one photograph with ambient lighting (Nikon Control Pro2, 50 mm objective, manual control with remote shooting enabled, ISO 0.3 step over 6400, long-exposure noise reduction box is checked, camera pre-chilled 30 minutes minimum, <10° C.).

Close the chamber, change shutter speed to Bulb and Aperture to 1.4. Using DSLR_Bot, Long Exposure function, set exposure time to 5 minutes 03 seconds. Ensure infrared cable is fully inserted, output level is at maximum and press Start (a "click" should be audible). Camera takes one image with aperture open, and a second with aperture closed for noise reduction—total time of 10 minutes 06 seconds for each 5 minute 03 seconds photo.

One photo of 5 min exposure is roughly equivalent to a conventional image of 2-4 hours exposure. If stronger signal is required, a 10 minutes digital exposure (equivalent to overnight conventional image) can be done. For external diagnostics or low signal, a conventional overnight exposure is recommended.

Item 6: Grafting of *Citrullus* Plants

Rootstocks were prepared from 15 days old CGMMV inoculated *Citrullus lanatus* cultivar Sugar baby plants or cultivar Ercole (Nunhems B. V.). Scions were prepared from 20 days old NCIMB 42624 plants. Scions were grafted onto the rootstock by making a slant cut on the stem of the rootstock and on the shoot of the scion and joining these so that the vascular system is joined. After healing at high humidity, grafted plants were transferred to the greenhouse.

Examples—Results

Results Item 1: Identification of CGMMV Resistant *Citrullus* Plants

A group of various different *Citrullus* species accessions was grown in a greenhouse or climate chamber infected with CGMMV according to the method described herein under General Methods. Inoculum for CGMMV infection was produced according to General Methods Item 1 and inoculated plants were evaluated visually for symptoms as described under General Methods Item 3. One single *Citrullus colocynthis* plant being free of CGMMV induced symptoms (scale 4) was identified. The plant was selfed for a number of times and a selected CGMMV resistant plant was multiplied to obtain seeds for seed deposit under the Budapest treaty, designated as having accession number NCIMB 42624.

Results Item 2: Production of CGMMV Resistant Plants and Analysis Thereof

*Citrullus lanatus* Plants

Pollen from NCIMB 42624 was used to pollinate elite lines of *Citrullus lanatus* subspecies *vulgaris*. F1 plants were grown from seeds produced by the crosses for further analysis in respect to CGMMV resistance.

Also F2 plants were made by selfing the F1 plants. It has to be noted, that it was complicated to obtain F2 seeds and backcrosses from F1 plants (NCIMB 42624x elite lines of *Citrullus lanatus* subspecies *vulgaris*). Only few fruits did develop and in those fruits most of the seeds were empty.

The F1 plants were tested for CGMMV resistance and presence of CGMMV virus using the mechanical leaf inoculation method described in General Method Item 1-3 and RT-qPCR described in General Method Item 4.

The results were as follows. The Mock inoculated plants showed no symptoms. The positive control, Sugar baby, plants showed CGMMV symptoms of Scale 1. The F1 plants were CGMMV resistant and showed no symptoms (Scale 4).

TABLE 2

Quantitative analysis of CGMMV RNA in the plants was performed 15 dpi, 30 dpi and 60 dpi for each set of plants:

| | Average Concentration (ng/μl) | | |
|---|---|---|---|
| Plant | 15 dpi | 35 dpi | 60 dpi |
| Mock Sugar Baby | — | — | — |
| Mock F1 | — | — | — |
| Sugar baby inoculated_rep 1 | 1.4 | $3.35 \times 10^{-2}$ | 1.26 |
| Sugar baby inoculated_rep 2 | 2.1 | $1.53 \times 10^{-2}$ | 0.41 |
| Average of Sugar baby inoculated | 1.75 | $2.44 \times 10^{-2}$ | 0.83 |
| F1 inoculated_rep 1 | $1.2 \times 10^{-4}$ | — | $1.17 \times 10^{-5}$ |
| F1 inoculated_rep 2 | — | $1.09 \times 10^{-4}$ | $3.68 \times 10^{-5}$ |
| F1 inoculated_rep 3 | $5.3 \times 10^{-5}$ | — | $1.86 \times 10^{-5}$ |
| F1 inoculated_rep 4 | $7.2 \times 10^{-6}$ | $1.81 \times 10^{-6}$ | $1.03 \times 10^{-5}$ |
| Average of F1 inoculated | $4.5 \times 10^{-5}$ | $2.7 \times 10^{-5}$ | $1.93 \times 10^{-5}$ |

Results of RT-qPCR above shows the amount of CGMMV RNA in plant material. "Mock" indicates plants inoculated with buffer but without CGMMV. "inoculated" indicates plants having been inoculated with CGMMV as described in the mechanical leaf inoculation test in General Methods Item 1-3. "Sugar" indicates susceptible *Citrullus lanatus* cultivar Sugar baby plants. "F1" indicates plants obtained from crosses between NCIMB 42624x Citrullus lanatus subspecies *vulgaris* elite lines. "rep" indicates different plants, wherein each rep consists of a group of 6 plants.

RT-qPCR is a highly sensitive method for detecting CGMMV RNA molecules in plant samples (Hongyun et al., 2008, J Virological Methods 149, 326-329). As can be seen from the Table 2 above using the highly sensitive RT-qPCR method CGMMV RNA can be detected in all plants analysed at nearly all points in time (15 dpi, 30 dpi and 60 dpi). It is clearly derivable from the Table 2 that the amount of CGMMV RNA in F1 plants obtained from a cross between NCIMB 42624x *Citrullus lanatus* subspecies *vulgaris* elite lines is orders of magnitude lower than the amount of CGMMV RNA in CGMMV susceptible *Citrullus lanatus* cultivar Sugar baby. The amount was at all time points below 5.0×10-5 ng/μl on average of the four replicates and progressively lower at later time points. The susceptible control had an average of at least 0.02 ng/μl (at 35 dpi) but even much higher levels at 15 dpi and 60 dpi, above 1.7 ng/μl and above 0.8 ng/μl respectively.

From the visual evaluation of symptoms it is clear that F1 plants are resistant to CGMMV as they produce no symptoms after inoculation with CGMMV (scale 4). *Citrullus lanatus* cultivar Sugar baby is known to be susceptible to CGMMV and does show severe symptoms (scale 1) after inoculation with CGMMV. Therefore, the very low amounts of CGMMV in F1 plants shown in the Table above clearly indicates that CGMMV resistance is correlated with a significant decrease of CGMMV RNA in respective plant material. The F2 plants were also without CGMMV symptoms (scale 4) when tested in the mechanical leaf inoculation method described in the General Method items 1-3. Also the fruits produced on the F2 plants showed no symptoms on the outside or inside. F2 plants which were without symptoms (scale 4) also had an extremely low amount of virus titer in the leaves (RT-qPCR data not shown), significantly reduced compared to the susceptible control.

Grafted Plants

Scions from NCIMB 42624 were grafted onto CGMMV infected rootstocks prepared from commercial *Citrullus lanatus* subspecies *vulgaris* plants (cultivar Sugar Baby) or from a *Curcubita maxima* x *Curcubita moshata* cultivar Ercole hybrid (Nunhems B.V.) according to the method described herein under General Methods.

Analysis of the Plants

Greenhouse grown F1 plants (NCIMB 42624 x *Citrullus lanatus* subspecies *vulgaris* elite lines), grafted plants composed of a scion from NCIMB 42624 and an infected rootstock from *Citrullus lanatus* subspecies *vulgaris* cultivar Sugar Baby ("NCIMB42624—Sugar baby") and grafted plants composed of a scion from NCIMB 42624 and an infected rootstock from a *Curcubita maxima* x *Curcubita moshata* cultivar Ercole hybrid ("NCIMB42624—Ercole") were analysed. The non-grafted plants (NCIMB42624, F1, Sugar Baby) were inoculated with CGMMV using the mechanical leaf inoculation. The grafted plants were made using the rootstock of a CGMMV infected Sugar Baby plant or Ercole plant as described in the General Methods.

In none of the plants symptoms on leaves caused by CGMMV could be detected by visual analysis. All plants were determined to be scale 4 by the visual evaluation of symptoms as described herein under General Methods item 3.

Furthermore, all plants did produce fruits appearing normal from outside and showing no symptoms of deteriorated or water soaked pulp on the inside. A representative picture of a fruit produced by such plants is given in FIG. 6.

Nearly all non-grafted *Citrullus lanatus* subspecies *vulgaris* cultivar Sugar Baby plants inoculated with CGMMV did show clear symptoms and have been determined to be scale 1 or 2 by the visual evaluation of symptoms as described herein under General Methods Item 3. Fruits produced by these plants did show severe pulp deterioration. A representative picture of a fruit produced by such plants is given in FIG. 5.

*Citrullus lanatus* F1 plants and grafted plants ("NCIMB42624—Sugar Baby" and "NCIMB42624—Ercole") were further analysed for the presence of CGMMV Virus RNA in the leaves by means of dot-blot hybridization analyses (*) as described herein under General Methods items 5 and RT-PCR analysis(**) as described under General Methods Item 4 b). Results obtained are given in the following Table.

TABLE 3

| Host | dpi 14(*) | 30(**) | 40(*) | 60(**) | 90(*) |
|---|---|---|---|---|---|
| NCIMB 42624 | +/− | +/− | − | − | − |
| F1 (NCIMB 42624 × elite lines) | +/− | Not tested | − | − | − |
| Graft ("NCIMB 42624 - Ercole") | − | Not tested | − | Not tested | Not tested |

TABLE 3-continued

| Host | dpi 14(*) | 30(**) | 40(*) | 60(**) | 90(*) |
|---|---|---|---|---|---|
| Graft ("NCIMB 42624 - Sugar baby") | − | Not tested | − | +/− | − |
| Sugar baby (Positive control) | + | + | + | + | + |

The above Table 3 shows the results of the detection of CGMMV RNA in leaves of CGMMV resistant *Citrullus colocynhis* plants (NCIMB 42624), F1 plants obtained from crossing NCIMB 42624 x *Citrullus lanatus* subspecies *vulgaris* and grafted plants ("NCIMB 42624—Ercole" and "NCIMB 42624—Sugar baby") after infection with CGMMV by mechanical inoculation of the leaves or by grafting a non-infected scion to an infected root-stock. Plants from the CGMMV susceptible commercial variety Sugar Baby, were used as positive control. +/− indicates a very weak signal, − indicates no signal, + indicates a strong positive signal; dpi: days post infection. (*) Dot Blot method, (**) RT-PCR method.

For CGMMV susceptible control plants, the virus was detected throughout development of the plants from early (dpi 14) to late stage (dpi 90). Very weak signals for CGMMV RNA were detected in NCIMB42624 at early stages (dpi 14 and 30), but those signals disappeared at later stages (from dpi 40 on). A similar result was obtained for F1 plants (NCIMB 42624 x elite lines). For grafted plants no CGMMV RNA was detected in the leaves at any stage of development (from dpi 14 to dpi 90) with the exception that a weak signal was detected for the "NCIMB 42624—Sugar baby" graft at dpi 60. As can be seen from the following Table 4, further analysis of "NCIMB 42624—Sugar baby" grafts showed that a weak signal indicating presence of low amounts of CGMMV RNA was only due to virus being found in a single plant out of eight plants at early stage (dpi 14). At later stage (dpi 60) the signal in the same plant was neither detectable by dot-blot nor by PCR anymore.

TABLE 4

| Graft "NCIMB 42624 - Sugar baby" | Dot-Blot 14 dpi | Dot-Blot 60 dpi | PCR 60 dpi |
|---|---|---|---|
| 1 | − | − | − |
| 2 | − | − | − |
| 3 | − | − | − |
| 4 | − | − | − |
| 5 | − | − | No tested |
| 6 | −/+ | − | No tested |
| 7 | − | − | No tested |
| 8 | − | − | No tested |

The above Table 4 shows the results of the detection of CGMMV RNA in grafted plants ("NCIMB 42624—Sugar baby") after grafting to a CGMMV infected rootstock. +/− indicates a weak signal, − indicates no signal.

The above, non-quantitative but only qualitative, results of Table 3 and 4 are in conformity with the earlier quantitative results in Table 2, in that the very low level of virus at the early stages of resistant plants becomes progressively lower at later stages and is then only detectible using quantitative methods, i.e. only extremely low virus titers are found at 40 dpi or later at 60 dpi or thereafter. In addition, in the resistant scions no CGMMV virus could be detected using these qualitative methods. Further, also RT-qPCT was carried out on leaves obtained from scion-rootstock combinations, where the rootstock was infected with CGMMV as described in General Methods Item 6. The rootstock used was Sugar Baby.

Average Ct-values at 140-150 dpi of leaf samples were found to be as follows. Each replicate consists of 6 plants. Note that a low Ct-value indicates a high virus titer, while a high Ct-value indicates a low amount of virus.

TABLE 5

| Plant | Average Ct-value at 140-150 dpi | Symptoms |
|---|---|---|
| Leaf Sugar baby without CGMMV (mock) | 26.22 | No symptoms |
| Leaf of Sugar Baby infected with CGMVV (rep1) | 9.15 | Severe symptoms (scale 1) |
| Leaf of Sugar Baby infected with CGMVV (rep2) | 8.92 | Severe symptoms (scale 1) |
| Leaf of scion of graft: "NCIMB42624 - Sugar Baby" (rep1) | 27.36 | No symptoms (scale 4) |
| Leaf of scion of graft: "NCIMB42624 - Sugar Baby" (rep2) | 26.49 | No symptoms (scale 4) |

The above clearly demonstrated that NCIMB 42624 plants and plants of crosses between NCIMB 42624 x *Citrullus lanatus* subspecies *vulgaris* elite lines did not show any symptoms of CGMMV infection and contained very low, almost undetectable levels of virus in the upper leaves; and grafted plants comprising an NCIMB42624 scion grafted onto a CGMMV infected rootstock ("NCIMB42624—Sugar Baby" and "NCIMB42624—Ercole") do not show any symptoms of CGMMV infection on the scion. Thus, NCIMB 42624 plants are resistant to CGMMV, the resistance to CGMMV is transferable to other *Citrullus* species including *Citrullus lanatus* subspecies *vulgaris* elite lines and the resistance is maintained when CGMMV resistant scions are grafted onto CGMMV infected rootstocks.

Results item3—QTL mapping of CGMMV resistance found in NCIMB 42624 and marker development Three mapping populations were generated by crossing NCIMB 42624 with an elite watermelon line which is susceptible to CGMMV. One BC1 populations (backcross) and two F2 populations were made. Plants were mechanically inoculated with CGMMV as described and symptoms were evaluated using the visual scale described and also using ELISA tests to evaluate virus titers. Mapping was done using mostly symptoms assessed at 30 dpi or later.

In total seven QTLs were mapped (two on chromosome 1, one on chromosome 4, two on chromosome 5 and one on chromosome 7 and one on chromosome 9), of which 5 QTLs (QTL.1.1 on chromosome 1, QTL4.1 on chromosome 4, QTL5.2 on chromosome 5, QTL7.1 on chromosome 7 and QTL9.1 on chromosome 9, see Table 6 below, were used in further backcrossing and for these five QTLs SNP markers linked to these QTLs are provided below.

Two QTLs, QTL7.1 and QTL9.1, were dominant and resulted in plants having a symptom level of scale 3 or scale 4. They also had a significant effect on virus titer, which was significantly reduced in cultivated watermelons into which these QTLs were backcrossed.

In the Table below (Table 6), the chromosome of each of the five QTLs is indicated, as is the base pair (bp) position of the SNP in the genome of cultivated watermelon (see cucurbitgenomics.org, "Watermelon (Charleston Gray) genome"). The genotype of the SNP is indicated for the resistant parent (i.e. NCIMB 42624) and the Susceptible parent (elite watermelon line). The seed deposit NCIMB 42625 is homozygous for the SNP genotype and contains all five QTLs in homozygous form.

TABLE 6

| Cultivated watermelon chromosome (Chr) | Nucleotide position of the SNP in the watermelon genome (base number); | SNP marker linked to QTL (most closely linked marker is indicated) | SNP genotype of susceptible parent | SNP genotype of CGMMV resistant donor |
|---|---|---|---|---|
| Chr1 (QTL1.1) | 6,555,391 | SNP1 refers to nucleotide 51 in SEQ ID NO: 1 | TT | CC |
| Chr1 (QTL1.1) | 16,631,610 | SNP2 refers to nucleotide 51 in SEQ ID NO: 2 | AA | GG |
| Chr1 (QTL1.1) | 26,238,488 | SNP3 refers to nucleotide 51 in SEQ ID NO: 3 | TT | CC |
| Chr1 (QTL1.1) | 34,609,471 | SNP4 refers to nucleotide 51 in SEQ ID NO: 4 | TT | CC |
| Chr1 (QTL1.1) | 35,238,267 | SNP5 refers to nucleotide 51 in SEQ ID NO: 5 (most closely linked) | AA | GG |
| Chr1 (QTL1.1) | 35,766,439 | SNP6 refers to nucleotide 51 in SEQ ID NO: 6 | CC | TT |
| Chr4 (QTL4.1) | 4,230,711 | SNP7 refers to nucleotide 51 in SEQ ID NO: 7 | AA | TT |
| Chr4 (QTL4.1) | 24,321,690 | SNP8 refers to nucleotide 51 in SEQ ID NO: 8 (most closely linked) | AA | CC |
| Chr4 (QTL4.1) | 25,526,846 | SNP9 refers to nucleotide 51 in SEQ ID NO: 9 | GG | AA |
| Chr5 (QTL5.2) | 30,786,503 | SNP10 refers to nucleotide 51 in SEQ ID NO: 10 | CC | TT |
| Chr5 (QTL5.2) | 32,788,817 | SNP11 refers to nucleotide 51 in SEQ ID NO: 11 (most closely linked) | GG | AA |
| Chr5 (QTL5.2) | 36,842,501 | SNP12 refers to nucleotide 51 in SEQ ID NO: 12 | CC | TT |
| Chr7 (QTL7.1) | 4,784,519 | SNP13 refers to nucleotide 51 in SEQ ID NO: 13 | GG | AA |
| Chr7 (QTL7.1) | 7,848,633 | SNP14 refers to nucleotide 51 in SEQ ID NO: 14 (most closely linked) | GG | AA |

TABLE 6-continued

| Cultivated watermelon chromosome (Chr) | Nucleotide position of the SNP in the watermelon genome (base number); | SNP marker linked to QTL (most closely linked marker is indicated) | SNP genotype of susceptible parent | SNP genotype of CGMMV resistant donor |
|---|---|---|---|---|
| Chr7 (QTL7.1) | 8,334,624 | SNP15 refers to nucleotide 51 in SEQ ID NO: 15 | AA | GG |
| Chr7 (QTL7.1) | 11,166,694 | SNP16 refers to nucleotide 51 in SEQ ID NO: 16 | TT | GG |
| Chr7 (QTL7.1) | 18,775,728 | SNP17 refers to nucleotide 51 in SEQ ID NO: 17 | CC | TT |
| Chr7 (QTL7.1) | 21,389,410 | SNP18 refers to nucleotide 51 in SEQ ID NO: 18 | GG | AA |
| Chr9 (QTL9.1) | 31,394,464 | SNP19 refers to nucleotide 51 in SEQ ID NO: 19 | TT | CC |
| Chr9 (QTL9.1) | 32,499,549 | SNP20 refers to nucleotide 51 in SEQ ID NO: 20 | CC | GG |
| Chr9 (QTL9.1) | 34,607,108 | SNP21 refers to nucleotide 51 in SEQ ID NO: 21 | AA | GG |
| Chr9 (QTL9.1) | 35,343,850 | SNP22 refers to nucleotide 51 in SEQ ID NO: 22 (most closely linked) | TT | CC |
| Chr9 (QTL9.1) | 36,923,004 | SNP23 refers to nucleotide 51 in SEQ ID NO: 23 | TT | CC |
| Chr9 (QTL9.1) | 38,321,162 | SNP24 refers to nucleotide 51 in SEQ ID NO: 24 | TT | GG |

For each SNP the sequence is provided in the sequence listing and herein and the sequence has the same number as the SNP. The sequence contains the SNP nucleotide of the resistant donor. So for SNP1 the sequence comprising the resistant parent SNP (a 'C' at position 51) is provided as SEQ ID NO: 1, etc. See also Table 1.

BC3 and F2 lines have been generated containing different combinations of QTLs and single QTLs. These will be evaluated for their CGMMV resistance and virus titers following inoculation. Also the virus titers will be evaluated and whether the very low virus titers result in transmissibility of the virus to susceptible watermelon plants or to other hosts, such as cucumber. Likewise, transmissibility of the virus to seeds produced on CGMMV resistant plants will be studied.

In addition, fine mapping will be done. "Fine-mapping" refers to methods by which the position of a QTL can be narrowed down. For example a large population segregating for the trait can be analysed for segregation of the trait and the SNP markers and plants comprising recombination events in the region between the markers can be selected, in order to determine between which pair of SNP markers the QTL is located. One can also search for additional markers near or flanking the most linked marker to narrow down the interval in which the QTL is located.

Examples: Virus Transmission from NCIMB42624 Plants (C. colocynthis Accession) to Cucumber and Susceptible Watermelon Plants Leaves of a plant of NCIMB42624, which was mechanically inoculated with CGMMV virus European type VE459 (as described above) but showed no symptoms (scale 4), was used to make inoculum and the inoculum was used to mechanically inoculate 215 plants of the cucumber variety Sheila and 193 plants of watermelon variety Sugar Baby. After about 30 dpi the plants were visually assessed for CGMMV symptoms and also a PCR assay was carried out to detect virus in the leaves.

The results are shown below in Table 7:

| Nr. of plants with Symptoms | Nr. of plants without symptoms | Nr of plants positive in CGMMV PCR | % of plants wherein virus was transmitted |
|---|---|---|---|
| Cucumber variety Sheila | | | |
| 1 | 214 | 1 | 0.46% |
| Watermelon variety Sugar Baby | | | |
| 0 | 193 | 0 | 0.00% |

The results showed that only a single cucumber plant was infected by the inoculum (a single plant showed symptoms and was positive in the PCR test), while none of the watermelon plants were infected by the inoculum. This means that the resistant C. colocynthis accession deposited under NCIMB 42624 does not allow CGMMV transmission to watermelon plants and only very low levels of transmission to cucumber plants (less than 1% of plants become infected).

Examples: Seed Transmissibility of CGMMV in Watermelon Lines Containing Various Combinations of QTLs from the C. colocynthis Donor (NCIMB 42624)

Various F3 families which contained one or more QTLs from the C. colocynthis donor and which had survived mechanical CGMMV inoculation were allowed to set fruits and the seeds produced in these fruits were analyzed for CGMMV virus using quantitative PCR (RT-qPCR) as described above. The aim was to determine whether the QTLs could prevent seed infection and thus seed transmissibility of the virus. qPCR was carried out at 210 dpi. A low Ct value indicates a high virus titre and a high Ct value (above 30) indicates a low virus titre.

Results are shown in Table 8:

| Line | Fruit symptoms | qPCR on seeds of fruits: Ct value | Interpretation of seed infection of the virus |
|---|---|---|---|
| X16_4305-15 | NO | 37.09 | Negative |
| X16_4310-17 | NO | 36.93 | Negative |
| X16_4311-11 | NO | 34.08 | Negative |
| X16_4311-8 | NO | 35.46 | Negative |
| Sugar baby Mock | NO | nd | Negative |
| X16_4306-1 | NO | 33.70 | Negative |
| X16_4310-9 | NO | 34.28 | Negative |
| X16_4310-35 | NO | 35.49 | Negative |
| X16_4310-8 | NO | 36.00 | Negative |
| X16_4307-24 | NO | 38.01 | Negative |
| X16_4311-6 | NO | 32.50 | Negative |
| X16_4305-20 | NO | 32.25 | Negative |
| X16_4312-4 | NO | 38.66 | Negative |
| X16_4312-2 | NO | 22.86 | Positive |
| X16_4307-22 | NO | 22.99 | Positive |
| X16_4312-6 | NO | 32.40 | Negative |
| X16_4311-3 | NO | 32.85 | Negative |
| X16_4305-8 | NO | 34.55 | Negative |
| X16_4305-17 | NO | 18.56 | Positive |
| X16_4310-15 | NO | 25.22 | Positive |
| X16_4312-16 | NO | 24.98 | Positive |
| X16_4307-9 | NO | 24.45 | Positive |
| X16_4312-10 | NO | 19.28 | Positive |
| X16_4311-1 | NO | 17.44 | Positive |
| Sugar baby | YES | 19.70 | Positive |
| X16_4305-10 | NO | 20.16 | Positive |
| X16_4307-12 | NO | 17.46 | Positive |

The results showed that all lines which contained at least QTL 9.1 and/or QTL 7.1 were negative for CGMMV virus transmission to the seeds. Especially presence of at least QTL9.1 seemed to prevent seed transmission of the virus.

Examples: Comparison of *C. colocynthis* Accessions for CGMMV Resistance

Ten seeds of various *C. colocynthis* accessions were germinated and the plants were mechanically inoculated as described above, in order to compare the CGMMV resistance to the resistance of the accession deposited under NCIMB 42624. Each plant was phenotyped using the scale 1 (severe symptoms), 2 (medium symptoms), 3 (mild symptoms) and 4 (no symptoms). It is noted that PI accessions are known to be heterogenous.

Many PI accessions did not germinate and could therefore not be assessed.

The following PI accessions could be assessed: PI537300, PI542616, PI549161, GRIF14201, PI220778, PI386015, PI432337, PI388770 and PI386018. Three of these accessions (PI537300, PI386015, PI388770) were part of the USDA core collection and have been described to have potential CGMMV tolerance (CucCAP, Second Annual CucCAP Team Meeting, Mar. 27-28 2017, Chareleston, page 26 and 27, 'Evaluation of the watermelon PI collection for resistance to Cucumber green mottle mosaic virus CGMMM and conducting genome-wide association mapping to identify SNPs associated with CGMMV resistance', in combination with the *C. colocynthis* accessions of the USDA core collection as indicated in the GRIN collection in which only 4 *C. colocynthis* accessions are part of the 'core subset'; three of the 4 core subsets were included in this test, but PI525082 could unfortunately not be included in this test).

However, in our test all tested accessions, including the three accessions of the USDA core collection, had an average symptom score of 3 or less (average of the individual plants), with not a single plant in the entire test having a score of 4 (no symptoms), except NCIMB 42624 of the invention (all of which plants had a score of 4). Of all the other *C. colocynthis* accessions PI386015 had the best CGMMV tolerance, with all plants having a score of 3 (mild symptoms). PI537300 had 6 plants with a score of 3 (mild symptoms) and 4 plants with a score of 2 (medium symptoms). PI388770 had 6 plants with a score of 1 (severe symptoms), three plants with a score of 2 (medium symptoms) and one plant with a score of 3 (mild symptoms).

The test confirmed that the CGMMV resistance in the selected *C. colocynthis* deposited under NCIMB42624 is of a higher resistance level than any of the other *C. coloynthis* accessions tested, which at most have tolerance (score 3, mild symptoms).

The invention claimed is:

1. A cultivated watermelon plant or plant cell comprising an introgression fragment on chromosome 9 and/or on chromosome 7 of a CGMMV resistant donor plant of the species *Citrullus colocynthis*, wherein the introgression fragment on chromosome 9 comprises a CGMMV resistance QTL from a *C. colocynthis* donor of which a representative sample has been deposited under accession number NCIMB 42624 and comprises a Cytosine for SNP22 at nucleotide 51 of SEQ ID NO: 22, corresponding to nucleotide 35,343,850 of chromosome 9 of the Watermelon Charleston Grey genome, and wherein the introgression fragment on chromosome 7 comprises a CGMMV resistance QTL from a *C. colocynthis* donor of which a representative sample has been deposited under accession number NCIMB 42624 and comprises a Adenine for SNP14 at nucleotide 51 of SEQ ID NO: 14, corresponding to nucleotide 7,848,633 of chromosome 7 of the Watermelon Charleston Grey genome.

2. The cultivated watermelon plant or plant cell according to claim 1, wherein the QTL on chromosome 9 is in-between SNP21 at nucleotide 51 of SEQ ID NO: 21, corresponding to nucleotide 34,607,108 of chromosome 9, and SNP23 at nucleotide 51 of SEQ ID NO: 23, corresponding to nucleotide 36,923,004 of chromosome 9, and wherein the QTL on chromosome 7 is in-between SNP13 at nucleotide 51 of SEQ ID NO: 13, corresponding to nucleotide 4,784,519 of chromosome 7, and SNP16 at nucleotide 51 of SEQ ID NO: 16, corresponding to nucleotide 11,166,694 of chromosome 7.

3. A cultivated watermelon plant or plant cell according to claim 1, wherein the introgression fragment on chromosome 7 comprises a Adenine at nucleotide 51 of SEQ ID NO: 14, and a Guanine at nucleotide 51 of SEQ ID NO: 15; and wherein the introgression fragment on chromosome 9 comprises a Cytosine at nucleotide 51 of SEQ ID NO: 22, and a Cytosine at nucleotide 51 of SEQ ID NO: 23.

4. The cultivated watermelon plant or plant cell according to claim 1, wherein the introgression fragment on chromosome 7 is in homozygous or in heterozygous form and/or wherein the introgression fragment on chromosome 9 is in homozygous form or in heterozygous form.

5. The cultivated watermelon plant or plant cell according to claim 1, wherein the plant comprises a CGMMV resistance of scale 3 (mild symptoms) or scale 4 (no symptoms).

6. The cultivated watermelon plant or plant cell according to claim 1, wherein the plant or plant cell is an inbred plant or plant cell, or an F1 hybrid plant or plant cell, or a diploid or tetraploid or triploid plant or plant cell.

7. A seed which grows into a plant according to claim 1.

8. A cultivated watermelon fruit or fruit part comprising plant cells according to claim 1.

9. A cultivated watermelon plant propagation material comprising a cultivated watermelon plant cell according to claim 1.

10. A method for producing triploid hybrid cultivated watermelon seeds comprising the following steps:
a) providing a first CGMMV resistant inbred diploid watermelon plant comprising two chromosomes 7, each having an introgression fragment from chromosome 7 comprising a CGMMV resistance QTL from a *C. colocynthis* donor of which a representative sample has been deposited under accession number NCIMB 42624 and comprises a Adenine for SNP14 at nucleotide 51 of SEQ ID NO: 14, corresponding to nucleotide 7,848,633 of chromosome 7 of the Watermelon Charleston Grey genome;
b) providing a second CGMMV resistant inbred tetraploid watermelon plant comprising four chromosomes 7 each having an introgression fragment from chromosome 7 comprising a CGMMV resistance QTL from a *C. colocynthis* donor of which a representative sample has been deposited under accession number NCIMB 42624 and comprises a Adenine for SNP14 at nucleotide 51 of SEQ ID NO: 14, corresponding to nucleotide 7,848,633 of chromosome 7 of the Watermelon Charleston Grey genome;
c) allowing pollination of the tetraploid watermelon plant provided in step b) with pollen of the diploid watermelon plant provided in step a); and
d) collecting seeds from the fruits produced in step c).

11. A method for producing triploid hybrid cultivated watermelon seeds comprising the following steps:
a) providing a first CGMMV resistant inbred diploid watermelon plant comprising two chromosomes 9, each having an introgression fragment from chromosome 9 comprising a CGMMV resistance QTL from a *C. colocynthis* donor of which a representative sample has been deposited under accession number NCIMB 42624 and comprises a Cytosine for SNP22 at nucleotide 51 of SEQ ID NO: 22, corresponding to nucleotide 35,343,850 of chromosome 9 of the Watermelon Charleston Grey genome;
b) providing a second CGMMV resistant inbred tetraploid watermelon plant comprising four chromosomes 9 each having an introgression fragment from chromosome 9 comprising a CGMMV resistance QTL from a *C. colocynthis* donor of which a representative sample has been deposited under accession number NCIMB 42624 and comprises a Cytosine for SNP22 at nucleotide 51 of SEQ ID NO: 22, corresponding to nucleotide 35,343,850 of chromosome 9 of the Watermelon Charleston Grey genome;
c) allowing pollination of the tetraploid watermelon plant provided in step b) with pollen of the diploid watermelon plant provided in step a); and
d) collecting seeds from the fruits produced in step c).

12. A method of screening plants or plant parts, or DNA derived therefrom, for the presence of a fragment on chromosome 7 comprising a CGMMV resistance QTL and/or on chromosome 9 comprising a CGMMV resistance QTL, comprising the steps of:

a) screening the genomic DNA for the SNP genotype of one or more or all of SNP13 at nucleotide 51 of SEQ ID NO: 13, SNP14 at nucleotide 51 of SEQ ID NO: 14, SNP15 at nucleotide 51 of SEQ ID NO: 15, SNP16 at nucleotide 51 of SEQ ID NO: 16, SNP17 at nucleotide 51 of SEQ ID NO: 17, and SNP18 at nucleotide 51 of SEQ ID NO: 18, linked to the QTL on chromosome 7, and/or for one or more of SNP19 at nucleotide 51 of SEQ ID NO: 19, SNP20 at nucleotide 51 of SEQ ID NO: 20, SNP21 at nucleotide 51 of SEQ ID NO: 21, SNP22 at nucleotide 51 of SEQ ID NO: 22, SNP23 at nucleotide 51 of SEQ ID NO: 23 and SNP24 at nucleotide 51 of SEQ ID NO: 25, linked to the QTL on chromosome 9;

b) and optionally selecting a plant or plant part which comprises an Adenine for SNP14 at nucleotide 51 of SEQ ID NO: 14, corresponding to nucleotide 7,848,633 of chromosome 7 of the Watermelon Charleston Grey genome and/or a Cytosine for SNP22 at nucleotide 51 of SEQ ID NO: 22, corresponding to nucleotide 35,343,850 of chromosome 9 of the Watermelon Charleston Grey genome.

13. The cultivated watermelon plant or plant cell according to claim 1, wherein the introgression fragment on chromosome 7 further comprises a Adenine at nucleotide 51 of SEQ ID NO: 13 and/or a Guanine at nucleotide 51 of SEQ ID NO: 15 and/or a Guanine at nucleotide 51 of SEQ ID NO: 16, and/or a Thymine at nucleotide 51 of SEQ ID NO: 17, and/or an Adenine at nucleotide 51 of SEQ ID NO: 18.

14. The cultivated watermelon plant or plant cell according to claim 1, wherein the introgression fragment on chromosome 9 further comprises a Cytosine at nucleotide 51 of SEQ ID NO: 19, and/or a Guanine at nucleotide 51 of SEQ ID NO: 20, and/or a Guanine at nucleotide 51 of SEQ ID NO: 21, and/or a Cytosine at nucleotide 51 of SEQ ID NO: 23, and/or a Guanine at nucleotide 51 of SEQ ID NO: 24.

15. The cultivated watermelon plant or plant cell according to claim 2, wherein the introgression fragment on chromosome 9 further comprises a Guanine for SNP21 at nucleotide 51 of SEQ ID NO: 21 and/or comprises a Cytosine for SNP23 at nucleotide 51 of SEQ ID NO: 23 and wherein the introgression fragment on chromosome 7 further comprises a Adenine for SNP13 at nucleotide 51 of SEQ ID NO: 13 and/or a Guanine at nucleotide 51 of SEQ ID NO: 15 and/or a Guanine for SNP16 at nucleotide 51 of SEQ ID NO: 16.

* * * * *

SEQUENCE LISTING

```
<160> NUMBER OF SEQ ID NOS: 29

<210> SEQ ID NO 1
<211> LENGTH: 101
<212> TYPE: DNA
<213> ORGANISM: Citrullus colocynthis

<400> SEQUENCE: 1
aagtacagtt gcaaatataa taatcaggtt taaaatattt gcaaatatag caaaatttag     60
attctgcttt taaagtctaa cagtgataga ccatatcagt g                        101

<210> SEQ ID NO 2
<211> LENGTH: 101
<212> TYPE: DNA
<213> ORGANISM: Citrullus colocynthis

<400> SEQUENCE: 2
ggaaaaagaa attacatgga atgcatcgtt attgtttcat ttatatcccc gtatagatca     60
atgtaaactt gaagttcgga aaataattca tttgcaaaat a                        101
```

<210> SEQ ID NO 3
<211> LENGTH: 101
<212> TYPE: DNA
<213> ORGANISM: Citrullus colocynthis

<400> SEQUENCE: 3
ttgttagtgc aacaaatgtg tagacatgca taaaacactt gttagtgcaa cgaatgtgtt    60
agacatatat gacaataata aaaaaatttg aatatgaaaa t                       101

<210> SEQ ID NO 4
<211> LENGTH: 101
<212> TYPE: DNA
<213> ORGANISM: Citrullus colocynthis

<400> SEQUENCE: 4
ggcggaacgc cgaccggaag gtttagcaac ggcaaaatcc ccaccgattt cgtaggtggg    60
gctcctaata attcatttta tctctcctct aataacattt t                       101

<210> SEQ ID NO 5
<211> LENGTH: 101
<212> TYPE: DNA
<213> ORGANISM: Citrullus colocynthis

<400> SEQUENCE: 5
ctctacatta gagaggactt tgaagttgtt gacaggaaaa catggctgca ggcaagttac    60
ttttagcccc aagttttag tggttgatgt ctcttttaaa t                        101

<210> SEQ ID NO 6
<211> LENGTH: 101
<212> TYPE: DNA
<213> ORGANISM: Citrullus colocynthis

<400> SEQUENCE: 6
tctattttgc gttccactct tcgcattctc tcttctacaa gaaaatagcc tctattctat    60
cttcatttag gggctttctt tcttataact ttcatctagg g                       101

<210> SEQ ID NO 7
<211> LENGTH: 101
<212> TYPE: DNA
<213> ORGANISM: Citrullus colocynthis

<400> SEQUENCE: 7
aattttgaac ctgatataaa ctcaacatca ttgattagat cgcaaacttc tgtttgttct    60
caagcttctt tcattgaatc caaatattga gtaaaataca c                       101

<210> SEQ ID NO 8
<211> LENGTH: 101
<212> TYPE: DNA
<213> ORGANISM: Citrullus colocynthis

<400> SEQUENCE: 8
ttggcgtggg cttgtaccat atagtgtttg ccttcaagtg attgcaattt ctagtttcaa    60
tcttgagttt ggtattcaat actgaaagcc tcattgccat t                       101

<210> SEQ ID NO 9
<211> LENGTH: 101
<212> TYPE: DNA
<213> ORGANISM: Citrullus colocynthis

<400> SEQUENCE: 9
tttatttgtc aatttcatca gcaaaattgt cttgaaaatt gatgcttagc atacctttttc    60 tttctagaaa tgcttcaaaa cctccgggtt caatggcgca g    101

<210> SEQ ID NO 10
<211> LENGTH: 101
<212> TYPE: DNA
<213> ORGANISM: Citrullus colocynthis

<400> SEQUENCE: 10
agatcagatg catttacgtc cggcttcact tcattttgag tagagttcac tgttattttg    60
ttgatggatt cgcccgagat aacaccagac ttttctggag a    101

<210> SEQ ID NO 11
<211> LENGTH: 101
<212> TYPE: DNA
<213> ORGANISM: Citrullus colocynthis

<400> SEQUENCE: 11 gaagggcaa ttgaacccct tgtccaaatg ttccgtactg aaaagcttga agctaaatta    60
tcggcattaa gcgcattgca aagcctctca ggcttgaagg a    101

<210> SEQ ID NO 12
<211> LENGTH: 101
<212> TYPE: DNA
<213> ORGANISM: Citrullus colocynthis

<400> SEQUENCE: 12
taatgtgccg aactccaaat attaaggcac aaggttatgg tgtggtgtgg tgctgaatgt    60
accacattct acgccatgct attcctaact taaaccagcc t    101

<210> SEQ ID NO 13
<211> LENGTH: 101
<212> TYPE: DNA
<213> ORGANISM: Citrullus colocynthis

<400> SEQUENCE: 13 gagttttttca agtgatgatt tgagttggga gatctgagag ccttggacat aagtgtttct    60
cctgtacatt ttttgttgtt ggttcactag attgttgttc t    101

<210> SEQ ID NO 14
<211> LENGTH: 101
<212> TYPE: DNA
<213> ORGANISM: Citrullus colocynthis

<400> SEQUENCE: 14
tttcgagaag acttatctca tacaatagta tatgagctga actactagag aaacatcaat    60
cacaaacttt catctgttaa atcttagaag aactggtttg g    101

<210> SEQ ID NO 15
<211> LENGTH: 101
<212> TYPE: DNA
<213> ORGANISM: Citrullus colocynthis

<400> SEQUENCE: 15
tgaccaccca aatattttcc aaatttgcag attttttcaa aaaatgaaag gtagcgcaac    60
tgcgctctaa aagagcatag ctacactttg ggaattttttt c    101

<210> SEQ ID NO 16
<211> LENGTH: 101
<212> TYPE: DNA
<213> ORGANISM: Citrullus colocynthis

<400> SEQUENCE: 16
actttgtttt tcttcaattc tctctaaatt tatcattcta gatcacctat gatctttaat    60
gccctggaac tgtaaaaata aattgtaatt taaaggagtc a    101

<210> SEQ ID NO 17
<211> LENGTH: 101
<212> TYPE: DNA
<213> ORGANISM: Citrullus colocynthis

<400> SEQUENCE: 17
ggtggtgctg gtgatgttgt tgatgttaag attaaaggct cttctactgg ttggcttcaa    60
atgtcaagga attggggtca aaattggcag gttggtacct t    101

<210> SEQ ID NO 18
<211> LENGTH: 101
<212> TYPE: DNA
<213> ORGANISM: Citrullus colocynthis

<400> SEQUENCE: 18
ataaaattaa atgaaaacgc cttagaaaca tcagagaatt catttctcca aaaggaagaa    60
gaattctgca atagaatcct agagttggag aacagactgg a    101

<210> SEQ ID NO 19
<211> LENGTH: 101
<212> TYPE: DNA
<213> ORGANISM: Citrullus colocynthis

<400> SEQUENCE: 19
cgtcggagtt gggccttaag gcgaatgtta gtgttggttg acagatggtt ctcattggag    60
ttgatcatcc aaggtggtcg ttggagcatg aagttgttcg g    101

<210> SEQ ID NO 20
<211> LENGTH: 101
<212> TYPE: DNA
<213> ORGANISM: Citrullus colocynthis

<400> SEQUENCE: 20
aaagatggag aggatctttg taggttgcac gaccaacgct tccattggga ggcatgtctc    60
tctggttcat ggtaagctga atgacattgt tggaagggta t    101

<210> SEQ ID NO 21
<211> LENGTH: 101
<212> TYPE: DNA
<213> ORGANISM: Citrullus colocynthis

<400> SEQUENCE: 21
gcctcaactt cgtttctttt ttctctttct tttatagttc ctctactatt gctccttctg    60
tatctcctgc tgagttcttt tgctctaaca accaattttc t    101

<210> SEQ ID NO 22
<211> LENGTH: 101
<212> TYPE: DNA
<213> ORGANISM: Citrullus colocynthis

<400> SEQUENCE: 22

```
ttatcaagag atccatataa gtatgttgtc tacatccata agatgcatgt ccagattttc    60
attcacagtc agactaatta aatatcttaa tgtaattgca t                       101
```

<210> SEQ ID NO 23
<211> LENGTH: 101
<212> TYPE: DNA
<213> ORGANISM: Citrullus colocynthis

<400> SEQUENCE: 23

```
aataaatagt acaaatatca atttataccc taaacgattt aaaccccaaa ctaatagttg    60
tatcaattaa aaccataaat tttcattagt gtatcaattt a                       101
```

<210> SEQ ID NO 24
<211> LENGTH: 101
<212> TYPE: DNA
<213> ORGANISM: Citrullus colocynthis

<400> SEQUENCE: 24

```
aaggtagggt ttggccttca ggatagtgac gacattgatg cgttgtttgt gaaatctgtg    60
gaggaggttc cgtataatat ctctgtgatt cagatcagta a                       101
```

<210> SEQ ID NO 25
<211> LENGTH: 29
<212> TYPE: DNA
<213> ORGANISM: artificial
<220> FEATURE:
<223> OTHER INFORMATION: reverse primer

<400> SEQUENCE: 25

```
ttgcatgctg ggccctacc cggggaaag                                       29
```

<210> SEQ ID NO 26
<211> LENGTH: 28
<212> TYPE: DNA
<213> ORGANISM: artificial
<220> FEATURE:
<223> OTHER INFORMATION: forward primer

<400> SEQUENCE: 26

```
ccgaattcat ggcttacaat ccgatcac                                       28
```

<210> SEQ ID NO 27
<211> LENGTH: 21
<212> TYPE: DNA
<213> ORGANISM: artificial
<220> FEATURE:
<223> OTHER INFORMATION: sense primer

<400> SEQUENCE: 27

```
gcatagtgct ttcccgttca c                                              21
```

<210> SEQ ID NO 28
<211> LENGTH: 24
<212> TYPE: DNA
<213> ORGANISM: artificial
<220> FEATURE:
<223> OTHER INFORMATION: antisense primer

<400> SEQUENCE: 28

```
tgcagaatta ctgcccatag aaac                                           24
```

<210> SEQ ID NO 29
<211> LENGTH: 23

```
<212> TYPE: DNA
<213> ORGANISM: artificial
<220> FEATURE:
<223> OTHER INFORMATION: probe

<400> SEQUENCE: 29
cggtttgctc attggtttgc gga                                           23
```